United States Patent
Cumberford et al.

(10) Patent No.: US 11,707,497 B2
(45) Date of Patent: *Jul. 25, 2023

(54) **METHODS AND COMPOSITIONS WITH PURIFIED *BOMBYX MORI* COCOON SILK PEPTIDE FIBER AND REFINED *BUGLOSSOIDES ARVENSIS* SEED OIL PROVIDING ANTI-INFLAMMATORY EFFECTS AND NEUROPROTECTION FOR DISEASE STATES**

(71) Applicant: Brain Health Holding LLC, Arden, NC (US)

(72) Inventors: Gregory Cumberford, Canby, OR (US); Troylyn Ball, Arden, NC (US); Marcus Goddard, Rothesay (CA)

(73) Assignee: Brain Health Holding LLC, Arden, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/721,343

(22) Filed: Apr. 14, 2022

(65) Prior Publication Data

US 2022/0323529 A1     Oct. 13, 2022

Related U.S. Application Data

(63) Continuation-in-part of application No. 17/067,489, filed on Oct. 9, 2020, now Pat. No. 11,357,810.

(60) Provisional application No. 62/912,956, filed on Oct. 9, 2019.

(51) Int. Cl.
| | |
|---|---|
| *A61K 36/30* | (2006.01) |
| *A61K 38/17* | (2006.01) |
| *A61K 36/45* | (2006.01) |
| *A61K 31/202* | (2006.01) |
| *A61P 25/00* | (2006.01) |
| *A61P 25/16* | (2006.01) |
| *A61P 25/22* | (2006.01) |
| *A61P 25/28* | (2006.01) |
| *A61K 31/197* | (2006.01) |

(52) U.S. Cl.
CPC .......... *A61K 36/30* (2013.01); *A61K 31/197* (2013.01); *A61K 31/202* (2013.01); *A61K 36/45* (2013.01); *A61K 38/1767* (2013.01); *A61P 25/00* (2018.01); *A61P 25/16* (2018.01); *A61P 25/22* (2018.01); *A61P 25/28* (2018.01)

(58) Field of Classification Search
None
See application file for complete search history.

(56) References Cited

U.S. PATENT DOCUMENTS

| | | | |
|---|---|---|---|
| 6,497,893 B1 | 12/2002 | Evehard et al. | |
| 6,642,361 B2 | 11/2003 | Hunter et al. | |
| 7,115,388 B2 | 10/2006 | Tsubouchi | |
| 7,193,038 B2 | 3/2007 | Tsubouchi et al. | |
| 9,187,538 B2 | 11/2015 | Altman et al. | |
| 9,682,048 B1 | 6/2017 | Rosen | |
| 9,901,562 B2 | 2/2018 | Levy et al. | |
| 10,010,574 B2 | 7/2018 | Kim et al. | |
| 10,154,980 B2 | 12/2018 | Levy et al. | |
| 2008/0213357 A1 | 9/2008 | Hebard et al. | |
| 2009/0280199 A1 | 11/2009 | Russell | |
| 2015/0166615 A1 | 6/2015 | Xia et al. | |
| 2016/0082065 A1 | 3/2016 | Brown et al. | |
| 2017/0107264 A1 | 4/2017 | Wang et al. | |
| 2018/0169179 A1 | 6/2018 | Kang | |
| 2018/0303891 A1 | 10/2018 | Gaudout et al. | |

FOREIGN PATENT DOCUMENTS

| | | |
|---|---|---|
| CN | 108783294 A1 | 11/2018 |
| KR | 20030077902 A1 | 10/2003 |
| KR | 101430387 B1 | 8/2014 |
| WO | 2013/149323 A1 | 10/2013 |

OTHER PUBLICATIONS

Bell et al., "A pilot dose-response study of the acute effects of haskap berry extract (*Lonicera caerulea* L.) on cognition, mood, and blood pressure in older adults" Eur. J. of Nutr. 58:3325-3334 (2019).
Haniadka et al., "A review of the gastroprotective effects of ginger (*Zingiber officinale* Roscoe)" Food & Function 4:845-855 (2013).
Hurwitz, "Gastric Hypochlorhydria and Achlorhydria in Older Adults-Reply" JAMA 278(20):1659-1660 (1997) (Abstract only).
Kim et al., "The Role of BF-7 on Enhancement of Memory and Cognitive Function" The Korean J. Anat. 37(6):519-527 (2004).
Kim et al., "Brain Factor-7 Extracted from Bombyx mori Enhances Cognition and Attention in Normal Children" J. Med. Food 12(3):643-648 (2009).
Law et al., "Neuroprotective effects of orientin on hydrogen peroxide-induced apoptosis in SH-SY5Y cells" Molec. Med. Reports 9:947-954 (2014).
Lefort et al., "Consumption of Buglossoides arvensis seed oil is safe and increases tissue long-chain n-3 fatty acid content more than flax sded oil—results of a phase I randomized clinical trial" J. Nutr. Sci. 5(e2):1-12 (2016).

(Continued)

*Primary Examiner* — Terry A McKelvey
*Assistant Examiner* — Catheryne Chen
(74) *Attorney, Agent, or Firm* — Amin Talati Wasserman LLP; George M. Carrera, Jr.; Valerie Neymeyer-Tynkov

(57) ABSTRACT

The present invention is directed to compositions comprising purified *Bombyx mori* cocoon silk peptide fiber, refined *Buglossoides arvensis* seed oil, and optionally Blueberry extract, and related methods for decreasing inflammation and providing neuroprotection. The compositions provide synergistic effects and may be used to treat relevant diseases and disorders.

13 Claims, 69 Drawing Sheets

(56) References Cited

OTHER PUBLICATIONS

Le Poncin-Seac'h et al., "Memory efficiency effects of a fish protein hydrolysate (FPHD800) comparatively with Ginkgo Biloba extract (EGb 761®) in healthy humans" Medecine & Longevite 2(2): 57067 (2010) (Summary only).

Park et al., "Neuroprotective effects of Liriope platyphylla extract against hydrogen peroxide-induced cytotoxicity in human neuroblastoma SH-SY5Y cells" BMC Complementary and Alternative Medicine 15:171 (2015) (pp. 1-11).

Sachdeva, "Cognitive Enhancement using Odor as Intervention" Dissertation, Dept. Elect. Instrument. Engineering, Thapar University, Patalia (Jun. 2014).

Shi et al., "Dosage effects of EGb761 on hydrogen peroxide-induced cell death in SH-SY5Y cells" Chemico-Biological Interactions 180:389-397 (2009).

Soholm, "Clinical improvement of memory and other cognitive functions by Ginkgo biloba: review of relevant iterature" Advances in Therapy 15(1):54-65 (1998 (Abstract only).

Sowndhararajan and Kim, "Review: Influence of Fragrances on Human Psychophysiological Activity: With Special Reference to Human Electroencephalographic Response" Scientia Pharmaceutica 84:724-751 (2016).

Tomotake, "Silkworm Pupai (*Bombyx mori*) Are New Sources of High Quality Protein and Lipid" J. Nutr. Sci. Vitamin. 56(6):446-448 (2010) (Abstract only).

Tin et al., "Baicalin prevents the production of hydrogen peroxide and oxidative stress induced by a aggregation in SH-SY5Y cells" Neurosci Letts. 492:76-79(2011).

CNS Vital Signs, "Brief Interpretation Guide", www.cnsvs.com, CNS Vital Signs Inc., Morrisville, NC (2019) (15 pages).

Nature's Crops AHIFLOWER® Seed Oil, Product AHI-O-NCI-1F, "Product Data Sheet" (Revision Date Apr. 2, 2019) and "Certificate of Analysis" (Jan. 26, 2018), Nature's Crops International, Kensington PE Canada. (4 pages).

Nature's Crops AHIFLOWER® Seed Oil Modified—Starch SDA Powder, Product Code: WE 102085, "Product Data Sheet" (Jun. 12, 2018) and "Certificate of Analysis" (Feb. 5, 2019), Nature's Crops International, Kensington PE Canada. (2 pages).

"BLUE d'Or Wild Blueberry Powder Specifications Sheet", Fruit d'Or Inc., Villeroy Canada: as Reviewed and Modified Mar. 15, 2019.

Blue d'Or, "Organic Wild Blueberry Powder 60 mesh, Certificate of Analysis", Fruit d'Or Inc., Villeroy Canada: dated Mar. 15, 2019.

Noh et al.; "Brain Factor-7 Improves Learning and Memory Deficits and Attenuates Ischemic Brain Damage by Reduction of ROS Generation in Stroke in Vivo and in vitro;" Laboratory Animal Research 36:24; 10 pages (2020).

Sekikawa et al., "Cognitive function improvement with astaxanthin and tocotrienol intake: a randomized, double blind, placebo-controlled study" J. Clin. Biochem. Nutr. 67:307-316 (2020).

US Patent and Trademark Office, International Searching Authority, "International Search Report" and "Written Opinion" dated Feb. 17, 2021 in counterpart PCT Appln. No. PCT/US2020/055137, 11 pages.

Wikipedia, "Lithospermum", Jan. 11, 2019, entire document especially p. 1, https://en.wikipedia.org/w/index.php?title=Lithospermum&oldid=877953648, 3 pages.

Daniells, Stephen, "Unexplored: Could haskap berries improve blood pressure and memory in older adults?" https://www.nutraingredients-usa.com/Article/2019/01/09/Unexplored-Could-haskap-berries-improve-blood-pressure-and-memory-in-older-adults# (Jan. 9, 2019), 2 pages.

Choi, J.H., et al., "Effects of Silk Fibroin Powder on Lipofuscin, Acetylcholine and Its Related Enzyme Activities in Brain of SD Rats," Journal of sericultural and entomological science, 2000. 42(2): p. 120-125.

Lee, S.H., et al., "The Improvement of Learning and Memory Ability of Normal Persons by BF-7," Korean J Physiol Pharmacol, Dec. 2004 8: p. 307-312.

Lee, M.Y., et al., "BF-7 Improved Memory Function and Protected Neuron from Oxidative Stress," Korean J. Phys. Anthropol, 2004. 17: p. 313-320.

Lee, S.-H., et al., "Association between Cerebral Blood Flow and Cognitive Improvement Effect by B. mori Extracted Component," Journal of Sericultural and Entomological Science, 2004. 46(2): p. 77-79.

Kang, Y.K., et al., "Effect of a fibroin enzymatic hydrolysate on memory improvement: A placebo-controlled, double-blind study," Nutrients, 2018. 10:233 (13 pages).

Kim, D.H., et al., "The Improvement of Short- and Long-term Memory of Young Children by BF-7," Journal of the Korean Society of Food Science and Nutrition, 2010 39(3): p. 376-382.

Kim, D.H., et al., "Milk Containing BF-7 Enhances the Learning and Memory, Attention, and Mathematical Ability of Normal Persons," Korean Journal for Food Science of Animal Resources, 2009. 29(2): p. 278-282.

Kim, D.H., et al., "Milk with Brain Factor-7 (BF-7 milk) enhances attention and cognition in normal persons," Milchwissenschaft, 2009. 64(3): p. 300-304.

Kim et al., "Neuroprotection and enhancement of learning and memory by BF-7," Journal of Health Science, 51(3):317-324 (2005).

Krikorian, R., et al., "Blueberry supplementation improves memory in older adults," Journal of Agricultural and Food Chemistry, 2010. 58(7): p. 3996-4000 (submitted 12 pages).

Montgomery, P., et al., "Low Blood Long Chain Omega-3 Fatty Acids in UK Children Are Associated with Poor Cognitive Performance and Behavior: A Cross-Sectional Analysis from the DOLAB Study," PLoS ONE, 2013. 8(6). (11 pages).

Poulose, S.M., et al., "Neurochemical differences in learning and memory paradigms among rats supplemented with anthocyanin-rich blueberry diets and exposed to acute doses of 56 Fe particles," Life sciences in space research, 2017. 12: p. 16-23.

Vauzour, D. et al., "The impact of blueberry flavonoids on learning and memory," Agro Food Industry Hi-Tech, 2011. 22(5): p. 13-15.

Whyte, A.R., et al., "A randomized, double-blinded, placebo-controlled study to compare the safety and efficacy of low dose enhanced wild blueberry powder and wild blueberry extract (Thinkblue™) in maintenance of episodic and working memory in older adults," Nutrients, 2018. 10, 660 (14 pages).

Willis, L.M., et al., "Dietary polyunsaturated fatty acids improve cholinergic transmission in the aged brain," Genes & nutrition, 2009 4(4): p. 309-314.

Zamroziewicz, M.K., et al., "Predictors of memory in healthy aging: Polyunsaturated fatty acid balance and fornix white matter integrity," Aging and Disease, 2017 8(4): p. 372-383.

Choi, G.H., et al., "Neuroprotective Effects and Physicochemical Characteristics of Milk Fortified with Fibroin BF-7," Korean J. Food Sci. Ani. Resour. vol. 28, No. 4, pp. 431-436 (2008).

Lee, J.Y. et al., "The Effect of BF-7 on the Ischemia-induced Learning and Memory Deficits," The Korean J. Anat. 38(2), 181-188, 2005.

Chae, H. et al., "The Role of BF-7 on Neuroprotection and Enhancement of Cognitive Function," Korean J Physiol Pharmacol, vol. 8:173-179, Aug. 2004.

Sreedhar, R. V. et al. "Unravelling a stearidonic acid rich triacylglycerol biosynthetic pathway in the developing seeds of Buglossoides arvensis: A transcriptomic landscape", Scientific Reports 7: 10473, 16 pages (Sep. 5, 2017).

Degan, D. et al., "The Role of Inflammation in Neurological Disorders", Curr. Pharm. Des. 24(14):1485-1501 (2018) [Abstract Only].

Morris, G. et al., "Leaky brain in neurological and psychiatric disorders: Drivers and consequences", Austr. New Zeal. J. Psychiat. 52(10):924-948 (2018).

Enache, D. et al., "Markers of central inflammation in major depressive disorder: A systematic review and meta-analysis of studies examining cerebrospinal fluid, positron emission tomography and post-mortem brain tissue", Brain Behav. Immun. 81:24-40 (2019).

Salter, M.W. et al., "Microglia emerge as central players in brain disease," Nat. Med. 23(9):1018-1027 (2017) [Abstract Only].

(56) References Cited

OTHER PUBLICATIONS

Kwon, H.S. et al., "Neuroinflammation in neurodegenerative disorders: the roles of microglia and astrocytes", Transl. Neurodegen. 9:42 (2020), 12 pages.

Kaur, N. et al., "Neuroinflammation Mechanisms and Phytotherapeutic Intervention: A Systematic Review", ACS Chem. Neurosci. 11:3707-3731 (2020) [Abstract Only].

Wong, C, "The Health Benefits of Ahiflower Oil", https://web.archive.org/web/20200405173646/https://www.verywellhealth.com/ahiflower-oil-benefits-and-uses-4147515 (2019), 12 pages [accessed Sep. 16, 2021].

| Subject ID | Test Date 1 | Test Date 2 | Days Between | Cognitive Flexibility SS 1 | SS 2 | % chg | Processing Speed SS 1 | SS 2 | % chg | Executive Function SS 1 | SS 2 | % chg | Motor Speed SS 1 | SS 2 | % chg |
|---|---|---|---|---|---|---|---|---|---|---|---|---|---|---|---|
| A | 7/6/18 | 11/1/18 | 118 | 93 | 98 | 5.38% | 95 | 99 | 4.21% | 92 | 97 | 5.43% | 88 | 97 | 10.23% |
| B | 7/2/18 | 9/5/18 | 65 | 102 | 106 | 3.92% | 122 | 126 | 3.28% | 101 | 105 | 3.96% | 105 | 118 | 12.38% |
| C | 6/21/18 | 12/22/18 | 184 | 104 | 106 | 1.92% | 90 | 114 | 26.67% | 103 | 106 | 2.91% | 65 | 78 | 20.00% |
| D | 6/22/18 | 9/1/18 | 71 | 105 | 108 | 2.86% | 86 | 99 | 15.12% | 104 | 107 | 2.88% | 114 | 124 | 8.77% |
| E | 1/13/19 | 2/23/19 | 41 | 105 | 93 | -11.43% | 88 | 93 | 5.68% | 105 | 109 | 3.81% | 109 | 129 | 18.35% |
| F | 2/2/19 | 3/6/19 | 32 | 112 | 114 | 1.79% | 94 | 110 | 17.02% | 111 | 113 | 1.80% | 123 | 136 | 10.57% |
| G | 1/11/19 | 2/16/19 | 36 | 99 | 100 | 1.01% | 74 | 117 | 58.11% | 99 | 99 | 0.00% | 59 | 83 | 40.68% |
| H | 1/11/19 | 2/22/19 | 42 | 104 | 106 | 1.92% | 97 | 106 | 9.28% | 105 | 107 | 1.90% | 85 | 94 | 10.59% |
| Average Scores | | | | 103.00 | 103.88 | | 93.25 | 108.00 | | 102.50 | 105.38 | | 93.50 | 107.38 | |
| Average Std Score Change Per Test | | | | | 0.98 | | | 16.59 | | | 3.23 | | | 15.61 | |
| Average % Std Score Change Per Test | | | | | | 0.92% | | | 17.42% | | | 2.84% | | | 16.45% |
| Min % Std Score Change Per Test | | | | | | -11.43% | | | 3.28% | | | 0.00% | | | 8.77% |
| Max % Std Score Change Per Test | | | | | | 5.38% | | | 58.11% | | | 5.43% | | | 40.68% |

FIG 14

BRAIN CNS VITAL SIGNS RESULTS in Healthy Adult Seniors

| Subject ID | Test Date 1 | Test Date 2 | Days Between | Birth Date | Age (yrs) | Verbal Memory SS 1 | Verbal Memory SS 2 | % chg | Psychomotor Speed SS 1 | Psychomotor Speed SS 2 | % chg | Reaction Time SS 1 | Reaction Time SS 2 | % chg |
|---|---|---|---|---|---|---|---|---|---|---|---|---|---|---|
| A | 7/6/18 | 11/1/18 | 118 | 8/28/50 | 69 | 97 | 124 | 27.84% | 88 | 97 | 10.23% | 98 | 106 | 8.16% |
| B | 7/2/18 | 9/5/18 | 65 | 1/1/50 | 70 | 121 | 130 | 7.44% | 113 | 125 | 10.62% | 93 | 99 | 6.45% |
| C | 6/21/18 | 12/22/18 | 184 | 1/1/60 | 60 | 118 | 127 | 7.63% | 69 | 90 | 30.43% | 96 | 96 | 0.00% |
| D | 6/22/18 | 9/1/18 | 71 | 5/5/47 | 72 | 104 | 118 | 13.46% | 100 | 116 | 16.00% | 82 | 106 | 29.27% |
| E | 1/13/19 | 2/23/19 | 41 | 10/21/40 | 79 | 107 | 126 | 17.76% | 98 | 116 | 18.37% | 105 | 115 | 9.52% |
| F | 2/2/19 | 3/6/19 | 32 | 9/18/47 | 72 | 98 | 101 | 3.06% | 113 | 132 | 16.81% | 105 | 111 | 5.71% |
| G | 1/11/19 | 2/16/19 | 36 | 10/29/46 | 73 | 82 | 129 | 57.32% | 57 | 96 | 68.42% | 93 | 105 | 12.90% |
| H | 1/11/19 | 2/22/19 | 42 | 9/21/51 | 68 | 87 | 115 | 32.18% | 88 | 99 | 12.50% | 95 | 98 | 3.16% |
| Average Scores | | | | | 70.36 | 101.75 | 121.25 | | 90.75 | 108.88 | | 95.88 | 104.50 | |
| Average Std Score Change Per Test | | | | | | | 21.94 | | | 20.39 | | | 9.70 | |
| Average % Std Score Change Per Test | | | | | | | | 20.84% | | | 22.92% | | | 9.40% |
| Min % Std Score Change Per Test | | | | | | | | 3.06% | | | 10.23% | | | 0.00% |
| Max % Std Score Change Per Test | | | | | | | | 57.32% | | | 68.42% | | | 29.27% |

FIG. 14 (cont.)

| BRAINI CNS VITAL SIGNS (MS SUBJECT) MS Subject A | Test Date 1 | Verbal Memory Std Scores | Psychomotor Speed Std Scores | Reaction Time Std Scores | Cognitive Flexibility Std Scores | Processing Speed Std Scores | Executive Function Std Scores | Motor Speed Std Scores |
|---|---|---|---|---|---|---|---|---|
| Baseline | 7/16/18 | LG 109 | R 59 | Y 85 | R 31 | R 59 | R 33 | O 73 |
| ON Braini | 2/17/19 | O 77 | R 61 | LG 92 | R 44 | O 75 | R 44 | R 67 |
| | 3/6/19 | LG 96 | R 69 | LG 97 | Y 86 | Y 81 | Y 87 | O 73 |
| | 3/23/19 | LG 106 | O 75 | LG 104 | Y 86 | Y 83 | Y 88 | O 79 |
| | 4/7/19 | LG 99 | O 76 | LG 96 | O 78 | LG 94 | Y 80 | O 74 |
| | 5/8/19 | DG 115 | O 74 | DG 119 | Y 89 | Y 87 | Y 88 | O 74 |
| OFF Braini | 6/18/19 | DG 115 | O 75 | LG 99 | O 71 | Y 83 | O 72 | O 79 |
| | 7/2/19 | DG 112 | O 71 | LG 106 | O 79 | Y 85 | Y 81 | O 73 |
| ON Braini | 8/2/19 | DG 112 | Y 84 | LG 92 | O 75 | LG 92 | O 78 | Y 86 |
| | 8/31/19 | DG 115 | Y 81 | LG 100 | LG 99 | LG 94 | LG 100 | Y 80 |
| | Test Date % change | % change | % change | % change | % change | % change | % change | % change |
| Baseline | 7/16/18 | | | | | | | |
| ON Braini | 1/17/19 | | | | | | | |
| | 2/17/19 | Y -29.36% | Y 3.39% | Y 8.24% | Y 41.94% | Y 27.12% | Y 33.33% | Y -8.22% |
| | 3/6/19 | Y 24.68% | Y 13.11% | Y 5.43% | Y 95.45% | Y 8.00% | Y 97.73% | Y 8.96% |
| | 3/23/19 | Y 10.42% | Y 8.70% | Y 7.22% | Y 0.00% | Y 2.47% | Y 1.15% | Y 8.22% |
| | 4/7/19 | -6.60% | 1.33% | -7.69% | -9.30% | 13.25% | -9.09% | -6.33% |
| | 5/8/19 | 16.16% | -2.63% | 23.96% | 14.10% | -7.45% | 10.00% | 0.00% |
| Accum % Change On Braini | | 5.50% | 25.42% | 40.00% | 187.10% | 47.46% | 166.67% | 1.37% |
| OFF Braini | 6/18/19 | Y 0.00% | Y 1.35% | Y -16.81% | Y -20.22% | Y -4.60% | Y -18.18% | Y 6.76% |
| | 7/2/19 | Y -2.61% | Y -5.33% | Y 7.07% | Y 11.27% | Y 2.41% | Y 12.50% | Y -7.59% |
| Accum % Change On Braini | | 2.75% | 20.34% | 24.71% | 154.84% | 44.07% | 145.45% | 0.00% |
| ON Braini | 8/2/19 | LG 0.00% | LG 18.31% | LG -13.21% | LG -5.06% | LG 8.24% | LG -3.70% | LG 17.81% |
| | 8/31/19 | LG 2.68% | LG -3.57% | LG 8.70% | LG 32.00% | LG 2.17% | LG 28.21% | LG -6.98% |
| Accum % Change On Braini | | 5.50% | 37.29% | 17.65% | 219.35% | 59.32% | 203.03% | 9.59% |

FIG. 15

PHYSICIAN'S OBSERVATIONAL TRIAL SUMMARY DATA AFTER BRAINI® ADMINISTRATION IN DYSLEXIC SUBJECTS

BRAINI CNS VITAL SIGNS (Dyslexic Subjects)

| Subject | Age | Verbal Memory | | | Psychomotor Speed | | | Reaction Time | | |
|---|---|---|---|---|---|---|---|---|---|---|
| | | SS1 | SS2 | % chg | SS1 | SS2 | % chg | SS1 | SS2 | % chg |
| A | 23 | 108 | 75 | -30.56% | 86 | 89 | 3.49% | 50 | 63 | 26.00% |
| B | 60 | 109 | 106 | -2.75% | 59 | 75 | 27.12% | 85 | 104 | 22.35% |
| C | 63 | 87 | 90 | 3.45% | 107 | 114 | 6.54% | 84 | 96 | 14.29% |

| Subject | Cognitive Flexibility | | | Processing Speed | | | Executive Function | | | Motor Speed | | |
|---|---|---|---|---|---|---|---|---|---|---|---|---|
| | SS1 | SS2 | % chg | SS1 | SS2 | % chg | SS1 | SS2 | % chg | SS1 | SS2 | % chg |
| A | 30 | 86 | 186.67% | 84 | 104 | 23.81% | 31 | 85 | 174.19% | 92 | 84 | -8.70% |
| B | 31 | 86 | 177.42% | 59 | 83 | 40.68% | 33 | 88 | 166.67% | 73 | 79 | 8.22% |
| C | 38 | 92 | 142.11% | 105 | 113 | 7.62% | 37 | 92 | 148.65% | 108 | 111 | 2.78% |

FIG. 16A

PHYSICIAN'S OBSERVATIONAL TRIAL SUMMARY DATA AFTER BRAINI® ADMINISTRATION IN DYSLEXIC SUBJECTS

Changes in Key CNS Vital Signs Parameters in Dyslexic Subjects after Braini® (30 days)

| Subject | Percent Improvements in Standard Scores | | |
|---|---|---|---|
| | Cognitive Flexibility | Executive Function | Reaction Time |
| A | 186.67% | 174.19% | 26.00% |
| B | 177.42% | 166.67% | 22.35% |
| C | 142.11% | 148.65% | 13.10% |
| D | 28.40% | 25.00% | 16.95% |
| E | 16.00% | 18.92% | 33.33% |
| F | 23.94% | 25.71% | 8.60% |
| AVERAGE | 95.76% | 93.19% | 20.06% |

Changes in Age-Normed Standard Scores

| | Subject A | Subject B | Subject C | Subject D | Subject E | Subject F |
|---|---|---|---|---|---|---|
| Cognitive Flexibility | | | | | | |
| Start | 30 | 33 | 37 | 81 | 75 | 71 |
| End | 85 | 88 | 92 | 104 | 87 | 88 |
| Executive Function | | | | | | |
| Start | 30 | 33 | 37 | 84 | 74 | 70 |
| End | 85 | 88 | 92 | 105 | 88 | 88 |
| Reaction Time | | | | | | |
| Start | 50 | 85 | 84 | 59 | 63 | 93 |
| End | 63 | 104 | 95 | 69 | 84 | 101 |

FIG. 16B

BRAINI CNS VITAL SIGNS (PEPTYLIN --> BRAINI®)

| | | Verbal Memory | | | | | | Psychomotor Speed | | | | |
|---|---|---|---|---|---|---|---|---|---|---|---|---|
| Subject | Age | SS1 | SS2 | SS3 | % chg 1 | % chg 2 | | SS1 | SS2 | SS3 | % chg 1 | % chg 2 |
| A | 63 | 81 | 109 | 103 | 0.34567901 | -0.0550459 | | 107 | 104 | 112 | -0.0280374 | 0.07692308 |
| B | 67 | 100 | 106 | 94 | 0.06 | -0.1132075 | | 111 | 121 | 123 | 0.09009009 | 0.01652893 |
| C | 71 | 112 | 126 | 121 | 0.125 | -0.0396825 | | 135 | 123 | 114 | -0.08888890 | -0.0731707 |
| | | | | Avg % | 17.69% | -6.93% | | | | | -0.89% | 0.68% |

| | | Reaction Time | | | | | | Cognitive Flexibility | | | | |
|---|---|---|---|---|---|---|---|---|---|---|---|---|
| Subject | Age | SS1 | SS2 | SS3 | % chg 1 | % chg 2 | | SS1 | SS2 | SS3 | % chg 1 | % chg 2 |
| A | 63 | 106 | 105 | 113 | -0.009434 | 0.07619048 | | 95 | 96 | 112 | 0.01052632 | 0.16666667 |
| B | 67 | 98 | 107 | 107 | 0.09183673 | 0 | | 118 | 105 | 123 | -0.1101695 | 0.17142857 |
| C | 71 | 108 | 118 | 112 | 0.09259259 | -0.0508475 | | 107 | 78 | 101 | -0.271028 | 0.29487179 |
| | | | | Avg % | 5.83% | 0.84% | | | | | -12.36% | 21.10% |

| | | Processing Speed | | | | | | Executive Function | | | | |
|---|---|---|---|---|---|---|---|---|---|---|---|---|
| Subject | Age | SS1 | SS2 | SS3 | % chg 1 | % chg 2 | | SS1 | SS2 | SS3 | % chg 1 | % chg 2 |
| A | 63 | 111 | 109 | 117 | -0.018018 | 0.0733945 | | 94 | 94 | 111 | 0 | 0.18085106 |
| B | 67 | 111 | 118 | 118 | 0.06306306 | 0 | | 117 | 103 | 122 | -0.11196581 | 0.18446602 |
| C | 71 | 147 | 139 | 120 | -0.0544218 | -0.1366906 | | 107 | 77 | 101 | -0.2803738 | 0.31168831 |
| | | | | Avg % | -0.31% | -2.11% | | | | | -13.33% | 22.57% |

| | | Motor Speed | | | | |
|---|---|---|---|---|---|---|
| Subject | Age | SS1 | SS2 | SS3 | % chg 1 | % chg 2 |
| A | 63 | 104 | 100 | 106 | -0.0384615 | 0.06 |
| B | 67 | 108 | 119 | 122 | 0.10185185 | 0.02521008 |
| C | 71 | 109 | 100 | 104 | -0.0825688 | 0.04 |
| | | | | Avg % | -0.64% | 4.17% |

FIG 17

| AVG TOTAL | # POS | 75.58% | # POS | 35 | | |
|---|---|---|---|---|---|---|
| AVG TOTAL | # NEG | 18.99% | # NEG | 5 | | |
| AVG TOTAL | # ZERO | 5.43% | # ZERO | 3 | | |
| | | | | 43 | | |

FIG. 18

PHYSICIAN'S OBSERVATION DATA BEFORE AND AFTER BRAINI® ADMINISTRATION – PSYCHOMOTOR SPEED

| Subject ID # (Birth Year) | Test Dates | Test Times | Psychomotor Speed (Raw Subject Score) | Psychomotor Speed (Standard Score) | Psychomotor Speed (CHANGE) | Psychomotor Speed (% CHANGE) | Psychomotor Speed (Subject Percentile Rank) |
|---|---|---|---|---|---|---|---|
| 1 (1952) | 7/9/2019 | 19:28:24 | 185 | 121 | | | 92 |
| | 6/2/2019 | 13:49:44 | 170 | 111 | 10 | 9.01% | 77 |
| 2 (1941) | 9/3/2019 | 19:24:56 | 161 | 121 | | | 92 |
| | 7/13/2019 | 15:24:02 | 128 | 96 | 25 | 26.04% | 40 |
| 3 (1950) | 11/1/2018 | 9:55:54 | 147 | 97 | | | 42 |
| | 7/6/2018 | 13:05:18 | 134 | 88 | 9 | 10.23% | 21 |
| 4 (1991) | 6/8/2020 | 12:21:51 | 212 | 118 | | | 88 |
| | 4/10/2020 | 10:27:46 | 193 | 105 | 13 | 12.38% | 63 |
| 5 (1988) | 5/27/2020 | 11:18:15 | 205 | 118 | | | 88 |
| | 4/11/2020 | 6:39:29 | 183 | 103 | 15 | 14.56% | 58 |
| 6 (1950) | 9/5/2018 | 8:50:56 | 191 | 125 | | | 95 |
| | 7/2/2018 | 14:03:16 | 173 | 113 | 12 | 10.62% | 81 |
| 7 (1990) | 8/11/2020 | 18:11:21 | 160 | 88 | | | 21 |
| | 8/5/2020 | 16:47:13 | 147 | 79 | 9 | 11.39% | 8 |
| 8 (1989) | 4/13/2020 | 18:52:39 | 192 | 109 | | | 73 |
| | 2/21/2020 | 20:56:35 | 176 | 99 | 10 | 10.10% | 47 |
| 9 (1960) | 7/18/2020 | 10:42:48 | 167 | 103 | | | 58 |
| | 5/31/2020 | 11:12:59 | 160 | 98 | 5 | 5.10% | 45 |
| 10 (1961) | 6/1/2020 | 14:58:22 | 181 | 115 | | | 84 |
| | 4/10/2020 | 14:11:31 | 175 | 110 | 5 | 4.55% | 75 |
| 11 (1991) | 5/28/2020 | 8:17:00 | 161 | 84 | | | 14 |
| | 4/10/2020 | 13:47:18 | 130 | 64 | 20 | 31.25% | 1 |
| 12 (2009) | 3/8/2020 | 20:39:44 | 143 | 93 | | | 32 |
| | 2/3/2020 | 19:42:18 | 138 | 90 | 3 | 3.33% | 25 |
| 13 (1986) | 6/4/2020 | 1:57:36 | 163 | 90 | | | 25 |

FIG. 18 (cont.)

|  |  |  |  |  |  |  |  |
|---|---|---|---|---|---|---|---|
|  | 4/30/2020 | 1:53:30 | 143 | 77 | 13 | 16.88% | 6 |
| 14 (1947) | 9/1/2018 | 14:31:43 | 154 | 116 |  |  | 86 |
|  | 6/22/2018 | 12:20:17 | 133 | 100 | 16 | 16.00% | 50 |
| 15 (1976) | 9/4/2018 | 10:39:04 | 174 | 101 |  |  | 53 |
|  | 7/4/2018 | 14:49:22 | 154 | 85 | 16 | 18.82% | 16 |
| 16 (1993) | 5/5/2020 | 15:43:39 | 222 | 124 |  |  | 95 |
|  | 4/13/2020 | 12:07:17 | 220 | 123 | 1 | 0.81% | 94 |
| 17 (1938) | 6/27/2018 | 14:20:36 | 105 | 93 |  |  | 32 |
|  | 4/25/2018 | 16:31:24 | 130 | 108 | -15 | -13.89% | 70 |
| 18 (1968) | 5/22/2020 | 14:34:27 | 201 | 132 |  |  | 98 |
|  | 4/19/2020 | 20:57:38 | 169 | 105 | 27 | 25.71% | 63 |
| 19 (1991) | 7/22/2020 | 17:27:25 | 198 | 109 |  |  | 73 |
|  | 6/9/2020 | 20:23:45 | 205 | 113 | -4 | -3.54% | 81 |
| 20 (1990) | 9/20/2019 | 10:52:36 | 196 | 107 |  |  | 68 |
|  | 8/26/2019 | 22:50:57 | 196 | 107 | 0 | 0.00% | 68 |
| 21 (1991) | 7/30/2020 | 20:06:52 | 224 | 125 |  |  | 95 |
|  | 6/21/2020 | 11:08:15 | 214 | 119 | 6 | 5.04% | 90 |
| 22 (1951) | 7/25/2019 | 15:36:31 | 146 | 96 |  |  | 40 |
|  | 2/26/2019 | 9:34:39 | 124 | 82 | 14 | 17.07% | 12 |
| 23 (1983) | 9/15/2020 | 20:59:09 | 187 | 106 |  |  | 66 |
|  | 8/3/2020 | 20:45:00 | 183 | 103 | 3 | 2.91% | 58 |
| 24 (1962) | 3/3/2020 | 10:38:07 | 172 | 108 |  |  | 70 |
|  | 1/30/2020 | 19:32:48 | 152 | 91 | 17 | 18.68% | 27 |
| 25 (1985) | 6/3/2020 | 10:25:29 | 183 | 103 |  |  | 58 |
|  | 4/29/2020 | 9:59:48 | 180 | 101 | 2 | 1.98% | 53 |
| 26 (1956) | 9/12/2019 | 21:45:42 | 172 | 112 |  |  | 79 |
|  | 7/24/2019 | 21:55:56 | 159 | 104 | 8 | 7.69% | 61 |
| 27 (1940) | 2/23/2019 | 13:03:37 | 155 | 116 |  |  | 86 |
|  | 1/13/2019 | 8:12:07 | 131 | 98 | 18 | 18.37% | 45 |
| 28 (1988) | 4/27/2020 | 11:39:24 | 220 | 128 |  |  | 97 |
|  | 3/9/2020 | 18:13:15 | 213 | 123 | 5 | 4.07% | 94 |
| 29 (1973) | 8/16/2020 | 18:11:56 | 170 | 98 |  |  | 45 |
|  | 6/25/2020 | 18:33:10 | 161 | 91 | 7 | 7.69% | 27 |

FIG. 18 (cont.)

| | 6 SCORE | TOTAL AVG | | | | | % Chg | |
|---|---|---|---|---|---|---|---|---|
| 30 (1950) | 5/4/2020 | 12:24:12 | 142 | 93 | | | | 32 |
| | 4/8/2020 | 14:57:33 | 144 | 95 | -2 | -2.11% | 37 |
| 31 (1999) | 5/22/2020 | 18:05:34 | 182 | 98 | | | 45 |
| | 4/9/2020 | 21:16:34 | 182 | 98 | 0 | 0.00% | 45 |
| 32 (1948) | 9/26/2018 | 17:36:00 | 135 | 101 | | | 53 |
| | 6/27/2018 | 14:17:30 | 130 | 97 | 4 | 4.12% | 42 |
| 33 (1959) | 9/1/2020 | 9:30:18 | 184 | 120 | | | 91 |
| | 7/15/2020 | 10:43:15 | 184 | 120 | 0 | 0.00% | 91 |
| 34 (1989) | 6/1/2020 | 11:27:43 | 194 | 111 | | | 77 |
| | 4/27/2020 | 10:26:06 | 189 | 107 | 4 | 3.74% | 68 |
| 35 (1948) | 9/6/2019 | 9:28:37 | 152 | 114 | | | 82 |
| | 5/30/2019 | 14:03:09 | 179 | 135 | -21 | -15.56% | 99 |
| 36 (1946) | 2/16/2019 | 14:44:47 | 128 | 96 | | | 40 |
| | 1/11/2019 | 17:42:18 | 78 | 57 | 39 | 68.42% | 1 |
| 37 (1972) | 6/5/2020 | 13:27:08 | 200 | 121 | | | 92 |
| | 4/27/2020 | 12:00:26 | 186 | 110 | 11 | 10.00% | 75 |
| 38 (1951) | 5/4/2020 | 16:55:39 | 139 | 91 | | | 27 |
| | 4/17/2020 | 12:08:56 | 149 | 98 | -7 | -7.14% | 45 |
| 39 (1959) | 5/6/2020 | 6:45:43 | 212 | 138 | | | 99 |
| | 1/29/2018 | 10:27:02 | 176 | 111 | 27 | 24.32% | 77 |
| 40 (1951) | 2/22/2019 | 21:50:15 | 151 | 99 | | | 47 |
| | 1/11/2019 | 11:06:11 | 133 | 88 | 11 | 12.50% | 21 |
| 41 (1978) | 6/29/2020 | 17:19:21 | 157 | 88 | | | 21 |
| | 5/18/2020 | 11:28:02 | 146 | 79 | 9 | 11.39% | 8 |
| 42 (1953) | 3/1/2020 | 7:24:34 | 166 | 109 | | | 73 |
| | 6/13/2019 | 8:48:51 | 159 | 104 | 5 | 4.81% | 61 |
| 43 (1962) | 10/15/2019 | 10:35:51 | 109 | 54 | | | 1 |
| | 8/29/2019 | 0:27:14 | 76 | 26 | 28 | 107.69% | 1 |
| | | | | MIN | -21 | | |
| | | | | MAX | 39 | | |
| | | | | AVG | 8.79 | 11.98% | |

FIG. 18 (cont.)

| | # POS | 35 | | | | | | |
|---|---|---|---|---|---|---|---|---|
| | # NEG | 6 | | | | | | |
| | # ZERO | 2 | | | | | | |
| | | 43 | | | | | | |

FIG. 19

PHYSICIAN'S OBSERVATION DATA BEFORE AND AFTER BRAINI® ADMINISTRATION – REACTION TIME

| Subject ID # (Birth Year) | Test Dates | Test Times | Reaction Time (Raw Subject Score) | Reaction Time (Standard Score) | Reaction Time (CHANGE) | Reaction Time (% CHANGE) | Reaction Time (Subject Percentile Rank) |
|---|---|---|---|---|---|---|---|
| 1 (1952) | 7/9/2019 | 19:28:24 | 641 | 107 | | | 68 |
| | 6/2/2019 | 13:49:44 | 719 | 98 | 9 | 9.18% | 45 |
| 2 (1941) | 9/3/2019 | 19:24:56 | 806 | 96 | | | 40 |
| | 7/13/2019 | 15:24:02 | 715 | 106 | -10 | -9.43% | 66 |
| 3 (1950) | 11/1/2018 | 9:55:54 | 654 | 106 | | | 66 |
| | 7/6/2018 | 13:05:18 | 723 | 98 | 8 | 8.16% | 45 |
| 4 (1991) | 6/8/2020 | 12:21:51 | 650 | 90 | | | 25 |
| | 4/10/2020 | 10:27:46 | 693 | 83 | 7 | 8.43% | 13 |
| 5 (1988) | 5/27/2020 | 11:18:15 | 558 | 110 | | | 75 |
| | 4/11/2020 | 6:39:29 | 662 | 91 | 19 | 20.88% | 27 |
| 6 (1950) | 9/5/2018 | 8:50:56 | 714 | 99 | | | 47 |
| | 7/2/2018 | 14:03:16 | 766 | 93 | 6 | 6.45% | 32 |
| 7 (1990) | 8/11/2020 | 18:11:21 | 540 | 113 | | | 81 |
| | 8/5/2020 | 16:47:13 | 600 | 102 | 11 | 10.78% | 55 |
| 8 (1989) | 4/13/2020 | 18:52:39 | 622 | 98 | | | 45 |
| | 2/21/2020 | 20:56:35 | 566 | 108 | -10 | -9.26% | 70 |
| 9 (1960) | 7/18/2020 | 10:42:48 | 660 | 102 | | | 55 |
| | 5/31/2020 | 11:12:59 | 726 | 91 | 11 | 12.09% | 27 |
| 10 (1961) | 6/1/2020 | 14:58:22 | 614 | 109 | | | 73 |
| | 4/10/2020 | 14:11:31 | 646 | 104 | 5 | 4.81% | 61 |
| 11 (1991) | 5/28/2020 | 8:17:00 | 703 | 81 | | | 10 |
| | 4/10/2020 | 13:47:18 | 835 | 58 | 23 | 39.66% | 1 |
| 12 (2009) | 3/8/2020 | 20:39:44 | 806 | 84 | | | 14 |
| | 2/3/2020 | 19:42:18 | 952 | 63 | 21 | 33.33% | 1 |
| 13 (1986) | 6/4/2020 | 1:57:36 | 629 | 97 | | | 42 |

FIG. 19 (cont.)

| | | | | | | | |
|---|---|---|---|---|---|---|---|
| 14 (1947) | 4/30/2020 | 1:53:30 | 737 | 78 | 19 | 24.36% | 7 |
| | 9/1/2018 | 14:31:43 | 719 | 106 | | | 66 |
| 15 (1976) | 6/22/2018 | 12:20:17 | 940 | 82 | 24 | 29.27% | 12 |
| | 9/4/2018 | 10:39:04 | 573 | 112 | | | 79 |
| | 7/4/2018 | 14:49:22 | 571 | 112 | 0 | 0.00% | 79 |
| 16 (1993) | 5/5/2020 | 15:43:39 | 572 | 104 | | | 61 |
| | 4/13/2020 | 12:07:17 | 577 | 103 | 1 | 0.97% | 58 |
| 17 (1938) | 6/27/2018 | 14:20:36 | 856 | 101 | | | 53 |
| | 4/25/2018 | 16:31:24 | 1084 | 76 | 25 | 32.89% | 5 |
| 18 (1968) | 5/22/2020 | 14:34:27 | 788 | 81 | | | 10 |
| | 4/19/2020 | 20:57:38 | 809 | 78 | 3 | 3.85% | 7 |
| 19 (1991) | 7/22/2020 | 17:27:25 | 674 | 86 | | | 18 |
| | 6/9/2020 | 20:23:45 | 618 | 96 | -10 | -10.42% | 40 |
| 20 (1990) | 9/20/2019 | 10:52:36 | 724 | 77 | | | 6 |
| | 8/26/2019 | 22:50:57 | 658 | 89 | -12 | -13.48% | 23 |
| 21 (1991) | 7/30/2020 | 20:06:52 | 752 | 72 | | | 3 |
| | 6/21/2020 | 11:08:15 | 784 | 67 | 5 | 7.46% | 1 |
| 22 (1951) | 7/25/2019 | 15:36:31 | 654 | 106 | | | 66 |
| | 2/26/2019 | 9:34:39 | 678 | 103 | 3 | 2.91% | 58 |
| 23 (1983) | 9/15/2020 | 20:59:09 | 604 | 101 | | | 53 |
| | 8/3/2020 | 20:45:00 | 765 | 73 | 28 | 38.36% | 4 |
| 24 (1962) | 3/3/2020 | 10:38:07 | 663 | 101 | | | 53 |
| | 1/30/2020 | 19:32:48 | 715 | 93 | 8 | 8.60% | 32 |
| 25 (1985) | 6/3/2020 | 10:25:29 | 658 | 92 | | | 30 |
| | 4/29/2020 | 9:59:48 | 653 | 93 | -1 | -1.08% | 32 |
| 26 (1956) | 9/12/2019 | 21:45:42 | 589 | 113 | | | 81 |
| | 7/24/2019 | 21:55:56 | 656 | 105 | 8 | 7.62% | 63 |
| 27 (1940) | 2/23/2019 | 13:03:37 | 631 | 115 | | | 84 |
| | 1/13/2019 | 8:12:07 | 721 | 105 | 10 | 9.52% | 63 |
| 28 (1988) | 4/27/2020 | 11:39:24 | 566 | 108 | | | 70 |
| | 3/9/2020 | 18:13:15 | 680 | 88 | 20 | 22.73% | 21 |
| 29 (1973) | 8/16/2020 | 18:11:56 | 744 | 83 | | | 13 |
| | 6/25/2020 | 18:33:10 | 809 | 72 | 11 | 15.28% | 3 |

FIG. 19 (cont.)

| | | | | | | | |
|---|---|---|---|---|---|---|---|
| 30 (1950) | 5/4/2020 | 12:24:12 | 821 | 87 | | | 19 |
| | 4/8/2020 | 14:57:33 | 929 | 74 | 13 | 17.57% | 4 |
| 31 (1999) | 5/22/2020 | 18:05:34 | 702 | 81 | | | 10 |
| | 4/9/2020 | 21:16:34 | 725 | 77 | 4 | 5.19% | 6 |
| 32 (1948) | 9/26/2018 | 17:36:00 | 891 | 87 | | | 19 |
| | 6/27/2018 | 14:17:30 | 895 | 87 | 0 | 0.00% | 19 |
| 33 (1959) | 9/1/2020 | 9:30:18 | 608 | 111 | | | 77 |
| | 7/15/2020 | 10:43:15 | 552 | 117 | -6 | -5.13% | 87 |
| 34 (1989) | 6/1/2020 | 11:27:43 | 620 | 99 | | | 47 |
| | 4/27/2020 | 10:26:06 | 668 | 90 | 9 | 10.00% | 25 |
| 35 (1948) | 9/6/2019 | 9:28:37 | 658 | 112 | | | 79 |
| | 5/30/2019 | 14:03:09 | 699 | 108 | 4 | 3.70% | 70 |
| 36 (1946) | 2/16/2019 | 14:44:47 | 728 | 105 | | | 63 |
| | 1/11/2019 | 17:42:18 | 837 | 93 | 12 | 12.90% | 32 |
| 37 (1972) | 6/5/2020 | 13:27:08 | 669 | 95 | | | 37 |
| | 4/27/2020 | 12:00:26 | 690 | 92 | 3 | 3.26% | 30 |
| 38 (1951) | 5/4/2020 | 16:55:39 | 740 | 96 | | | 40 |
| | 4/17/2020 | 12:08:56 | 865 | 82 | 14 | 17.07% | 12 |
| 39 (1959) | 5/6/2020 | 6:45:43 | 686 | 102 | | | 55 |
| | 1/29/2018 | 10:27:02 | 698 | 96 | 6 | 6.25% | 40 |
| 40 (1951) | 2/22/2019 | 21:50:15 | 721 | 98 | | | 45 |
| | 1/11/2019 | 11:06:11 | 747 | 95 | 3 | 3.16% | 37 |
| 41 (1978) | 6/29/2020 | 17:19:21 | 598 | 108 | | | 70 |
| | 5/18/2020 | 11:28:02 | 723 | 86 | 22 | 25.58% | 18 |
| 42 (1953) | 3/1/2020 | 7:24:34 | 675 | 103 | | | 58 |
| | 6/13/2019 | 8:48:51 | 684 | 102 | 1 | 0.98% | 55 |
| 43 (1962) | 10/15/2019 | 10:35:51 | 696 | 96 | | | 40 |
| | 8/29/2019 | 0:27:14 | 835 | 74 | 22 | 29.73% | 4 |
| | | | | MIN | -12 | | |
| | | | | MAX | 28 | | |
| | 6 SCORE | TOTAL AVG | | AVG | 8.12 | 10.33% | |

FIG. 19 (cont.)

| | AVG TOTAL | # POS | | | | # POS | 31 | | | | |
|---|---|---|---|---|---|---|---|---|---|---|---|
| | AVG TOTAL | # NEG | | | | # NEG | 11 | | | | |
| | AVG TOTAL | # ZERO | | | | # ZERO | 1 | | | | |
| | | | | | | | 43 | | | | |
| | | | | | | | | | | | |
| | | | | | | | | | | | |
| | | | | | | | | | | | |
| | | | | | | | | | | | |

FIG. 20

PHYSICIAN'S OBSERVATION DATA BEFORE AND AFTER BRAINI® ADMINISTRATION – COGNITIVE FLEXIBILITY

| Subject ID # (Birth Year) | Test Dates | Test Times | Cognitive Flexibility (Raw Subject Score) | Cognitive Flexibility (Standard Score) | Cognitive Flexibility (CHANGE) | Cognitive Flexibility (% CHANGE) | Cognitive Flexibility (Subject Percentile Rank) |
|---|---|---|---|---|---|---|---|
| 1 (1952) | 7/9/2019 | 19:28:24 | 42 | 105 | | | 63 |
| | 6/2/2019 | 13:49:44 | 57 | 118 | -13 | -11.02% | 88 |
| 2 (1941) | 9/3/2019 | 19:24:56 | 44 | 112 | | | 79 |
| | 7/13/2019 | 15:24:02 | 46 | 113 | -1 | -0.88% | 81 |
| 3 (1950) | 11/1/2018 | 9:55:54 | 34 | 98 | | | 45 |
| | 7/6/2018 | 13:05:18 | 29 | 93 | 5 | 5.38% | 32 |
| 4 (1991) | 6/8/2020 | 12:21:51 | 54 | 106 | | | 66 |
| | 4/10/2020 | 10:27:46 | 43 | 89 | 17 | 19.10% | 23 |
| 5 (1988) | 5/27/2020 | 11:18:15 | 35 | 79 | | | 8 |
| | 4/11/2020 | 6:39:29 | 26 | 65 | 14 | 21.54% | 1 |
| 6 (1950) | 9/5/2018 | 8:50:56 | 43 | 106 | | | 66 |
| | 7/2/2018 | 14:03:16 | 39 | 102 | 4 | 3.92% | 55 |
| 7 (1990) | 8/11/2020 | 18:11:21 | 40 | 87 | | | 19 |
| | 8/5/2020 | 16:47:13 | 31 | 73 | 14 | 19.18% | 4 |
| 8 (1989) | 4/13/2020 | 18:52:39 | 51 | 103 | | | 58 |
| | 2/21/2020 | 20:56:35 | 47 | 97 | 6 | 6.19% | 42 |
| 9 (1960) | 7/18/2020 | 10:42:48 | 50 | 108 | | | 70 |
| | 5/31/2020 | 11:12:59 | 39 | 93 | 15 | 16.13% | 32 |
| 10 (1961) | 6/1/2020 | 14:58:22 | 55 | 115 | | | 84 |
| | 4/10/2020 | 14:11:31 | 47 | 104 | 11 | 10.58% | 61 |
| 11 (1991) | 5/28/2020 | 8:17:00 | 53 | 105 | | | 63 |
| | 4/10/2020 | 13:47:18 | 36 | 79 | 26 | 32.91% | 8 |
| 12 (2009) | 3/8/2020 | 20:39:44 | 14 | 87 | | | 19 |
| | 2/3/2020 | 19:42:18 | 0 | 75 | 12 | 16.00% | 5 |
| 13 (1986) | 6/4/2020 | 1:57:36 | 52 | 105 | | | 63 |

FIG. 20 (cont.)

| | | | | | | | | |
|---|---|---|---|---|---|---|---|---|
| 14 (1947) | 4/30/2020 | 1:53:30 | 33 | 76 | 29 | 38.16% | 5 | |
| | 9/1/2018 | 14:31:43 | 39 | 108 | | | 70 | |
| 15 (1976) | 6/22/2018 | 12:20:17 | 34 | 105 | 3 | 2.86% | 63 | |
| | 9/4/2018 | 10:39:04 | 51 | 108 | | | 70 | |
| | 7/4/2018 | 14:49:22 | 37 | 91 | 17 | 18.68% | 27 | |
| 16 (1993) | 5/5/2020 | 15:43:39 | 61 | 117 | | | 87 | |
| | 4/13/2020 | 12:07:17 | 55 | 108 | 9 | 8.33% | 70 | |
| 17 (1938) | 6/27/2018 | 14:20:36 | 11 | 93 | | | 32 | |
| | 4/25/2018 | 16:31:24 | -2 | 84 | 9 | 10.71% | 14 | |
| 18 (1968) | 5/22/2020 | 14:34:27 | 41 | 96 | | | 40 | |
| | 4/19/2020 | 20:57:38 | 30 | 81 | 15 | 18.52% | 10 | |
| 19 (1991) | 7/22/2020 | 17:27:25 | 57 | 111 | | | 77 | |
| | 6/9/2020 | 20:23:45 | 42 | 88 | 23 | 26.14% | 21 | |
| 20 (1990) | 9/20/2019 | 10:52:36 | 40 | 85 | | | 16 | |
| | 8/26/2019 | 22:50:57 | 38 | 82 | 3 | 3.66% | 12 | |
| 21 (1991) | 7/30/2020 | 20:06:52 | 49 | 99 | | | 47 | |
| | 6/21/2020 | 11:08:15 | 42 | 88 | 11 | 12.50% | 21 | |
| 22 (1951) | 7/25/2019 | 15:36:31 | 54 | 115 | | | 84 | |
| | 2/26/2019 | 9:34:39 | 54 | 115 | 0 | 0.00% | 84 | |
| 23 (1983) | 9/15/2020 | 20:59:09 | 61 | 118 | | | 88 | |
| | 8/3/2020 | 20:45:00 | 54 | 108 | 10 | 9.26% | 70 | |
| 24 (1962) | 3/3/2020 | 10:38:07 | 35 | 88 | | | 21 | |
| | 1/30/2020 | 19:32:48 | 23 | 71 | 17 | 23.94% | 3 | |
| 25 (1985) | 6/3/2020 | 10:25:29 | 53 | 106 | | | 66 | |
| | 4/29/2020 | 9:59:48 | 54 | 108 | -2 | -1.85% | 70 | |
| 26 (1956) | 9/12/2019 | 21:45:42 | 50 | 112 | | | 79 | |
| | 7/24/2019 | 21:55:56 | 32 | 96 | 16 | 16.67% | 40 | |
| 27 (1940) | 2/23/2019 | 13:03:37 | 17 | 93 | | | 32 | |
| | 1/13/2019 | 8:12:07 | 35 | 105 | -12 | -11.43% | 63 | |
| 28 (1988) | 4/27/2020 | 11:39:24 | 60 | 117 | | | 87 | |
| | 3/9/2020 | 18:13:15 | 55 | 109 | 8 | 7.34% | 73 | |
| 29 (1973) | 8/16/2020 | 18:11:56 | 47 | 103 | | | 58 | |
| | 6/25/2020 | 18:33:10 | 49 | 106 | -3 | -2.83% | 66 | |

FIG. 20 (cont.)

| | | | | | | | |
|---|---|---|---|---|---|---|---|
| 30 (1950) | 5/4/2020 | 12:24:12 | 32 | 96 | -13 | -11.93% | 40 |
| 31 (1999) | 4/8/2020 | 14:57:33 | 47 | 109 | | | 73 |
| | 5/22/2020 | 18:05:34 | 40 | 85 | -4 | -4.49% | 16 |
| 32 (1948) | 4/9/2020 | 21:16:34 | 43 | 89 | | | 23 |
| | 9/26/2018 | 17:36:00 | 28 | 101 | | | 53 |
| | 6/27/2018 | 14:17:30 | -16 | 70 | 31 | 44.29% | 2 |
| 33 (1959) | 9/1/2020 | 9:30:18 | 42 | 105 | | | 63 |
| | 7/15/2020 | 10:43:15 | 43 | 106 | -1 | -0.94% | 66 |
| 34 (1989) | 6/1/2020 | 11:27:43 | 56 | 111 | | | 77 |
| | 4/27/2020 | 10:26:06 | 52 | 105 | 6 | 5.71% | 63 |
| 35 (1948) | 9/6/2019 | 9:28:37 | 28 | 101 | | | 53 |
| | 5/30/2019 | 14:03:09 | 37 | 107 | -6 | -5.61% | 68 |
| 36 (1946) | 2/16/2019 | 14:44:47 | 27 | 100 | | | 50 |
| | 1/11/2019 | 17:42:18 | 25 | 99 | 1 | 1.01% | 47 |
| 37 (1972) | 6/5/2020 | 13:27:08 | 51 | 108 | | | 70 |
| | 4/27/2020 | 12:00:26 | 52 | 109 | -1 | -0.92% | 73 |
| 38 (1951) | 5/4/2020 | 16:55:39 | 39 | 102 | | | 55 |
| | 4/17/2020 | 12:08:56 | 31 | 95 | 7 | 7.37% | 37 |
| 39 (1959) | 5/6/2020 | 6:45:43 | 45 | 107 | | | 68 |
| | 1/29/2018 | 10:27:02 | 39 | 93 | 14 | 15.05% | 32 |
| 40 (1951) | 2/22/2019 | 21:50:15 | 43 | 106 | | | 66 |
| | 1/11/2019 | 11:06:11 | 41 | 104 | 2 | 1.92% | 61 |
| 41 (1978) | 6/29/2020 | 17:19:21 | 21 | 71 | | | 3 |
| | 5/18/2020 | 11:28:02 | 27 | 78 | -7 | -8.97% | 7 |
| 42 (1953) | 3/1/2020 | 7:24:34 | 38 | 101 | | | 53 |
| | 6/13/2019 | 8:48:51 | 29 | 93 | 8 | 8.60% | 32 |
| 43 (1962) | 10/15/2019 | 10:35:51 | 36 | 89 | | | 23 |
| | 8/29/2019 | 0:27:14 | 14 | 59 | 30 | 50.85% | 1 |
| | | | | MIN | -13 | | |
| | | | | MAX | 31 | | |
| | 6 SCORE | TOTAL AVG | | AVG | 7.67 | 9.80% | |

FIG. 20 (cont.)

|  | AVG TOTAL | # POS |  |  |  |  | # POS | 33 |  |  |  |
|---|---|---|---|---|---|---|---|---|---|---|---|
|  | AVG TOTAL | # NEG |  |  |  |  | # NEG | 8 |  |  |  |
|  | AVG TOTAL | # ZERO |  |  |  |  | # ZERO | 2 |  |  |  |
|  |  |  |  |  |  |  |  | 43 |  |  |  |
|  |  |  |  |  |  |  |  |  |  |  |  |
|  |  |  |  |  |  |  |  |  |  |  |  |

FIG. 21

PHYSICIAN'S OBSERVATION DATA BEFORE AND AFTER BRAINI® ADMINISTRATION – PROCESSING SPEED

| Subject ID # (Birth Year) | Test Dates | Test Times | Processing Speed (Raw Subject Score) | Processing Speed (Standard Score) | Processing Speed (CHANGE) | Processing Speed (% CHANGE) | Processing Speed (Subject Percentile Rank) |
|---|---|---|---|---|---|---|---|
| 1 (1952) | 7/9/2019 | 19:28:24 | 57 | 118 | | | 88 |
| | 6/2/2019 | 13:49:44 | 52 | 111 | 7 | 6.31% | 77 |
| 2 (1941) | 9/3/2019 | 19:24:56 | 59 | 129 | | | 97 |
| | 7/13/2019 | 15:24:02 | 45 | 112 | 17 | 15.18% | 79 |
| 3 (1950) | 11/1/2018 | 9:55:54 | 43 | 99 | | | 47 |
| | 7/6/2018 | 13:05:18 | 40 | 95 | 4 | 4.21% | 37 |
| 4 (1991) | 6/8/2020 | 12:21:51 | 71 | 107 | | | 68 |
| | 4/10/2020 | 10:27:46 | 59 | 93 | 14 | 15.05% | 32 |
| 5 (1988) | 5/27/2020 | 11:18:15 | 72 | 117 | | | 87 |
| | 4/11/2020 | 6:39:29 | 49 | 84 | 33 | 39.29% | 14 |
| 6 (1950) | 9/5/2018 | 8:50:56 | 63 | 126 | | | 96 |
| | 7/2/2018 | 14:03:16 | 60 | 122 | 4 | 3.28% | 93 |
| 7 (1990) | 8/11/2020 | 18:11:21 | 49 | 84 | | | 14 |
| | 8/5/2020 | 16:47:13 | 42 | 74 | 10 | 13.51% | 4 |
| 8 (1989) | 4/13/2020 | 18:52:39 | 66 | 108 | | | 70 |
| | 2/21/2020 | 20:56:35 | 64 | 106 | 2 | 1.89% | 66 |
| 9 (1960) | 7/18/2020 | 10:42:48 | 48 | 97 | | | 42 |
| | 5/31/2020 | 11:12:59 | 42 | 87 | 10 | 11.49% | 19 |
| 10 (1961) | 6/1/2020 | 14:58:22 | 66 | 128 | | | 97 |
| | 4/10/2020 | 14:11:31 | 51 | 102 | 26 | 25.49% | 55 |
| 11 (1991) | 5/28/2020 | 8:17:00 | 65 | 100 | | | 50 |
| | 4/10/2020 | 13:47:18 | 61 | 95 | 5 | 5.26% | 37 |
| 12 (2009) | 3/8/2020 | 20:39:44 | 36 | 84 | | | 14 |
| | 2/3/2020 | 19:42:18 | 36 | 84 | 0 | 0.00% | 14 |
| 13 (1986) | 6/4/2020 | 1:57:36 | 69 | 113 | | | 81 |

FIG. 21 (cont.)

| | | | | | | | |
|---|---|---|---|---|---|---|---|
| 14 (1947) | 4/30/2020 | 1:53:30 | 53 | 90 | 23 | 25.56% | 25 |
| | 9/1/2018 | 14:31:43 | 35 | 99 | | | 47 |
| 15 (1976) | 6/22/2018 | 12:20:17 | 24 | 86 | 13 | 15.12% | 18 |
| | 9/4/2018 | 10:39:04 | 62 | 110 | | | 75 |
| 16 (1993) | 7/4/2018 | 14:49:22 | 46 | 87 | 23 | 26.44% | 19 |
| | 5/5/2020 | 15:43:39 | 82 | 121 | | | 92 |
| 17 (1938) | 4/13/2020 | 12:07:17 | 77 | 114 | 7 | 6.14% | 82 |
| | 6/27/2018 | 14:20:36 | 37 | 115 | | | 84 |
| 18 (1968) | 4/25/2018 | 16:31:24 | 25 | 97 | 18 | 18.56% | 42 |
| | 5/22/2020 | 14:34:27 | 88 | 166 | | | 99 |
| 19 (1991) | 4/19/2020 | 20:57:38 | 70 | 135 | 31 | 22.96% | 99 |
| | 7/22/2020 | 17:27:25 | 68 | 104 | | | 61 |
| 20 (1990) | 6/9/2020 | 20:23:45 | 68 | 104 | 0 | 0.00% | 61 |
| | 9/20/2019 | 10:52:36 | 63 | 97 | | | 42 |
| 21 (1991) | 8/26/2019 | 22:50:57 | 60 | 94 | 3 | 3.19% | 34 |
| | 7/30/2020 | 20:06:52 | 74 | 111 | | | 77 |
| 22 (1951) | 6/21/2020 | 11:08:15 | 68 | 104 | 7 | 6.73% | 61 |
| | 7/25/2019 | 15:36:31 | 58 | 119 | | | 90 |
| 23 (1983) | 2/26/2019 | 9:34:39 | 54 | 114 | 5 | 4.39% | 82 |
| | 9/15/2020 | 20:59:09 | 63 | 104 | | | 61 |
| 24 (1962) | 8/3/2020 | 20:45:00 | 64 | 106 | -2 | -1.89% | 66 |
| | 3/3/2020 | 10:38:07 | 59 | 116 | | | 86 |
| 25 (1985) | 1/30/2020 | 19:32:48 | 48 | 97 | 19 | 19.59% | 42 |
| | 6/3/2020 | 10:25:29 | 59 | 98 | | | 45 |
| 26 (1956) | 4/29/2020 | 9:59:48 | 60 | 100 | -2 | -2.00% | 50 |
| | 9/12/2019 | 21:45:42 | 56 | 117 | | | 87 |
| 27 (1940) | 7/24/2019 | 21:55:56 | 50 | 109 | 8 | 7.34% | 73 |
| | 2/23/2019 | 13:03:37 | 30 | 93 | | | 32 |
| 28 (1988) | 1/13/2019 | 8:12:07 | 26 | 88 | 5 | 5.68% | 21 |
| | 4/27/2020 | 11:39:24 | 81 | 130 | | | 98 |
| 29 (1973) | 3/9/2020 | 18:13:15 | 79 | 127 | 3 | 2.36% | 96 |
| | 8/16/2020 | 18:11:56 | 52 | 96 | | | 40 |
| | 6/25/2020 | 18:33:10 | 56 | 101 | -5 | -4.95% | 53 |

FIG. 21 (cont.)

| | 6 SCORE | TOTAL AVG | | | | | |
|---|---|---|---|---|---|---|---|
| 30 (1950) | 5/4/2020 | 12:24:12 | 43 | 99 | | | 47 |
| 31 (1999) | 4/8/2020 | 14:57:33 | 40 | 95 | 4 | 4.21% | 37 |
| | 5/22/2020 | 18:05:34 | 51 | 83 | | | 13 |
| 32 (1948) | 4/9/2020 | 21:16:34 | 54 | 86 | -3 | -3.49% | 18 |
| | 9/26/2018 | 17:36:00 | 38 | 103 | | | 58 |
| | 6/27/2018 | 14:17:30 | 40 | 105 | -2 | -1.90% | 63 |
| 33 (1959) | 9/1/2020 | 9:30:18 | 62 | 125 | | | 95 |
| | 7/15/2020 | 10:43:15 | 50 | 109 | 16 | 14.68% | 73 |
| 34 (1989) | 6/1/2020 | 11:27:43 | 73 | 119 | | | 90 |
| | 4/27/2020 | 10:26:06 | 65 | 107 | 12 | 11.21% | 68 |
| 35 (1948) | 9/6/2019 | 9:28:37 | 52 | 120 | | | 91 |
| | 5/30/2019 | 14:03:09 | 74 | 147 | -27 | -18.37% | 99 |
| 36 (1946) | 2/16/2019 | 14:44:47 | 49 | 117 | | | 87 |
| | 1/11/2019 | 17:42:18 | 14 | 74 | 43 | 58.11% | 4 |
| 37 (1972) | 6/5/2020 | 13:27:08 | 57 | 103 | | | 58 |
| | 4/27/2020 | 12:00:26 | 55 | 100 | 3 | 3.00% | 50 |
| 38 (1951) | 5/4/2020 | 16:55:39 | 33 | 86 | | | 18 |
| | 4/17/2020 | 12:08:56 | 41 | 97 | -11 | -11.34% | 42 |
| 39 (1959) | 5/6/2020 | 6:45:43 | 59 | 121 | | | 92 |
| | 1/29/2018 | 10:27:02 | 43 | 88 | 33 | 37.50% | 21 |
| 40 (1951) | 2/22/2019 | 21:50:15 | 48 | 106 | | | 66 |
| | 1/11/2019 | 11:06:11 | 41 | 97 | 9 | 9.28% | 42 |
| 41 (1978) | 6/29/2020 | 17:19:21 | 37 | 75 | | | 5 |
| | 5/18/2020 | 11:28:02 | 43 | 83 | -8 | -9.64% | 13 |
| 42 (1953) | 3/1/2020 | 7:24:34 | 45 | 102 | | | 55 |
| | 6/13/2019 | 8:48:51 | 43 | 99 | 3 | 3.03% | 47 |
| 43 (1962) | 10/15/2019 | 10:35:51 | 38 | 80 | | | 9 |
| | 8/29/2019 | 0:27:14 | 30 | 66 | 14 | 21.21% | 1 |
| | | | | MIN | -27 | | |
| | | | | MAX | 43 | | |
| | | | | AVG | 8.70 | 9.62% | |

FIG. 21 (cont.)

| AVG TOTAL | # POS | 31 | | | | |
| AVG TOTAL | # NEG | 10 | | | | |
| AVG TOTAL | # ZERO | 2 | | | | |
| | | 43 | | | | |
| AVG TOTAL | # POS | | | | | |
| AVG TOTAL | # NEG | | | | | |
| AVG TOTAL | # ZERO | | | | | |
| | | | | | | |
| | | | | | | |

FIG. 22

PHYSICIAN'S OBSERVATION DATA BEFORE AND AFTER BRAINI® ADMINISTRATION – EXECUTIVE FUNCTION

| Subject ID # (Birth Year) | Test Dates | Test Times | Executive Function (Raw Subject Score) | Executive Function (Standard Score) | Executive Function (CHANGE) | Executive Function (% CHANGE) | Executive Function (Subject Percentile Rank) |
|---|---|---|---|---|---|---|---|
| 1 (1952) | 7/9/2019 | 19:28:24 | 42 | 103 | | | 58 |
| | 6/2/2019 | 13:49:44 | 57 | 117 | -14 | -11.97% | 87 |
| 2 (1941) | 9/3/2019 | 19:24:56 | 45 | 111 | | | 77 |
| | 7/13/2019 | 15:24:02 | 47 | 113 | -2 | -1.77% | 81 |
| 3 (1950) | 11/1/2018 | 9:55:54 | 35 | 97 | | | 42 |
| | 7/6/2018 | 13:05:18 | 29 | 92 | 5 | 5.43% | 30 |
| 4 (1991) | 6/8/2020 | 12:21:51 | 59 | 113 | | | 81 |
| | 4/10/2020 | 10:27:46 | 46 | 93 | 20 | 21.51% | 32 |
| 5 (1988) | 5/27/2020 | 11:18:15 | 36 | 79 | | | 8 |
| | 4/11/2020 | 6:39:29 | 28 | 67 | 12 | 17.91% | 1 |
| 6 (1950) | 9/5/2018 | 8:50:56 | 44 | 105 | | | 63 |
| | 7/2/2018 | 14:03:16 | 39 | 101 | 4 | 3.96% | 53 |
| 7 (1990) | 8/11/2020 | 18:11:21 | 41 | 87 | | | 19 |
| | 8/5/2020 | 16:47:13 | 32 | 73 | 14 | 19.18% | 4 |
| 8 (1989) | 4/13/2020 | 18:52:39 | 53 | 105 | | | 63 |
| | 2/21/2020 | 20:56:35 | 48 | 98 | 7 | 7.14% | 45 |
| 9 (1960) | 7/18/2020 | 10:42:48 | 51 | 109 | | | 73 |
| | 5/31/2020 | 11:12:59 | 40 | 94 | 15 | 15.96% | 34 |
| 10 (1961) | 6/1/2020 | 14:58:22 | 56 | 116 | | | 86 |
| | 4/10/2020 | 14:11:31 | 47 | 103 | 13 | 12.62% | 58 |
| 11 (1991) | 5/28/2020 | 8:17:00 | 54 | 105 | | | 63 |
| | 4/10/2020 | 13:47:18 | 36 | 78 | 27 | 34.62% | 7 |
| 12 (2009) | 3/8/2020 | 20:39:44 | 17 | 88 | | | 21 |
| | 2/3/2020 | 19:42:18 | 2 | 74 | 14 | 18.92% | 4 |
| 13 (1986) | 6/4/2020 | 1:57:36 | 52 | 104 | | | 61 |

FIG. 22 (cont.)

| | | | | | | | |
|---|---|---|---|---|---|---|---|
| 14 (1947) | 4/30/2020 | 1:53:30 | 34 | 76 | 28 | 36.84% | 5 |
| | 9/1/2018 | 14:31:43 | 39 | 107 | | | 68 |
| 15 (1976) | 6/22/2018 | 12:20:17 | 34 | 104 | 3 | 2.88% | 61 |
| | 9/4/2018 | 10:39:04 | 52 | 108 | | | 70 |
| | 7/4/2018 | 14:49:22 | 51 | 107 | 1 | 0.93% | 68 |
| 16 (1993) | 5/5/2020 | 15:43:39 | 61 | 116 | | | 86 |
| | 4/13/2020 | 12:07:17 | 55 | 107 | 9 | 8.41% | 68 |
| 17 (1938) | 6/27/2018 | 14:20:36 | 11 | 93 | | | 32 |
| | 4/25/2018 | 16:31:24 | -1 | 85 | 8 | 9.41% | 16 |
| 18 (1968) | 5/22/2020 | 14:34:27 | 42 | 96 | | | 40 |
| | 4/19/2020 | 20:57:38 | 30 | 80 | 16 | 20.00% | 9 |
| 19 (1991) | 7/22/2020 | 17:27:25 | 57 | 110 | | | 75 |
| | 6/9/2020 | 20:23:45 | 43 | 88 | 22 | 25.00% | 21 |
| 20 (1990) | 9/20/2019 | 10:52:36 | 43 | 88 | | | 21 |
| | 8/26/2019 | 22:50:57 | 38 | 81 | 7 | 8.64% | 10 |
| 21 (1991) | 7/30/2020 | 20:06:52 | 49 | 97 | | | 42 |
| | 6/21/2020 | 11:08:15 | 45 | 91 | 6 | 6.59% | 27 |
| 22 (1951) | 7/25/2019 | 15:36:31 | 54 | 114 | | | 82 |
| | 2/26/2019 | 9:34:39 | 55 | 115 | -1 | -0.87% | 84 |
| 23 (1983) | 9/15/2020 | 20:59:09 | 64 | 122 | | | 93 |
| | 8/3/2020 | 20:45:00 | 54 | 107 | 15 | 14.02% | 68 |
| 24 (1962) | 3/3/2020 | 10:38:07 | 36 | 88 | | | 21 |
| | 1/30/2020 | 19:32:48 | 23 | 70 | 18 | 25.71% | 2 |
| 25 (1985) | 6/3/2020 | 10:25:29 | 53 | 105 | | | 63 |
| | 4/29/2020 | 9:59:48 | 56 | 110 | -5 | -4.55% | 75 |
| 26 (1956) | 9/12/2019 | 21:45:42 | 50 | 111 | | | 77 |
| | 7/24/2019 | 21:55:56 | 32 | 94 | 17 | 18.09% | 34 |
| 27 (1940) | 2/23/2019 | 13:03:37 | 41 | 109 | | | 73 |
| | 1/13/2019 | 8:12:07 | 35 | 105 | 4 | 3.81% | 63 |
| 28 (1988) | 4/27/2020 | 11:39:24 | 60 | 116 | | | 86 |
| | 3/9/2020 | 18:13:15 | 56 | 110 | 6 | 5.45% | 75 |
| 29 (1973) | 8/16/2020 | 18:11:56 | 48 | 103 | | | 58 |
| | 6/25/2020 | 18:33:10 | 51 | 107 | -4 | -3.74% | 68 |

FIG. 22 (cont.)

|  |  | TOTAL AVG |  |  |  |  |
|---|---|---|---|---|---|---|
| 30 (1950) | 5/4/2020 | 12:24:12 | 34 | 96 |  |  | 40 |
| 31 (1999) | 4/8/2020 | 14:57:33 | 47 | 108 | -12 | -11.11% | 70 |
|  | 5/22/2020 | 18:05:34 | 43 | 88 |  |  | 21 |
| 32 (1948) | 4/9/2020 | 21:16:34 | 45 | 91 | -3 | -3.30% | 27 |
|  | 9/26/2018 | 17:36:00 | 28 | 100 |  |  | 50 |
| 33 (1959) | 6/27/2018 | 14:17:30 | -16 | 70 | 30 | 42.86% | 2 |
|  | 9/1/2020 | 9:30:18 | 43 | 104 |  |  | 61 |
| 34 (1989) | 7/15/2020 | 10:43:15 | 43 | 104 | 0 | 0.00% | 61 |
|  | 6/1/2020 | 11:27:43 | 57 | 111 |  |  | 77 |
| 35 (1948) | 4/27/2020 | 10:26:06 | 53 | 105 | 6 | 5.71% | 63 |
|  | 9/6/2019 | 9:28:37 | 30 | 101 |  |  | 53 |
| 36 (1946) | 5/30/2019 | 14:03:09 | 38 | 107 | -6 | -5.61% | 68 |
|  | 2/16/2019 | 14:44:47 | 27 | 99 |  |  | 47 |
| 37 (1972) | 1/11/2019 | 17:42:18 | 27 | 99 | 0 | 0.00% | 47 |
|  | 6/5/2020 | 13:27:08 | 53 | 110 |  |  | 75 |
| 38 (1951) | 4/27/2020 | 12:00:26 | 56 | 113 | -3 | -2.65% | 81 |
|  | 5/4/2020 | 16:55:39 | 41 | 103 |  |  | 58 |
| 39 (1959) | 4/17/2020 | 12:08:56 | 33 | 95 | 8 | 8.42% | 37 |
|  | 5/6/2020 | 6:45:43 | 48 | 109 |  |  | 73 |
| 40 (1951) | 1/29/2018 | 10:27:02 | 40 | 94 | 15 | 15.96% | 34 |
|  | 2/22/2019 | 21:50:15 | 46 | 107 |  |  | 68 |
| 41 (1978) | 1/11/2019 | 11:06:11 | 44 | 105 | 2 | 1.90% | 63 |
|  | 6/29/2020 | 17:19:21 | 22 | 71 |  |  | 3 |
| 42 (1953) | 5/18/2020 | 11:28:02 | 29 | 79 | -8 | -10.13% | 8 |
|  | 3/1/2020 | 7:24:34 | 40 | 102 |  |  | 55 |
| 43 (1962) | 6/13/2019 | 8:48:51 | 31 | 94 | 8 | 8.51% | 34 |
|  | 10/15/2019 | 10:35:51 | 36 | 88 |  |  | 21 |
|  | 8/29/2019 | 0:27:14 | 15 | 59 | 29 | 49.15% | 1 |
|  |  |  |  | MIN | -14 |  |  |
|  |  |  |  | MAX | 30 |  |  |
|  | 6 SCORE |  |  | AVG | 7.70 | 9.76% |  |

FIG. 22 (cont.)

| AVG TOTAL | # POS | | | | | | # POS | 30 | | | | | | |
|---|---|---|---|---|---|---|---|---|---|---|---|---|---|---|
| AVG TOTAL | # NEG | | | | | | # NEG | 9 | | | | | | |
| AVG TOTAL | # ZERO | | | | | | # ZERO | 4 | | | | | | |
| | | | | | | | | 43 | | | | | | |

FIG. 23

PHYSICIAN'S OBSERVATION DATA BEFORE AND AFTER BRAINI® ADMINISTRATION – MOTOR SPEED

| Subject ID # (Birth Year) | Test Dates | Test Times | Motor Speed (Raw Subject Score) | Motor Speed (Standard Score) | Motor Speed (CHANGE) | Motor Speed (% CHANGE) | Motor Speed (Subject Percentile Rank) | Duration (milliseconds) |
|---|---|---|---|---|---|---|---|---|
| 1 (1952) | 7/9/2019 | 19:28:24 | 128 | 119 | | | 90 | 1010 |
|  | 6/2/2019 | 13:49:44 | 116 | 108 | 11 | 10.19% | 70 | 980 |
| 2 (1941) | 9/3/2019 | 19:24:56 | 102 | 106 | | | 66 | 964 |
|  | 7/13/2019 | 15:24:02 | 82 | 86 | 20 | 23.26% | 18 | 1054 |
| 3 (1950) | 11/1/2018 | 9:55:54 | 104 | 97 | | | 42 | 1253 |
|  | 7/6/2018 | 13:05:18 | 94 | 88 | 9 | 10.23% | 21 | 1383 |
| 4 (1991) | 6/8/2020 | 12:21:51 | 139 | 118 | | | 88 | 1959 |
|  | 4/10/2020 | 10:27:46 | 133 | 113 | 5 | 4.42% | 81 | 1213 |
| 5 (1988) | 5/27/2020 | 11:18:15 | 132 | 112 | | | 79 | 681 |
|  | 4/11/2020 | 6:39:29 | 132 | 112 | 0 | 0.00% | 79 | 825 |
| 6 (1950) | 9/5/2018 | 8:50:56 | 127 | 118 | | | 88 | 1114 |
|  | 7/2/2018 | 14:03:16 | 113 | 105 | 13 | 12.38% | 63 | 1283 |
| 7 (1990) | 8/11/2020 | 18:11:21 | 109 | 94 | | | 34 | 728 |
|  | 8/5/2020 | 16:47:13 | 105 | 91 | 3 | 3.30% | 27 | 813 |
| 8 (1989) | 4/13/2020 | 18:52:39 | 126 | 107 | | | 68 | 757 |
|  | 2/21/2020 | 20:56:35 | 112 | 96 | 11 | 11.46% | 40 | 786 |
| 9 (1960) | 7/18/2020 | 10:42:48 | 118 | 107 | | | 68 | 1054 |
|  | 5/31/2020 | 11:12:59 | 118 | 107 | 0 | 0.00% | 68 | 1197 |
| 10 (1961) | 6/1/2020 | 14:58:22 | 115 | 103 | | | 58 | 853 |
|  | 4/10/2020 | 14:11:31 | 119 | 108 | -5 | -4.63% | 70 | 834 |
| 11 (1991) | 5/28/2020 | 8:17:00 | 96 | 80 | | | 9 | 736 |
|  | 4/10/2020 | 13:47:18 | 69 | 57 | 23 | 40.35% | 1 | 827 |
| 12 (2009) | 3/8/2020 | 20:39:44 | 106 | 101 | | | 53 | 1292 |
|  | 2/3/2020 | 19:42:18 | 102 | 97 | 4 | 4.12% | 42 | 963 |
| 13 (1986) | 6/4/2020 | 1:57:36 | 94 | 82 | | | 12 | 754 |

FIG. 23 (cont.)

| | | | | | | | |
|---|---|---|---|---|---|---|---|
| 14 (1947) | 4/30/2020 | 1:53:30 | 89 | 78 | 4 | 5.13% | 7 | 898 |
| | 9/1/2018 | 14:31:43 | 119 | 124 | | | 95 | 1018 |
| 15 (1976) | 6/22/2018 | 12:20:17 | 109 | 114 | 10 | 8.77% | 82 | 1278 |
| | 9/4/2018 | 10:39:04 | 110 | 93 | | | 32 | 972 |
| | 7/4/2018 | 14:49:22 | 107 | 90 | 3 | 3.33% | 25 | 958 |
| 16 (1993) | 5/5/2020 | 15:43:39 | 139 | 118 | | | 88 | 1086 |
| | 4/13/2020 | 12:07:17 | 142 | 120 | -2 | -1.67% | 91 | 1466 |
| 17 (1938) | 6/27/2018 | 14:20:36 | 67 | 85 | | | 16 | 1143 |
| | 4/25/2018 | 16:31:24 | 105 | 112 | -27 | -24.11% | 79 | 2674 |
| 18 (1968) | 5/22/2020 | 14:34:27 | 113 | 101 | | | 53 | 906 |
| | 4/19/2020 | 20:57:38 | 97 | 83 | 18 | 21.69% | 13 | 1053 |
| 19 (1991) | 7/22/2020 | 17:27:25 | 128 | 108 | | | 70 | 691 |
| | 6/9/2020 | 20:23:45 | 135 | 114 | -6 | -5.26% | 82 | 735 |
| 20 (1990) | 9/20/2019 | 10:52:36 | 132 | 112 | | | 79 | 952 |
| | 8/26/2019 | 22:50:57 | 136 | 115 | -3 | -2.61% | 84 | 1222 |
| 21 (1991) | 7/30/2020 | 20:06:52 | 148 | 126 | | | 96 | 778 |
| | 6/21/2020 | 11:08:15 | 142 | 120 | 6 | 5.00% | 91 | 884 |
| 22 (1951) | 7/25/2019 | 15:36:31 | 88 | 82 | | | 12 | 1114 |
| | 2/26/2019 | 9:34:39 | 70 | 66 | 16 | 24.24% | 1 | 1086 |
| 23 (1983) | 9/15/2020 | 20:59:09 | 122 | 104 | | | 61 | 942 |
| | 8/3/2020 | 20:45:00 | 119 | 102 | 2 | 1.96% | 55 | 790 |
| 24 (1962) | 3/3/2020 | 10:38:07 | 113 | 101 | | | 53 | 772 |
| | 1/30/2020 | 19:32:48 | 104 | 91 | 10 | 10.99% | 27 | 969 |
| 25 (1985) | 6/3/2020 | 10:25:29 | 121 | 103 | | | 58 | 728 |
| | 4/29/2020 | 9:59:48 | 118 | 101 | 2 | 1.98% | 53 | 795 |
| 26 (1956) | 9/12/2019 | 21:45:42 | 114 | 106 | | | 66 | 902 |
| | 7/24/2019 | 21:55:56 | 107 | 100 | 6 | 6.00% | 50 | 956 |
| 27 (1940) | 2/23/2019 | 13:03:37 | 124 | 129 | | | 97 | 1168 |
| | 1/13/2019 | 8:12:07 | 105 | 109 | 20 | 18.35% | 73 | 1276 |
| 28 (1988) | 4/27/2020 | 11:39:24 | 138 | 117 | | | 87 | 686 |
| | 3/9/2020 | 18:13:15 | 132 | 112 | 5 | 4.46% | 79 | 723 |
| 29 (1973) | 8/16/2020 | 18:11:56 | 117 | 100 | | | 50 | 867 |
| | 6/25/2020 | 18:33:10 | 105 | 88 | 12 | 13.64% | 21 | 885 |

FIG. 23 (cont.)

| | | | | | | | | |
|---|---|---|---|---|---|---|---|---|
| 30 (1950) | 5/4/2020 | 12:24:12 | 99 | 92 | | | 30 | 972 |
| 31 (1999) | 4/8/2020 | 14:57:33 | 104 | 97 | -5 | -5.15% | 42 | 1197 |
| 32 (1948) | 5/22/2020 | 18:05:34 | 127 | 107 | | | 68 | 855 |
| | 4/9/2020 | 21:16:34 | 127 | 107 | 0 | 0.00% | 68 | 961 |
| | 9/26/2018 | 17:36:00 | 96 | 100 | | | 50 | 1189 |
| | 6/27/2018 | 14:17:30 | 90 | 94 | 6 | 6.38% | 34 | 1288 |
| 33 (1959) | 9/1/2020 | 9:30:18 | 119 | 111 | | | 77 | 813 |
| | 7/15/2020 | 10:43:15 | 130 | 121 | -10 | -8.26% | 92 | 896 |
| 34 (1989) | 6/1/2020 | 11:27:43 | 120 | 103 | | | 58 | 892 |
| | 4/27/2020 | 10:26:06 | 121 | 103 | 0 | 0.00% | 58 | 871 |
| 35 (1948) | 9/6/2019 | 9:28:37 | 100 | 104 | | | 61 | 1085 |
| | 5/30/2019 | 14:03:09 | 105 | 109 | -5 | -4.59% | 73 | 1107 |
| 36 (1946) | 2/16/2019 | 14:44:47 | 79 | 83 | | | 13 | 1377 |
| | 1/11/2019 | 17:42:18 | 55 | 59 | 24 | 40.68% | 1 | 1680 |
| 37 (1972) | 6/5/2020 | 13:27:08 | 143 | 127 | | | 96 | 820 |
| | 4/27/2020 | 12:00:26 | 129 | 113 | 14 | 12.39% | 81 | 883 |
| 38 (1951) | 5/4/2020 | 16:55:39 | 104 | 97 | | | 42 | 971 |
| | 4/17/2020 | 12:08:56 | 108 | 100 | -3 | -3.00% | 50 | 1314 |
| 39 (1959) | 5/6/2020 | 6:45:43 | 152 | 141 | | | 99 | 839 |
| | 1/29/2018 | 10:27:02 | 130 | 120 | 21 | 17.50% | 91 | 2457 |
| 40 (1951) | 2/22/2019 | 21:50:15 | 101 | 94 | | | 34 | 1029 |
| | 1/11/2019 | 11:06:11 | 91 | 85 | 9 | 10.59% | 16 | 994 |
| 41 (1978) | 6/29/2020 | 17:19:21 | 115 | 98 | | | 45 | 815 |
| | 5/18/2020 | 11:28:02 | 102 | 85 | 13 | 15.29% | 16 | 1099 |
| 42 (1953) | 3/1/2020 | 7:24:34 | 121 | 112 | | | 79 | 822 |
| | 6/13/2019 | 8:48:51 | 116 | 108 | 4 | 3.70% | 70 | 1018 |
| 43 (1962) | 10/15/2019 | 10:35:51 | 70 | 53 | | | 1 | 1360 |
| | 8/29/2019 | 0:27:14 | 46 | 27 | 26 | 96.30% | 1 | 1686 |
| | | | | MIN | -27 | | | |
| | | | | MAX | 26 | | | |
| 6 SCORE | | TOTAL AVG | | AVG | 6.14 | 9.04% | | |

METHODS AND COMPOSITIONS WITH PURIFIED *BOMBYX MORI* COCOON SILK PEPTIDE FIBER AND REFINED *BUGLOSSOIDES ARVENSIS* SEED OIL PROVIDING ANTI-INFLAMMATORY EFFECTS AND NEUROPROTECTION FOR DISEASE STATES

CROSS-REFERENCE TO RELATED APPLICATIONS

This application is a continuation-in-part application claiming the benefit of U.S. patent application Ser. No. 17/067,489, filed Oct. 9, 2020, which claims the benefit of U.S. Provisional Patent Application No. 62/912,956, filed Oct. 9, 2019. Each of the applications identified above is incorporated by reference herein in its entirety.

FIELD OF THE INVENTION

The present invention relates to compositions comprising a synergistic combination of purified *Bombyx mori* cocoon silk peptide fiber, refined *Buglossoides arvensis* seed oil, and optionally Blueberry extract, and related methods for decreasing inflammation and providing neuroprotection. The compositions provide synergistic effects and may be used to treat relevant diseases and disorders.

BACKGROUND

In a rapidly advancing society, interest in brain health and memory as well as a demand for related health products is increasing continuously along with the aim of obtaining additional information about neuro-protective and neuro-restorative dietary interventions, given the recent rise in aging population demographics, in the levels of information-intensive jobs, and in the far greater learning and information management tasks they require. Although the focus of the demand historically has been patient-centric, typically restricted to prescription medicines aiding in the reduction of partial or early-onset memory decline, such as with age-related dementia, nowadays healthy and normal people who wish to strengthen their memory and cognitive performance along with patients facing mild memory decline are actively searching for nutritional supplements and "neuro-tropic"/"nootropic" health foods or functional foods that are able to act as memory boosters. Therefore, many related products have been released and sold in various forms following indications of in vitro neural cell protection/enhancement or in vivo memory improvement.

Neuroscience (Pathology of Brain Memory)

Memory does not work through discrete fragmentary mechanisms. Instead, memory appears to result from highly complex interactions between many physiological functions and neurotransmitters acting in concert. For example, the following neurotransmitters which are either directly or indirectly related to memory exist:

| Neuro-transmitters | Representative Functions | Lack Causes | Excess Causes |
| --- | --- | --- | --- |
| Acetylcholine | Learning | Memory problem, Dementia, Alzheimer's disease | Violent muscle contractions |
| Dopamine | Pleasure | Parkinson's disease, ADHD (Attention-Deficit/Hyperactivity Disorder) | Schizophrenia |
| Serotonin | Mood | Rumination, Depression | Serotonin Syndrome |
| Norepinephrine (noradrenaline) | Concentration | Hypotension, ADHD | Increase heart rate & pressure. |
| GABA | Calming | Anxiety | Paradoxical Anxiety |

Among such neurotransmitters, acetylcholine is of particular interest, given that significant memory improvement effects can be anticipated when related functions are locally controlled. Acetylcholine deficiency is known to occur frequently with aging Maintaining an appropriate level of acetylcholine, as opposed to other neurotransmitters, is particularly crucial for the maintenance of memory.

Existing health supplements supporting brain health and memory are mostly simple, made from purportedly effective Active Dietary Ingredients (ADIs).

The majority of commercialized products are made either from a sole nootropic ingredient, which affects cognitive abilities and memory, or simple combinations of many natural ingredients. Although some beneficial effects can be expected from many of these products, such products created without underlying scientific designs may result in substantial differences in effectiveness and in various side effects among different patients.

To successfully activate effective neuro-protective and/or neuro-restorative actions of a candidate medicinal ingredient that will avoid any negative side effects in virtually all patients, makers of the product must consider several factors including the activity of the medicinal ingredient, the underlying mechanism(s) of actions, patients' pathophysiology, and the absorption of the medicinal ingredient.

Corresponding Characteristics of Consumers

Consumers of such health products can be divided into two main groups, namely: those who require memory improvement due to aging; and students and workers who wish to learn, process, and retain new knowledge more efficiently and with greater cognitive performance.

Following an examination of older people's pathophysiology, digestive functions (e.g., secretion of digestive fluids and gastrointestinal movement) and ADME (absorption, distribution, metabolism, elimination) are found generally to diminish with increasing age. Although health product types differ depending on the medicinal ingredients involved, their administration in smaller more frequent dosages is needed given that their speed of metabolism is often slower. Atrophic gastritis, also known as achlorhydria, occurs in 30% of the elderly population, while many cases of incomplete absorption despite taking in sufficient nutrition are commonly reported.

Students who wish to increase their learning and workers who must complete various complex cognitive tasks commonly experience indigestion and abdominal pain due to stress related to more intensive learning requirements. Further, nutrient absorption and metabolism are sometimes reduced indirectly as well. Also, homeostenosis can commonly occur in these consumers, especially in seniors or in those with chronic stress. A nutritional imbalance in this condition can increase the possibility of either permanent functional damage or vulnerability to other diseases, given that the ability to return to the original state is compromised, even when proper dietary supplementation or other corrections are performed later. Designing health products which sufficiently consider neuro-protective and/or neuro-restorative effects related to memory as well as points as mentioned earlier would be advantageous.

There is a need for compositions and methods that may decrease inflammation and oxidative stress in the body, and may provide for instance neuroprotection and other protection from inflammation and oxidative stress. See for instance Degan et al., *The Role of Inflammation in Neurological Disorders*, Curr. Pharm. Des. 24(14):1485-1501 (2018). See also for instance Morris et al., *Leaky brain in neurological and psychiatric disorders: Drivers and consequences*, Austr. New Zeal. J. Psychiat. 52(10):924-948 (2018); Enache et al., *Markers of central inflammation in major depressive disorder: A systematic review and meta-analysis of studies examining cerebrospinal fluid, positron emission tomography and post-mortem brain tissue*. Brain Behav. Immun. 81:24-40 (2019); Salter et al., *Microglia emerge as central players in brain disease*. Nat. Med. 23(9):1018-1027 (2017); Kwon et al., *Neuroinflammation in neurodegenerative disorders: the roles of microglia and astrocytes*. Transl. Neurodegen. 9:42 (2020; 12 pages); Kaur et al., *Neuroinflammation Mechanisms and Phytotherapeutic Intervention: A Systematic Review*. ACS Chem. Neurosci. 11:3707-3731 (2020). These documents are hereby incorporated by reference for the purpose of identifying disorders, diseases, conditions, and the like that may be treated, prevented, protected from, or otherwise assisted with the invention described below, to the extent allowed by law.

SUMMARY OF THE INVENTION

The present invention is directed to compositions comprising purified *Bombyx mori* cocoon silk peptide fiber, refined *Buglossoides arvensis* seed oil (e.g. NeurXcel®), and preferably Blueberry extract powder. Also, the invention is directed to methods for reducing inflammation and/or oxidative stress, providing neuroprotection, and/or treating/preventing diseases and disorders associated with inflammation and oxidative stress, including for instance those associated with sugar.

A composition of this invention, in an embodiment, comprises 20-2000 mg purified *Bombyx mori* cocoon silk peptide fiber and 20-10,000 mg refined *Buglossoides arvensis* seed oil. Other compositions of this invention comprise 200-400 mg, for instance about 400 mg, of purified *Bombyx mori* cocoon silk peptide fiber and/or 200-2500 mg, for instance 250 mg, refined *Buglossoides arvensis* micro-encapsulated seed oil. Optionally, a composition of the invention comprises 25-500 mg Blueberry Extract, or in another embodiment, 50-100 mg Blueberry Extract. Other compositions of this invention are also included in this invention.

Compositions of the invention are a dietary supplement, in an embodiment. Also, compositions of the present invention may include or be combined with further ingredients such as Acetyl-L-Carnitine, L-theanine, L-serine, Zinc (as zinc glycinate, zinc citrate, or zinc picolonate), Huperzine A extracted from clubmoss (*Huperzia chinensis*), *Bacopa monnieri* extract, Ginseng Extracts, *Zingiber officinalis* Extracts, Citicoline, *Ginkgo biloba* extract, Folic acid, and Haskap blue honeysuckle berry (*Lonicera caerulea*), Vitamin B12, Vitamin B6, Vitamin B1, Vitamin D3 (cholecalciferol), Greek Mountain Tea (*Sideritis* spp.), Lion's Mane mushrooms. The ingredients may be added to said compositions individually or according to groupings, such as those discussed below and throughout this application.

The present invention is also directed to a method for making the above-described compositions. The present invention is also directed to methods for using the present compositions to improve memory and/or cognitive performance in human subjects or other subjects, to provide neuroprotection, and/or to treat e.g. neurodegenerative diseases or disorders, and/or other neurological diseases, disorders, or pre-clinical conditions. Such methods generally comprise orally administering compositions according to the present invention to a human subject. Other methods are described or apparent from the data and throughout the application.

BRIEF DESCRIPTION OF THE DRAWINGS

FIG. 14 shows synergistic CNS Vital Signs results in vivo in healthy adult seniors after administration of Braini®, a synergistic composition of this invention.

FIG. 15 shows synergistic CNS Vital Signs results in vivo in an adult subject with Multiple Sclerosis after administration of Braini®, a synergistic composition of this invention.

FIG. 16A shows synergistic CNS Vital Signs results in vivo in adult subjects with dyslexia after administration of Braini®, a synergistic composition of this invention. FIG. 16B shows physician's observational data after Braini® administration in dyslexic subjects.

FIG. 17 shows synergistic CNS Vital Signs results in vivo in adult subjects first treated with Peptylin®, and then Braini®, a synergistic composition of this invention.

FIG. 18 is a table showing improvements in CNS Vital Signs Psychomotor Speed in human subjects after Braini® administration.

FIG. 19 is a table showing improvements in CNS Vital Signs Reaction Time in human subjects after Braini® administration.

FIG. 20 is a table showing improvements in CNS Vital Signs Cognitive Flexibility in human subjects after Braini® administration.

FIG. 21 is a table showing improvements in CNS Vital Signs Processing Speed in human subjects after Braini® administration.

FIG. 22 is a table showing improvements in CNS Vital Signs Executive Function in human subjects after Braini® administration.

FIG. 23 is a table showing improvements in CNS Vital Signs Motor Speed in human subjects after Braini® administration.

DETAILED DESCRIPTION OF THE INVENTION

Figure 1:
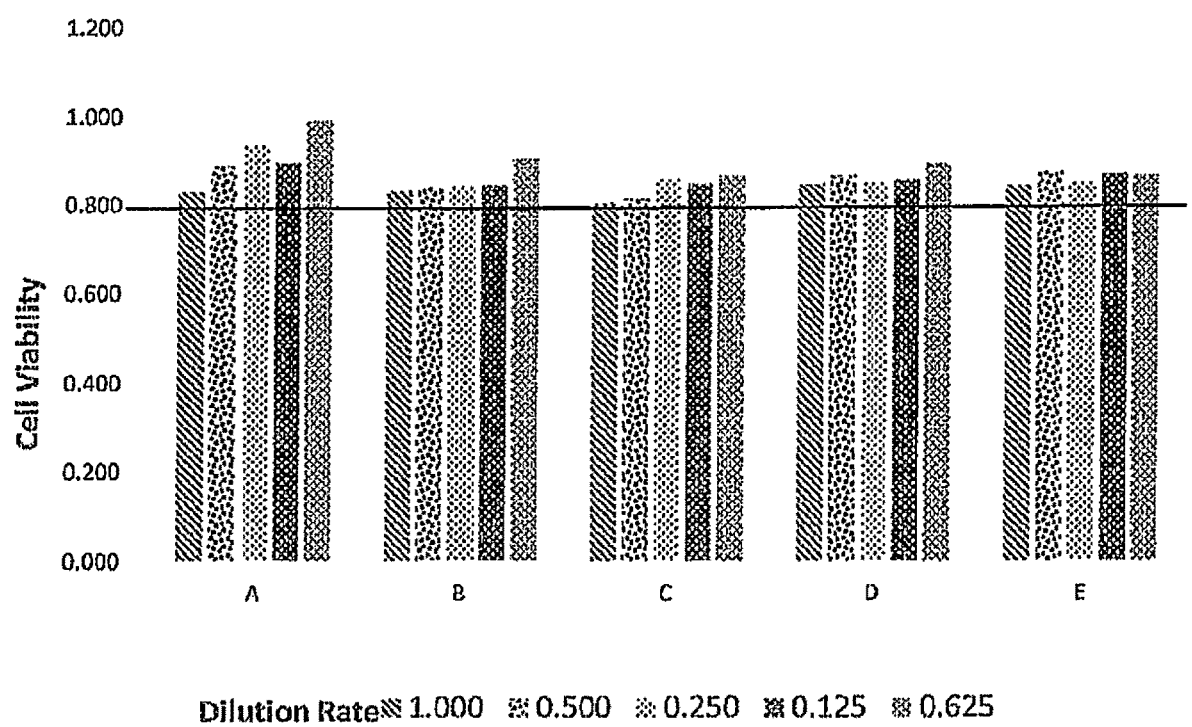
FIG. 1 is a graph showing in vitro cell viability in the presence of purified *Bombyx mori* cocoon silk peptide fiber alone (A) or after administration of compositions of the present invention (B-E).

The present invention is directed to a composition that improves memory and/or cognitive performance, provides neuroprotection, and/or can be used to treat diseases, disorders, and/or clinical conditions such as neurodegenerative disorders and neurological conditions such as dyslexia.

A composition of the present invention comprises purified *Bombyx mori* cocoon silk peptide fiber, refined *Buglossoides arvensis* seed oil, and preferably Blueberry extract. A composition in one embodiment is a simple blend of Peptylin® powder (purified *Bombyx mori* cocoon silk peptide fiber in powder form), refined *Buglossoides arvensis* seed oil (tradename: Ahiflower® or NeurXcel®, and for instance as NeurXcel Seed Oil modified powder), and BLUEd'OR Blueberry Extract powder. As discussed below, through careful research, the present application shows that the present compositions provide synergistic effects over their individual ingredients and demonstrates chemical modifications of the compositions of this invention.

Compositions used in exemplary in vitro and in vivo trials are described below in the section "Examples". Compositions used in exemplary in vivo (human) empirical and controlled clinical trials were formulated as a homogenous blend of micronized and/or microencapsulated powdered forms of the referenced active ingredients described throughout this application and for instance in the section "Definitions".

The present invention is also directed to a method for preparing compositions of the present invention. In one embodiment, a method for making a composition of the present invention comprises the step(s) of combining Peptylin® powder, refined *Buglossoides arvensis* seed oil in the form of modified powder such as NeurXcel® seed oil modified powder, and optionally BLUEd'OR® blueberry extract powder in specified amounts together, for instance to prepare a simple blend.

In another embodiment, a method of preparing a composition of the present invention comprises the step(s) of adding powdered ingredients to an inner capsule and refined *Buglossoides arvensis* seed oil to an outer capsule. For instance, Lonza/Capsugel's DuoCap® system provides inner and outer capsules which together may be administered to a subject as a single dose unit.

In another embodiment, a method of preparing a composition of the present invention comprises the steps of combining at least *B. mori* fiber, *B. arvensis* oil, and Blueberry Extract into a bulk powdered blend. In an embodiment, said combining is by blending the ingredients together in a V-mixer; in an embodiment, all ingredients are blended to homogeneity. In an embodiment, the particle size of a composition of this invention is set by the particle sizes of the original ingredients. In an embodiment, the particle size is of a powdered composition of this invention is such more than 90% of the blended powder will pass through an 80 mesh screen. In an embodiment, the blend may be ingested as is, added to food, or mixed with water, milk (for instance seed, nut, dairy), juice (fruit and/or vegetable, or the like), and/or other beverages (for instance, as a frozen or non-frozen shake) for direct consumption. In an embodiment, the blended powder composition may be added to a capsule for ingestion in capsule form. Compositions such as those described above, in an embodiment, are dietary supplements of this invention. In an embodiment, the active ingredients may be formulated into a gummi blend or other oral dosage form.

The present invention is also directed to methods for using the present compositions to improve memory and/or cognitive performance in human subjects, provide neuroprotection, and/or to treat neurodegenerative diseases or disorders or neurological conditions (for instance dyslexia), and/or other diseases, disorders, or pre-clinical conditions. The methods generally comprise orally administering the compositions in an effective amount to a human subject, for instance up to the maximum daily intake levels allowed by federal regulatory bodies.

Silk Proteins

Silk proteins and silk peptides refer to protein from the cocoon of the *Bombyx mori* L. silkworm, that may be partially hydrolyzed into peptides. The cocoons are frequently characterized as having two proteins, namely fibroin (~75%) and sericin (~25%).

Recently, silk peptide has been hydrolyzed and used in new ways compared to traditional applications. The silk peptide family is known to increase the concentration of acetylcholine in the body and to decrease acidic stress condition, providing a neural protection effect. Moreover, it is recognized to provide superb memory improvement and brain protection effects through the promotion of brain blood flow and the selective inhibition of catecholamine enzyme activity.

Silk peptide has been well documented by many clinical research studies to improve memory. Furthermore, the absence of side effects was reported several times across age groups. Clinical trials on healthy adults, children, young college students, young children, and seniors all confirmed high long-term and short-term memory improvements without side effects. They also revealed the silk peptide to be a safe and effective ingredient to use without distinction of either age or gender.

Vegetable Omega-3 Oil Fatty Acids

Omega-3 fatty acids are a type of essential unsaturated fatty acid which are actively used in the brain's metabolic activities. Omega-3 essential fatty acids are not synthesized in the body and must be consumed from dietary sources. Omega-3 fatty acids include: alpha-linolenic acid (ALA), stearidonic acid (SDA), eicosatetraenoic acid (ETA), eicosapentaenoic acid (EPA), docosapentaenoic acid (DPA), and docosahexaenoic acid (DHA).

Omega-3 fatty acids are the main ingredients composing neural cell membranes in the brain. In particular, while DHA is dominant in brain cell structures, other unsaturated omega-3 fatty acids are shorter carbon-chain metabolic precursors that are elongated and synthesized by the body and are converted into DHA when required, thus promoting an increase in acetylcholine. Specifically, ALA (a vegetable Omega-3) has acetylcholinesterase activity and the ability to increase the efficient use of acetylcholine.

While previous clinical studies described vegetable omega-3 oils to be essential for brain development, optimal cellular membrane functioning, and physical health, their concentration in the blood was reported to be related to both comprehension ability and memory capacity. Moreover, a previous investigation identified memory to be supported by a balance between omega-3 ALA, SDA, and omega-6 GLA, maintaining older adults' fluid intelligence and protecting frontal neocortex structure and Fornix white matter microstructure. Of note, refined *Buglossoides arvensis* seed oil is believed to be a rich available dietary source of combined ALA, SDA, and GLA from a single non-genetically modified plant. Without being bound by theory, this unique omega-3 and omega-6 fatty acid composition is a reason for using this dietary oil in the present invention.

Blueberry Extract (Standard)

Blueberry is a member of the *Vaccinium* genus and it exists in various species worldwide. Additionally, it contains much of the Polyphenol compounds (i.e., anthocyanin and flavonoids constituents with the highest-level content) and has potent antioxidant and anti-inflammatory effects.

The mechanisms behind these blueberries are known to include the prevention of age-induced oxidation of the brain cells, the ability to activate the neurotransmitter pathway of the brain cells, and blood vessel promotion effects that can latently induce neural cell growth.

Also, blueberry extracts containing such anthocyanin and flavonoids were shown to have an effect on memory improvement in paired-associate learning and word list recall in adults. A recent study on seniors also showed it to improve temporary memory.

Definitions

The below definitions and discussion are intended to guide understanding but are not intended to be limiting with regard to other disclosures in this application. References to percentage (%) in compositions of the present invention refers to the % by weight of a given component to the total weight of the composition or preparation being discussed, also signified by "w/w", unless stated otherwise. According to the present invention, "administration", "administering", and the like refer to providing a composition of the present invention to a subject so that the active ingredients (purified *Bombyx mori* cocoon silk peptide fiber, refined *Buglossoides arvensis* seed oil, and optionally blueberry extract) reach the subject's bloodstream and/or tissues, cells, or other bodily components and act to for instance to support cellular membrane functions, including barrier properties, porosity, permeability, ion transfer, and structural integrity, and to protect, generate, regenerate, upregulate, and/or reinforce neurophysiological pathways, neurotransmitter compounds, and/or naturally-occurring neuroprotective factors including microglial cells and other neuro-immune modulatory cells. In an embodiment, such actions are in particular in the brain and central nervous system. Administration may be by the subject or by another. Administration may be to a healthy subject or to a subject having a neurological disease or disorder. As discussed throughout this application, administration to the subject may be oral, for instance in the form of a dietary supplement, and/or in a solid dosage form, for instance as a discrete dose unit. Administration may also be through parenteral, intramuscular, transdermal, topical, nasal, sublingual, intravenous, and other physiologically acceptable routes. Administration of the present invention may be, for instance, in keeping with daily doses described throughout this application, for at least 1 day, any number of 1-7 days, 7-14 days, 10 days, 1 week, 2 weeks, 3 weeks, 4 weeks, 5 weeks, 6 weeks, 7 weeks, 1 month, 2 months, 3 months, 4 months, and any number of days, weeks or months up to 1 year. In an embodiment, administration of the present invention may be daily for 1 year, 2 years, 3 years, 4 years or longer, as desired by the subject or a health care provider. In an embodiment, a composition of this invention is administered every day during a period of treatment (i.e. on consecutive days); in an embodiment, the composition is administered for a period of treatment including at least 50% consecutive days. In an embodiment, administration of a composition of this invention is for at least 10 consecutive days.

"Co-administration" refers to administering a composition of the present invention with another known drug or substance. Compositions of the present invention may be administered with other drugs and/or substances, whether to further aid in improving neurocognitive functions or treating neurological diseases, disorders, or conditions, or in keeping with other needs of a given subject. Subjects taking statins (e.g. Rosuvastatin), blood thinners (e.g. Eliquis), levothyroxine, losarten, progesterone, estrogen, anti-histamines (e.g. Claritin), guaifenesin (e.g. Mucinex), acetaminophen (e.g. Tylenol), ibuprofen (e.g. Advil), naproxen (e.g. Aleve), antidepressants, antibiotics, Remdesevir®, steroids, plasma with COVID19 antibodies, and other medications, with a composition of the present invention (Braini® capsules) reported no side effects or adverse events.

According to the present invention, an "effective amount" is an amount of active ingredient administered in a sufficient amount to reach bodily cells and tissues and act on the bodily cells and tissues to effectively improve memory and/or cognitive performance, and/or provide neuroprotection, and/or support the body's natural defense against neurodegenerative states or diseases and/or a neurological condition such as dyslexia, or treats such diseases or conditions such as dyslexia, when administered to the human. Such may be achieved for instance by protection against oxidation and generation of reactive oxygen species, as shown in the Examples. In an embodiment, an active ingredient of this invention is optionally taken in combination with another active ingredient or ingredients of the present invention; in an embodiment, action at cells and tissues may include action by metabolites or other modifications of the active ingredient(s) by the body.

For instance, as shown in in vivo Examples below, an effective amount of active ingredients for synergistically improving CNS Vital Signs test results in adult humans is the composition Braini® of the present invention, comprising the following effective amounts of active ingredients of this invention: 400 mg/day Peptylin®, 500 mg/day NeurXcel® microencapsulated powder, and 100 mg/day Blueberry extract powder. 500 mg of NeurXcel® microencapsulated powder includes 250 mg NeurXcel® oil according to this invention.

In another embodiment, a composition of the present invention is a capsule of about 500 mg, having about 375 mg total by weight of the composition of a combination, preferably a synergistic combination, of purified *Bombyx mori* cocoon silk peptide fiber (e.g.) Peptylin®, refined *Buglossoides arvensis* seed oil (e.g. NeurXcer), and Wild Canadian (*Vaccinium angustifolium*) blueberry extract. In addition, other ingredients in the capsule include one or more of non-GMO modified food starch, non-GMO corn syrup solids, rice starch, vegetable cellulose (capsule shell), rosemary extract (anti-oxidant), natural tocopherols (anti-oxidant), ascorbyl palmitate (anti-oxidant), and natural flavors. In another embodiment, such a capsule would contain an effective amount of the active ingredients, or for instance 2 capsules would contain an effective amount of the active ingredients, and would be administered to a human daily.

In another embodiment, the compositions of this invention are for administration to humans. In an embodiment, compositions of the present invention may be administered to a subject such as a human or other animal, including for instance a companion animal, including for instance a mammal, such as a dog, cat, horse, pig, mouse, rat, or for instance a non-human primate such as a monkey, gorilla, orangutan, and so forth.

Using a small volume rather than a large dose may be beneficial, along with inducing synergistic effects through different and various mechanisms, rather than through merely additive effects through a single mechanism. For example, in the in vitro cell challenge trials described in this application, refined *Buglossoides arvensis* seed oil administered by itself did not exhibit any notable cytoprotective benefits, but in complex with the other active ingredients of the present invention, as in Formulas D and E, the cytoprotective effect substantially improved and ROS generation was substantially lowered.

A "composition" according to this invention comprises purified *Bombyx mori* cocoon silk peptide fiber and refined *Buglossoides arvensis* seed oil. The composition may comprise the fiber and oil so they are combined and taken together e.g. as a single discrete dose unit like a pill or measured amount of powder or a liquid/suspension, or e.g. two different formulations to be taken together e.g. on the same day. Optionally, said composition also comprises a Blueberry Extract and one or more other ingredients, as discussed throughout this application. A composition of the present invention may comprise, consist essentially of, or consist of, purified *Bombyx mori* cocoon silk peptide fiber and refined *Buglossoides arvensis* seed oil, optionally blueberry extract, and optionally other ingredients including for instance those expressly named in this application.

Administration of a composition of this invention to a subject is in an effective amount of the active ingredient, to effectively improve memory and/or cognitive performance, and/or provide neuroprotection, and/or support the body's natural defense against neurodegenerative diseases or a neurological condition such as dyslexia, when administered to the human. Other ingredients of compositions of this invention, and forms and routes of administration and the like, are discussed throughout this application.

An "extract" according to this invention refers to a natural substance (such as *B. arvensis* seeds or blueberries) that has been disrupted from its natural state (for instance chopped or ground or crushed or pressed) and steeped with water or other solvent(s) (e.g. oil, ethanol) and for instance specific salt, pH, and/or additional chemical components and/or exposed to elevated temperatures and pressures to form the extract. A "standardized" extract of this invention identifies specific components to characterize an extract in a specified amount or range, including for instance defined by minimum or maximum amount, so as to render the extract consistent at least with regard to those components from one batch to the next. A "standardized aqueous extract" refers for instance to an extract prepared with water as the primary solvent.

A "dietary supplement" of this invention is an addition to the human diet, which is not a natural or conventional food, which is administered orally such that the *B. mori* fiber, *B. arvensis* seed oil, optionally Blueberry Extract of this invention, including metabolites or other modifications of such by the body, reach bodily cells and tissues and other components and act on the cells and tissues and other components to effectively improve memory and/or cognitive performance, and/or provide neuroprotection, and/or support the body's natural defense against neurodegenerative diseases or a neurological condition such as dyslexia, or treat such disease or condition such as dyslexia, when administered to the human. A composition of the present invention may be a dietary supplement.

In the present invention, "treatment" and the like refers to improving a subject's neurological status, said improvement shown for instance by improved test scores (e.g. one or more of Psychomotor Speed, Reaction Time, Cognitive Flexibility, Processing Speed, Executive Function, and/or Motor Speed as tested by CNS Vital Signs) after administration of a composition of this invention, or for instance by subjective improvement as reported by the subject or for instance a guardian of the subject after administration of a composition of this invention. In an embodiment, a disease or disorder that may be treated according to this invention includes dyslexia, multiple sclerosis, memory impairment, attention deficit, forgetfulness, Alzheimer's disease, Alzheimer's dementia, vascular dementia, dementia, Parkinson's disease, depression, a sleep disorder, dysgraphia, Anxiety Disorder, ADD, ADHD, autism spectrum disorder, Asperger's, strabismus, depression, brain fog from cancer chemotherapy treatment, brain fog from COVID-19 infection, concussion, or a demyelination disease or disorder. In addition, administration of a composition of the present invention may be administered to a subject to aid recovery from a cardiovascular incident or a stroke, or from calcification of the heart and myocardial infarction.

"Purified *Bombyx mori* cocoon silk peptide fiber" according to the present invention refers to a preparation of fibroin peptides and optionally also fibroin amino acids from *Bombyx mori* L. cocoon, in one embodiment having at least 85% purified *Bombyx mori* cocoon silk peptide fiber, in one embodiment having at least 95% purified *Bombyx mori* cocoon silk peptide fiber, by weight of the preparation. Purified *Bombyx mori* cocoon silk peptide fiber is made by hydrolyzing and purifying fibroin protein and/or peptides from *Bombyx mori* L. cocoon, via enzymatic hydrolysis in an embodiment. Purified *Bombyx mori* cocoon silk peptide fiber in an embodiment of the present invention includes less than 10% by weight sericin, less than 5% by weight in an embodiment, and less than 1% by weight sericin in an embodiment. Purified *Bombyx mori* cocoon silk peptide fiber in an embodiment of this invention is at least 89% by weight fibroin, and may be present in amounts of about 90%, about 91%, about 92%, about 93%, about 94%, about 95%, about 96%, about 97%, about 98%, about 99%, or about 100% by weight. In an embodiment, enzyme hydrolysis is used to prepare purified *Bombyx mori* cocoon silk peptide fiber.

The hydrolyzed fibroin preparation is digestible and absorbed easily, in an embodiment. In an embodiment, purified *Bombyx mori* cocoon silk peptide fiber of the present invention is safe for human consumption.

Purified *Bombyx mori* cocoon silk peptide fiber according to an embodiment of the present invention is Peptylin® (purified *Bombyx mori* cocoon silk peptide fiber; BF-7®, Famenity Co., Ltd., Korea, sold as Peptylin® in the United States, Europe, South America, and Canada; also, BioGrand Co. Ltd., Korea). The preferred molecular weight range for purified *Bombyx mori* cocoon silk peptide fiber (e.g. Peptylin) is 800-1500 daltons. Purified *Bombyx mori* cocoon silk peptide fiber (e.g. Peptylin) is a water-soluble preparation of silk fibroin peptides and amino acids, easily digestible and absorbable.

Peptylin is a registered trademark of Famenity Co. Ltd. and pure silk fibroin peptide is manufactured exclusively by Famenity Co. Ltd. In an embodiment, purified *Bombyx mori* cocoon silk peptide fiber such as Peptylin® is made through the following procedure:

Silk cocoons from *Bombyx mori* are composed primarily of two proteins; fibroin, an insoluble fiber which constitutes the structural center of the silk, and sericin, a gummy protein that covers the fibroin fibers. For the manufacture of Peptylin®, the fibroin is harvested by removing the sericin coating. This process is accomplished by a series of steps that utilize heat, pressure and calcium chloride salt. This process is followed by an enzymatic digestion, that results in a minimum 95% purity of the fibroin protein. Other processes may also be used for preparing purified *Bombyx mori* cocoon silk peptide fiber according to the present invention.

In an embodiment, purified *Bombyx mori* cocoon silk peptide fiber according to the present invention may be prepared as follows: The cocoons are weighed and cut into lengths of 1-2 cm. Purified, reverse-osmosis deionized water (DI) is added to a stainless-steel reactor, equipped with mechanical stirrer and water jacket, along with the processed cocoons at a 1:10 w/v ratio. Temperature initiates at 25° C., 1 atm and is then raised to 100-105° C. and boiled for 3 hours with moderate stirring. The temperature is then cooled to 50° C., and water is removed using pressure filtration until the refined cocoons are left with ~2% water content. The weight of refined cocoons is measured, along with the assessed water content, to determine the ratio of calcium chloride and DI water for the subsequent step.

The refined cocoons are then diluted with water and calcium chloride into the reactor at a 9:55:45 (w/w/w), cocoon:$CaCl_2$:DI water. When the refined cocoons are completely immersed, the temperature is raised to 100° C. and the solution is stirred moderately for one hour. The reactor temperature is then raised to 120-125° C. with steam and stirred for 6 to 7 hours, resulting in a viscous slurry. Once the cocoon material has completely solubilized, the solution is cooled down to 80~90° C. The solution is then further diluted with DI water, ~1.3 times the initial amount, and then filtered with a 10 um microfilter. The filtered solution is desalinated using electric desalting equipment until the salinity is less than 0.3%. The refined protein is then sterilized at 95±3° C. for 30 min, then cooled to 53-55° C.

The pH is adjusted to 6.5-7.0 by addition of either ~6% $NaOH_{(Aq)}$ or acetic acid. A 1% food grade enzyme mixture of Aminopeptidases and Cellulase (w/w) is added to conduct the enzymatic hydrolysis. This solution is then held at a temperature of 53-55° C. for 24 hours. The resulting product is then sterilized at 95±3° C. for 30 min, which stops the enzymatic activity. The solution is then cooled to 50±3° C. The product is then concentrated through decompression, until the slurry viscosity reaches a 25±2 brix % at 45±5° C., 650-700 mmHg. The slurry is then sterilized again, to ensure enzyme deactivation, at 95±3° C. for 30 min and then allowed to cool to 60±3° C. The slurry is frozen at −18° C. for 18 hours, and then immediately moved to the dryer and allowed to dry at −40° C., 0.2-0.8 mmHg. Upon completion of the drying process, the dried product is milled and passed through a 40-mesh screen to yield the powdered purified *Bombyx mori* cocoon silk peptide fiber. Peptylin® is then packed in various sizes (1 kg, 5 kg, 10 kg or 20 kg) and stored at room temperature in air tight containers.

Peptylin®, in an embodiment, is a free-flowing light green to brown powder. For Peptylin®, in an embodiment, a minimum of 95% fibroin content is confirmed via analysis of the amino acid profile of the product. In some batches tested after the above preparation, mercury and cadmium were no more than 0.2 ppm, and lead and arsenic were no more than 1.0 ppm. During manufacture, a small amount of free amino acids may be released from the peptides, which include alanine and tyrosine. As these free amino acids present in higher concentrations compared to other amino acids, in an embodiment, they may be used as markers for chemistry and manufacturing controls. In an embodiment, purified *Bombyx mori* cocoon silk peptide fiber according to an embodiment of the present invention has at least one or more of the following characteristics; in an embodiment all of the following characteristics: a light green to brown powder by visual determination; not less than 90% crude protein, for instance at least 95% or 99%; not more than 10% moisture, for instance, not more than 3% or not more than 2% or not more than 1%; with heavy metals (Mercury (Hg), Lead (Pb), Cadmium (Cd), Arsenic (As)) for instance each undetectable by USP 261 or 233, or for instance each not more than 1 part per million; tyrosine present in amounts of about 2.0-12.0 mg/g (for instance, about 7 mg/g) and alanine present in amounts of about 3.0-15.0 mg/g (for instance, about 8 mg/g) as assayed by HPLC; and with a total aerobic microbial count not more than 1,000 cfu/g for instance as determined by USP 61 plate-count methods; yeas and molds not more than 100 cfu/g for instance as determined by USP 61 plate count methods; with tests for salmonella, *E. coli*, and *S. aureus* providing a negative result (not detectable), for instance per USP 62 protocols for each; and with aflatoxin summative amounts (B1, B2, G1, G2) not more than 20 parts per billion.

Purified *Bombyx mori* cocoon silk peptide fiber according to an embodiment of the present invention is orally administered to a human as a dietary supplement in an amount of about 200-600 mg per day, with about 20 mg as a lower range limit for daily administration, and up to about 5000 mg as a daily upper range limit. Amounts greater than 5000 mg, for instance 5000 mg to 10,000 mg, may be included in a composition of this invention. Compositions prepared as a discrete dose unit according to an embodiment of the present invention may include about 50-800 mg purified *Bombyx mori* cocoon silk peptide fiber; in an embodiment, about 20-2000 mg or about 20-40 mg of purified *Bombyx mori* cocoon silk peptide fiber; about 40-80 mg, about 50-100 mg, about 60-150mg, about 100-200 mg, about 150-300 mg, about 200-600 mg, about 300-500 mg, about 400-800 mg, about 200-1000 mg, about 200-2000 mg, about 50-5000 mg, about 350-400 mg, about 100-1600 mg, about 3000-4000 mg, and the like of purified *Bombyx mori* cocoon silk peptide fiber. In an embodiment, 400 mg of purified *B. mori* cocoon silk peptide fiber is included in a composition of this invention, and/or administered as a daily dose. In an embodiment, the above amounts are for daily administration of a composition of the present invention.

"Refined *Buglossoides arvensis* Seed Oil" according to the present invention refers to oil extracted from *Buglossoides arvensis* seeds. In an embodiment, oil from *Buglossoides arvensis* seeds may be prepared by pressing and/or grinding and then extracting oil from the seeds, for instance as known for such and similar seeds in the art. In an embodiment, refined *Buglossoides arvensis* seed oil is available for instance under the tradenames Ahiflower® or NeurXcel®. The seeds are from patented or patent-pending varieties of the plant species *Buglossoides arvensis* which have uniquely higher oil content, fatty acid composition, and disease resistance than wild-type varieties of the same species. The seeds are refined according to proprietary manufacturing methods by Nature's Crops International Ltd. (Kensington, PE, Canada) or its authorized agents. While there are many rich sources of plant-based omega-3 content (notably flax, chia, perilla, sacha inchi oils), and while there are even single-plant sources of omega-3-6-9 (notably hemp and echium seed oils), without being bound by theory, the uniquely rich chemical content of NeurXcel® seed oil including its biologically advanced omega-3-6-9 content contributes to NeurXcel® seed oil's unique and necessary contribution to the present invention. NeurXcel® seed oil according to an embodiment of the present invention is standardized to contain about 17-24% of stearidonic acid (c18:4, n-3) and about 40-48% of alpha-linolenic acid (c18:3, n-3) and about 4% to about 8% gamma-linolenic acid (c18:3, n-6).

In an embodiment of compositions of the present invention, NeurXcel Seed Oil Modified—Starch SDA Powder (Nature's Crops International, Kensington, PEI, Canada) is used. The powder contains microencapsulated oil from the seeds of the *Buglossoides arvensis* plant in an amount of 500 mg NeurXcel® seed oil per gram. The powder is described as white to off-white powder having a pleasant aroma and flavor and a particle size of 600 um or less (100% of particles passing through US Standard Sieve No. 30 (600 um)). The oil is described as rich in the essential fatty acids stearidonic acid (SDA) and gamma linolenic acid (GLA), and as having the following minimum fatty acid content: 18 mg/g palmitic acid; 28 mg/g oleic acid; 42 mg/g linoleic acid; 21 mg/g Gamma-linolenic acid (GLA); 198 mg/g alpha-linolenic acid (ALA); 80 mg/g stearidonic acid (SDA). In addition, the powder is described as having less than 5% moisture, cold water dispersible, less than 1000 cfu microbial total plate count/gram, less than 100 cfu yeast/mold per gram, less than 10 cfu coliforms/gram, and negative for *E. coli* and *Salmonella* spp. in 10 grams of the powder. In an embodiment, refined *Buglossoides arvensis* seed oil of this invention includes more than 80% of combined alpha-linoleic acid (c18:3, n-3), stearidonic acid (c18:4, n-3), and gamma-linolenic acid (c18:3, n-6) as part of the total ingredients comprising omega 3-6-9 fatty acids in the composition.

In another preferred embodiment, NeurXcel Seed Oil (Nature's Crops International, Kensington, Canada) is used. The fatty acid profile disclosed for the oil is as follows: Stearidonic Acid C18:4 (SDA): 17-21%; Gamma Linolenic Acid C18:3 (GLA): 4.5-8%; Alpha-Linolenic Acid C 18:3 (ALA): 42-48%; Palmitic Acid C16:0: 4-7%; Oleic Acid C18:1: 6-14%; Linoleic Acid C18:2: 9-15%.

In an embodiment, refined *Buglossoides arvensis* seed oil powder (e.g. NeurXcel seed oil powder CWD, the Wright Group, Crowley La.) according to the present invention includes one or more, and preferably all, of the following characteristics: a fine white to off-white powder having a particle size in which 100% of particles pass through a U.S. Standard Sieve No. 30 (600um), dispersible in cold water, having 50% *B. arvensis* seed oil including 25% alpha linolenic acid (ALA), 8% stearidonic acid (SDA), and 3% gamma linolenic acid (GLA). Additional ingredients may include modified starch, corn syrup solids, antioxidants, and natural flavors; moisture is less than 5%.

In the present invention, NeurXcel Seed Oil is preferably orally administered as a dietary supplement in an amount of about 20mg-10,000 mg oil per day, preferably about 100-10,000 or about 100-2500 mg per day, with about 100 mg as a preferred lower range limit for daily administration, and about 10,000 mg as a daily preferred upper range limit. In an embodiment, compositions prepared as a discrete dose unit according to the present invention may include for instance about 500-5,000 mg NeurXcel® Seed Oil; about 20-250 mg of NeurXcel® Seed Oil; about 40-500 mg, about 100-600 mg, about 60-750mg, about 100-1250 mg, about 150-1900 mg, about 200-2500 mg, about 400-600 mg, about 300-700mg, or about 400-5,000 mg of NeurXcel® Seed Oil. In an embodiment, a composition of the present invention includes about 500 mg *B. arvensis* oil, or about 500 mg *B. arvensis* oil in powdered form (for instance having about 250 mg oil per 500 mg powder). The above references to *B. arvensis* oil may also be applied to oil in powdered form, for instance as discussed throughout this application. In embodiment, the above amounts are for daily administration of a composition of the present invention.

"Blueberry extract" according to the present invention refers to an extract obtained from blueberries (*Vaccinium* spp.; i.e. from species of the genus *Vaccinium*). In an embodiment, blueberries may be disrupted for instance by crushing or pureeing and then water or another liquid applied to extract substances from the blueberries, for instance as known for blueberries and other berries in the art. In an embodiment, a 36:1 standardized blueberry extract (36 grams of blueberries correspond to 1 gram of blueberry extract) is used. In another embodiment, a 75:1 standardized blueberry extract (75 grams of blueberries correspond to 1 gram of blueberry extract) is used. (BLUE D'oR, Villeroy, Canada). Another Blueberry extract of this invention is the American Blueberry (*Vaccinium corymbosum*) extract (Vita-Blue®), a powder from Futureceuticals.

In an embodiment, a composition of the present invention includes about 25-2000 mg Blueberry extract, including for instance about 50 mg to about 150 mg or about 50 mg to about 2000 mg, or about 100 mg to about 500 mg Blueberry extract. Similarly, a Blueberry extract of this invention is administered in an amount of about 50 to about 500 mg per day, for instance in an amount of about 50 mg—about 2000 mg, or about 50-500 mg, or about 100 to about 150 mg per day.

Recent work to develop Haskap blue honeysuckle (*Lonicera caerulea*) berries in North America and Northeastern Asia, containing levels of bioavailable anthocyanins considerably higher than typical blueberries, and with indications of memory enhancement properties, includes this species of berries and preparations thereof as a potential replacement for blueberry extract in the present invention, or as an additional preferred ingredient. However, this inclusion is not intended to indicate that anthocyanins alone provide the beneficial, synergistic effects seen with blueberry extract in this application. Rather, as discussed in the Examples, concentrated wild Canadian blueberry powder performed very well in tests of the present invention as compared with concentrated American blueberry, although the Canadian blueberry powder contains approximately 120× fewer anthocyanins than the American blueberry powder.

Other ingredients

Compositions of the present invention, in addition to purified *Bombyx mori* cocoon silk peptide fiber, refined *Buglossoides arvensis* seed oil, and optionally blueberry extract, in other embodiments may further comprise one or more of the following ingredients: Acetyl-L-Carnitine, L-theanine, L-serine, Zinc (as zinc glycinate, zinc gluconate, zinc citrate, or zinc picolonate), Huperzine A extracted from *Huperzia chinensis*, *Bacopa monnieri* extract, Ginseng Extracts, Citicoline, Ginger (*Zingiber officinalis*) Extracts, *Ginkgo biloba* extract, Folic acid, Vitamin B12, Vitamin B6, Vitamin B1, and/or Vitamin D3 (cholecalciferol), Green Mountain Tea (*Sideritis* app.), Lion's Mane mushrooms. Each of these is briefly discussed below, some in preferred groupings. Other ingredients are also noted throughout the application.

Multipath Memory Grouping

Each of the ingredients discussed below—Acetyl-L-Carnitine, Huperzine A extracted from *Huperzia chinensis*, *Bacopa monnieri* extract, Ginseng Extracts, Citicoline, *Ginkgo biloba* extract—may be added to a composition according to the present invention as a preferred embodiment. However, in another preferred embodiment, all of these ingredients would be administered together as part of the composition of the present invention, for instance in the same discrete dose unit, or for instance in separate dose units on the same day, in the preferred dosages provided below.

Acetyl-L-Carnitine

Acetyl-L-carnitine is a substance which is naturally produced and used in the body. Supplements are therefore taken when it is deficient. This substance maximizes the generation of neural energy in the neural cells and, as an antioxidant, it plays various roles, including cellular recycling and respiration of the mitochondria. Also, acetyl-L-carnitine increases nerve growth factor (NGF) value, which is an important brain recovery complex. NGF protects cholinergic neurons in the central nervous system and helps to provide the appropriate level of choline acetyltransferase (ChAT). Furthermore, it has been used to counter neurodegenerative diseases as a medical product in several countries, including Korea. Acetyl-L-carnitine showed a beneficial effect on both cognitive impairment and early-stage Alzheimer's Disease in double-blind, placebo-controlled clinical studies. Useful results were seen in the Logical Memory, Trail Making Test, Hooper test, and brain waves in a study on patients (severely epileptic patients) compared to the placebo group.

In the present invention, acetyl-L-carnitine is preferably administered in an amount of about 200-2000 mg per day; more preferably, about 300-800 mg per day. Compositions of the present invention preferably include this dosage.

Bacopa monnieri Extract

Bacopa is one of the most frequently used health/functional food ingredients for memory improvement. It has previously been employed in India and Southeast Asia. The main active ingredients of the Bacopa extract are bacosides A and B, which have a variety of memory-related mechanisms. They are known to inhibit acetylcholinesterase (AchE), activate choline acetyltransferase (ChAT), and promote antioxidant activity and brain blood flow. The functions of the Bacopa extract are supported by extensive clinical evidence. For example, while a previous study on the memory improvement of healthy elderly people reported it to significantly improve memory gain and maintenance, another on seniors suggested it inhibits plasma AchE activity, resulting in improvements in attention, cognitive processing, and working memory. However, some studies mention its low solubility and emphasize the need for further research to improve its bioavailability. In a composition of the present invention, the standardized Bacopa extract product obtained from the Bacopa monnieri root and that contains 20-60% Bacosides content, is appropriate.

In the present invention, Bacopa monnieri extract is preferably administered in an amount of about 50-300 mg per day; more preferably, about 100-200 mg per day. Compositions of the present invention preferably include this dosage.

Ginseng Extracts

Ginseng extract is traditionally used in the East and is mainly comprised of saponin glycosides. It is reported to have a variety of pharmacological roles, including anti-fatigue, work performance enhancement, and hypoglycemic agent functions. Ginsenosides, such as Rb1, are generally contained in Panax ginseng extract and are recognized to promote the choline acetyltransferase (ChAT) activity, which is important for acetylcholine synthesis. A major clinical study on memory improvement associated with the Ginseng comprises Ginkgo biloba extract, which may be included in compositions of the present invention, which was successful in 2506 subjects. In concordance, it was also found to help working memory. Similarly, American ginseng was described to improve working memory and calmness in people. In this composition, Panax ginseng extract obtained from either the Panax ginseng or the Panax quinquefolius roots is appropriate.

In the present invention, ginseng extract is preferably administered in an amount of about 100-500 mg per day; more preferably, about 100-200 mg per day. Compositions of the present invention preferably include this dosage. Also, Ginkgo biloba extract may be used in an amount for instance as in the major clinical study mentioned above.

Citicoline

Citicoline has been widely used as a nutritional supplement ingredient for memory improvement as a substance that naturally occurs within the cells in the body. Citicoline is known to help memory in various ways, such as through its neural protection effects, increases in the amount of choline used in acetylcholine synthesis, and in improvement in cellular communication by increasing the utility of human neurotransmitters. Previous clinical studies showed it to improve memory in elderly people. Specifically, participants who consumed drinks including citicoline were found to have a much faster maze learning time, error reduction, and a higher information processing speed.

In the present invention, citicoline is preferably administered in an amount of about 250-2000 mg per day; more preferably, about 300-1000 mg per day. Compositions of the present invention preferably include this dosage.

Ginkgo biloba extract

Ginkgo biloba extract is a material that is obtained from the leaves of the Ginkgo tree, then processed and standardized. It has been widely used for decades to treat brain function impairments, memory loss, and dizziness.

Ginkgo extract is recognized to protect brain cells and to promote brain blood flow. Additionally, it participates in the pre-synaptic choline uptake and acetylcholine release, while it upregulates the post-synaptic acetylcholine muscarinic receptor. Although research on some small partial effects of Ginkgo exists, most investigations reported positive results. Similarly, although several clinical studies are present, all the referred papers consistently show that Ginkgo helps memory improvement. In particular, a previous clinical study indicated a significant memory improvement effect from low doses of 3 administrations of 19.2 mg per day. Moreover, it is categorized as a medical product in Korea and recognized as effective on memory reduction and for attentional disorders. Ginkgo extract may be obtained from Ginkgo biloba leaf, purified, and standardized. In an embodiment of this invention, a material that contains about 24% Ginkgo flavonoids and 6% triterpene lactones, which is appropriate under the USP pharmacopeia, is used.

In the present invention, Ginkgo biloba extract is preferably administered in an amount of about 60-240 mg per day; more preferably, about 100-150 mg per day. Compositions of the present invention preferably include this dosage.

Active Vitamin Blend

This is a blend of water-soluble vitamins comprised of Folic acid, Vitamin B12, Vitamin B6, and Vitamin B 1, which affects memory and neural protection both directly and indirectly. Specifically, the active form of each vitamin with a high absorption rate and support for brain performance is desirable. Furthermore, the blend above evenly blocks the homocysteine synthesis mechanism, which has adverse effects on many organs (including the brain) and efficiently blocks homocysteine, which is a known cause of neural brain damage, delays communication between cranial nerves, and brain contraction. It can be an essential prescription either for people with weak homeostenosis at stressful situations or elderly people. Finally, it can be used as part of a composition of the present invention in combination with the Multipath Blend above, or without.

Each of the ingredients discussed below—Folic acid, Vitamin B12, Vitamin B6, and Vitamin B1—may be added to a composition according to the present invention as a preferred embodiment. However, in another preferred embodiment, all of these ingredients would be administered together as part of the composition of the present invention, for instance in the same discrete dose unit, or for instance in separate dose units on the same day, in the preferred dosages provided below.

Active Folic acid (5-Methylfolate)

Folic acid, also referred to as vitamin B9, is a water-soluble vitamin that participates in red blood cell synthesis, nucleic acid synthesis, and fetal development. Deficiency can occur due to malabsorption, low consumption, and an increase in demand. Folic acid plays a role in homocysteine methylation, providing the methyl group that converts methionine into s-adenosyl methionine during brain function and reducing homocysteine. Moreover, a previous clinical study described folic acid administration tends to improve memory and attention. In contrast, subjects with low folic acid values showed impairments in both word and object recall tasks. Supplementation of vitamin B12, vitamin B6, and folic acid had a positive impact on partial memory capacity measures. In this composition, folic acid can either be present in its natural condition (i.e., polyglutamate folate), in its synthetic state (i.e., monoglutamate folate) or its active form (i.e., 5-methyltetrahydrofolate). Preferably, 5-methyltetrahydrofolate is used.

In the present invention, folic acid is preferably administered in an amount of about 0.065-1 mg per day; more preferably, about 0.4 mg per day. Compositions of the present invention preferably include this dosage. Also, the active form of folic acid (5-Methylfolate) is preferably administered in an amount of about 1-15 mg per day; more preferably 2-7.5 mg dosage per day.

Active Vitamin B12 (Cobalamin)

Vitamin B12, also referred to as cobalamin, is a type of water-soluble vitamin that plays various roles, including metabolic support, generation of neurons, DNA, RNA, and red blood cells, prevention of dementia, and mental health. Deficiency in vitamin B12 commonly occurs in people with an unhealthy diet, elderly people, and vegetarians. Vitamin B12 functions as an essential co-factor of the one-carbon cycle for the synthesis of neurotransmitters, such as acetylcholine. It activates methionine synthase within the methionine cycle and reduces the amount of homocysteine. A clinical study revealed that low consumption of vitamin B12, vitamin B6, and folic acid could increase the probability of MCI/dementia. Additionally, a low concentration of vitamin B12 is associated with low memory capacity. In this composition, vitamin B12 can be used in either its general forms (i.e., cyanocobalamin and hydroxycobalamin) or active forms (i.e., methylcobalamin and adenosylcobalamin). Methylcobalamin has the highest biological activity and is preferably used.

In the present invention, vitamin B12 in its active form, methylcobalamin, is preferably administered in an amount of about 0.5-6 mg per day; more preferably, about 1-4 mg per day. Compositions of the present invention preferably include this dosage.

Active Vitamin B6 (Pyridoxal 5'-phosphate)

Vitamin B6, also referred to as Pyridoxine, is a water-soluble vitamin that participates in the metabolism of nutrients, such as several amino acids, the synthesis of red blood cells and neurotransmitters, and in gene expression. Although rare, vitamin B6 deficiency can occur due to hyperthyroidism, excessive consumption of proteins, and abuse of antibiotics. Vitamin B6 is an essential cofactor of the folate cycle and activates cystathionine β-synthase, which synthesizes the generated homocysteine into attenuated substances, such as cysteine. With regards to the clinical evidence, clinical evaluation described vitamin B6 supplements to improve information retention considerably. In fact, vitamin B12, vitamin B6, and folic acid supplements were shown to have a considerable positive influence on some memory capacity measures. Low consumption of vitamin B12, vitamin B6, and folic acid can increase the probability of MCI/dementia. In this composition, Vitamin B6 can be used as pyridoxine, pyridoxal, pyridoxamine, or the phosphorylated form of each. Desirably, Pyridoxal 5'-phosphate, which has the highest biological activity, should be used.

In the present invention, vitamin B6 in its active forms (Pyridoxal 5'-phosphate) is preferably administered in an amount of about 20-100 mg per day; more preferably, about 30-80 mg per day. Compositions of the present invention preferably include this dosage.

Active Vitamin B1 (Benfotiamine)

Vitamin B1, also referred to as thiamine, is a supportive enzyme that participates in many stages of body sugar metabolism by converting it into thiamine pyrophosphate. Considering that all cells require energy, thiamine deficiency can affect all organs. However, thiamine is not produced by the body and does not have a large reservoir. Therefore, its low consumption can result in thiamine deficiency within a few weeks to months. The role of thiamine in the brain in the generation of pyruvate dehydrogenase, an essential enzyme in the generation of acetylcholine, is of crucial importance. Wernicke syndrome is a nervous system disorder related to thiamine deficiency which results in the paralysis of the eye muscles due to functional impairments in the diencephalon and midbrain, decreased ability to walk, and dysfunction in consciousness. This condition progresses to the Korsakoff syndrome if not treated promptly, which is a continuous memory and learning disorder. In this composition, Vitamin B1 has the general form of thiamine as well as the active forms of benfotiamine and fursultiamine. Preferably, the active form is used.

In the present invention, vitamin B1 in its active form (Benfotiamine) is preferably administered in an amount of about 5-100 mg per day; more preferably, about 25-50 mg per day. Compositions of the present invention preferably include this dosage.

COMPOSITIONS

Compositions of the present invention are defined throughout the entire application. Compositions of the present invention are shown in the various Examples to provide synergistic effects. The lack of a specific assertion of synergy or synergistic effect this application or lack of a notation of statistical significance including in any given Example is not intended to indicate a lack of synergy or statistical significance, unless expressly indicated as such. Further statistical analyses may be carried out based on the data in the Examples as needed.

A composition according to the present invention comprises purified *Bombyx mori* cocoon silk peptide fiber and refined *Buglossoides arvensis* seed oil, and optionally also comprises blueberry extract. In one embodiment, the purified *Bombyx mori* cocoon silk peptide fiber is Peptylin®, the refined *Buglossoides arvensis* seed oil is NeurXcel® Seed Oil in the form of a micro-encapsulated powder providing a 50% NeurXcel® oil payload in a modified starch matrix or is in the form of liquid oil. The Blueberry extract is North American and/or wild Canadian blueberry extract, in some embodiments of this invention. Other pharmaceutically acceptable ingredients or additives may also be included in the present compositions, for instance as described throughout this application.

A composition of the present invention may include refined *Buglossoides arvensis* seed oil to purified *Bombyx mori* cocoon silk peptide fiber in a mass balance ratio of from about 0.1:1 to 10:1. In another embodiment, said ratio is from about 0.4:1 to 5:1. In another embodiment, said ratio is about 2.5:1 to 0.625:1. This factors in non-active micro-encapsulation carriers. In another embodiment, said ratio of active ingredients is about 0.1:1, 0.4:1, 0.625:1, 2.5:1, or 5:1.

Ratios of blueberry powder w/w to the other capsule ingredients (e.g. *B. mori* fiber and *B. arvensis* oil) may be in a ratio of about 1:20 to about 1:6 (about 5.3% w/w to about 16.7%) in BrainiLex® powder. In the Braini® powder, typically the blueberry extract powder is about 4%. In general, in a composition of this invention, a blueberry extract powder may be about 2% w/w of the composition to about 40%.

In an embodiment of the present invention, a composition for oral administration comprises the following: purified *Bombyx mori* cocoon silk peptide fiber (Peptylin®) and refined *Buglossoides arvensis* seed oil, optionally Blueberry Extract, as well as one or more of the following: *Bacopa monnieri* extract, Huperzine A extracted from *Huperzia chinensis*, Acetyl-L-carnitine, *Panax ginseng* extract, Citicoline, *Ginkgo biloba* extract, active Folic acid (5-Methylfolate), active Vitamin B12 (Cobalamin), and active Vitamin B6 (Pyridoxine aka Pyridoxal 5'-phosphate); in another embodiment, all of the above are included in the composition.

In an embodiment of the present invention, a composition for oral administration comprises the following: purified *Bombyx mori* cocoon silk peptide fiber (Peptylin) and refined *Buglossoides arvensis* seed oil, optionally, wild Canadian Blueberry (*Vaccinium angustifolium*) extract, as well as one or more of the following: rice starch, maltodextrin, vegetable cellulose (if the composition is formulated in capsule form), vegetable starch, corn syrup solids, natural flavor, mixed tocopherols, ascorbyl palmitate; in another preferred embodiment, all of the above are included in the composition. In other embodiments, such as the Braini® formulation discussed in the in vivo Examples, other ingredients may include non-GMO modified food starch, non-GMO corn syrup solids, rice starch, vegetable cellulose (capsule shell), rosemary extract (anti-oxidant), natural tocopherols (anti-oxidant), ascorbyl palmitate (anti-oxidant), natural flavors.

In an embodiment of the present invention, a composition for oral administration to improve cognitive performance among dyslexic and/or dyspraxic individuals comprises the following: purified *Bombyx mori* cocoon silk peptide fiber (Peptylin®) and refined *Buglossoides arvensis* seed oil, wild Canadian Blueberry extract or North American Blueberry (*Vaccinium corymbosum*) extract, as well as one or more of the following: Zinc (as zinc citrate, zinc glycinate, zinc gluconate, or zinc picolonate); and docosahexaenoic acid (DHA) derived from *Schizochytrium* spp algae.

In an embodiment of the present invention, a composition comprises 400 mg Peptylin, 500 mg NeurXcel® seed oil in powdered form, and 100 mg Blueberry extract. In an embodiment, this composition is administered, for instance in one or more discrete dose units, daily to a subject.

These and other preferred components are more clearly defined below, and the basis of the pharmacological effects of each component on memory improvement is mentioned based on clinical trials. Table 1 discloses some embodiments of compositions of the present invention:

TABLE 1

| Servings 2-4/day | Scale (mg/capsule) | Pr. 8 | Pr. 9 | Pr. 10 | Pr. 11 | Pr. 12 | Pr. 13 | Pr. 14 | Pr. 15 | Pr. 16 | Pr. 17 |
|---|---|---|---|---|---|---|---|---|---|---|---|
| Compositions of present invention | PEPTYLIN® | 100 | 200 | 100 | 100 | 100 | 200 | 200 | 200 | 100 | 100 |
| | NeurXcel® seed oil | 125 | 250 | 125 | 125 | 125 | 250 | 250 | 250 | 125 | 125 |
| | Blueberry | 25 | 50 | 25 | 25 | 25 | 50 | 50 | 50 | 25 | 25 |
| Multipath Memory Blend | Acetyl-L-carnitine | 125 | | 125 | 125 | 125 | | | | | 125 |
| | Bacopa | 50 | | 50 | 50 | 50 | | | | 50 | 50 |
| | Panax Ginseng | 50 | | 50 | 50 | 50 | | | | 50 | 50 |
| | Citicoline | 125 | | 125 | 125 | 125 | | | | | 125 |
| | Ginkgo extract | 30 | | 30 | 30 | 30 | | | | 30 | 30 |
| Active Vitamin Blend | 5-Methylfolate | 1.25 | 2.5 | | 1.25 | | 2.5 | | | 1.25 | 1.25 |
| | Methylcobalamin | 0.75 | 1.5 | | 0.75 | | 1.5 | | | 0.75 | 0.75 |
| | Pyridoxal 5'-phosphate | 15 | 30 | | 15 | | 30 | | | 15 | 15 |
| | Benfotiamine | 12.5 | 25 | | 12.5 | | 25 | | | 12.5 | 12.5 |
| Excipients | MCC Silicon dioxide Magnesium stearate HPMC capsule Others | qs | qs | qs | qs | qs | Qs | qs | qs | qs | qs |

The above preparations ("Pr.") represent compositions according to the present invention. Preparations described herein are not intended as limiting. Various other preparations are possible according to the present invention, including the full variety of dosing ranges indicated above.

A composition according to the present invention is in one embodiment orally administered. A composition of the present invention may be formulated into nutraceutical or pharmaceutical dosage forms comprising for instance tablets, capsules, powders, liquids, chewables such as gummies, transdermals, injectables, dietary supplements, topical creams, lozenges, pills, and so forth. In one particular embodiment, a composition of the present invention is formulated into a gummi blend. In another embodiment, a composition is formulated into a dual capsule form, comprising powdered active ingredient(s) in an inner capsule, surrounded by liquid ingredient(s) in an outer capsule. A composition of the present invention may further comprise one or more excipients, additives, and/or other substances.

In an embodiment, a composition of this invention is a synergistic composition, Braini®. Braini® is a bulk blended dietary supplement powder comprising Peptylin® powder (with 1 gram of Braini® powder providing about 400 mg Peptylin(®); NeurXcel® oil microencapsulated powder (with 1 gram of Braini® powder providing about 500 mg NeurXcel® oil encapsulated powder); and Blueberry extract powder (*Vaccinum corymbosum*) (with 1 gram of Braini® powder providing about 100 mg Blueberry extract powder, BLUEd'Or, with a ratio of 75:1 frozen fresh blueberries: powder). 500 mg NeurXcel® microencapsulated powder includes about 250 mg NeurXcel® oil and about 250mg of microencapsulated powder composed primarily of modified food starch, corn syrup solids, antioxidants, and natural flavors. 1 gram of the Braini® powder contains a complete daily intake of plant-based omega-3-6-9 fatty acids in a daily dose.

Compositions of the present invention provided synergistic results in vitro as discussed for instance throughout this application and Examples 1-13. Also, synergistic effects of the present invention are apparent for instance as compared with a Korean study which, evaluating Peptylin® (BF-7) as compared with placebo, showed improved CTT (reaction time) scores in healthy children. BF-7 achieved a 23% improvement in reaction time compared with placebo (p<0.05). By comparison, Example 19 of the present application shows that in the administration of Braini® to healthy young adults, 11 of 13 subjects receiving active product improved their SAT-RT (shifting attention test, correct response reaction time) by a group average of 84 milliseconds, compared to the placebo group in which only 10 of 18 subjects improved their SAT-RT for a group average of only 2.5 milliseconds. The improvement in the active Braini® cohort was highly statistically significant (p<0.007). As a numeric percentage improvement compared with the placebo cohort, 84 milliseconds vs. 2.5 milliseconds is a remarkable improvement in reaction time, greater than 3300%. Although the CNS Vital Signs test suite is different than the Color Trails Making Test used in the BF-7 study, both test suites are well-recognized standardized measures of cognitive performance. Further, the BF-7 and Braini® trails used the same active dose of BF-7 (aka Peptylin®) at 400 mg/day, however the BF-7 trial was carried out over 16 weeks, while the Braini® trial was carried out over only 4 weeks. This outcome shows that Braini® synergistically outperforms BF-7 alone in terms of standardized controlled clinical trial reaction time outcomes compared with placebo.

As mentioned above, in an embodiment, Braini® powder is enclosed in capsules ("Braini® capsules"). In an embodiment, the capsules are made of HPMC (hydroxypropyl methylcellulose), and hold about 500 mg of powder, so that an average daily dose for a human adult (1 gram Braini® powder) may be administered with 2 capsules/day. In an embodiment, the Braini® powder is added to capsules in smaller amounts, so that 3 or 4 capsules/day are needed to administer the above daily amount, but also so that smaller amounts may be administered for instance to children or others that may be administered a smaller dose. Braini® capsules were orally administered to humans in all in vivo Examples below, providing daily amounts of 400 mg Peptylin®, 500 mg NeurXcel® microencapsulated powder (including 250 mg NeurXcel® seed oil), and 100 mg *Vaccinium corymbosum* Blueberry extract powder (BLUEd'Or, with a ratio of 75:1 frozen fresh blueberries:powder). As indicated above, a daily dose of a composition of this invention may be greater than 1 gram, for instance to accommodate increased doses of required ingredients (*B. mori* fiber (Peptylin® and NeurXcel® oil) and/or other ingredients, excipients, and the like. In an embodiment, Peptylin® and Blueberry extract of this invention are at least 95% pure, preferably at least 97-99% pure, without additional ingredients.

In an embodiment, a composition of this invention is a synergistic composition, "Braini Lex®". Braini Lex® is a bulk blended dietary supplement powder comprising Peptylin® powder (about 400 mg Peptylin® per recommended daily dose); NeurXcel® microencapsulated powder (about 500 mg NeurXcel® oil encapsulated powder per recommended daily dose); Blueberry extract powder (*Vaccinium corymbosum*) (about 100 mg Blueberry extract powder per recommended daily dose; where the extract powder is BLUEd'Or, with a ratio of 75:1 frozen fresh blueberries:powder); as well as about 100 mg algal docosahexaenoic acid (DHA) and about 25 mg zinc glycinate. 500 mg NeurXcel® microencapsulated powder includes about 250 mg NeurXcel® oil and about 250mg of microencapsulated powder composed primarily of modified food starch, corn syrup solids, antioxidants, and natural flavors. The above amounts represent a preferred daily dose of Braini Lex® for a human adult. 500 mg NeurXcel® microencapsulated powder includes 250 mg NeurXcel® oil and 250mg of microencapsulated powder composed primarily of modified food starch, corn syrup solids, antioxidants, and natural flavors. The Braini Lex® powder contains a complete daily intake of plant-based omega-3-6-9 fatty acids in a daily dose.

In an embodiment, Braini Lex® powder is enclosed in capsules ("Braini® capsules"); for instance HPMC capsules as discussed above, with total powder taken as a daily dose adjusted to accommodate the addition of algal DHA (e.g. Algarithm) and zinc glycinate (e.g. Novotech Nutraceuticals).

In an embodiment, a composition of the present invention (including but not limited to Braini® powder, Braini® capsules, Braini Lex® powder, Braini Lex® capsules) may be administered in an amount of about 10mg-600 mg total composition per kg body weight. In an embodiment, bulk powders are administered in amounts of about 50-600 mg/kg body weight, and in another embodiment, capsules are administered in amount of about 12.5 to 150 kg/body weight. The upper limits to these ranges may include for instance about 3 tablespoons of Braini® or Braini Lex® bulk powder in a child's daily dose. A child's daily dose may be the size of an adult dose or, for instance a reduce amount, such as about 10% to 90%, about 30%-70%, or about 50% of an adult dose.

In an embodiment, a composition of the present invention includes an agglomerate of purified *Bombyx mori* cocoon silk peptide fiber and refined *Buglossoides arvensis* seed oil, and optionally a Blueberry Extract. In an embodiment, the agglomerate is of purified *Bombyx mori* cocoon silk peptide fiber in powdered form, refined *Buglossoides arvensis* seed oil in microencapsulated powdered form, and Blueberry Extract in powdered form, for instance as used in the Braini® compositions described above. In an embodiment, the agglomerate is formed by mixing the above-mentioned constituents together, such that the agglomerate shows chemical and physical changes and different properties from the constituents alone. Agglomerates according to the present invention are shown for instance by scanning electron micrograph and HPLC mass spectrometry, discussed in Examples 22 and 23, below.

In an embodiment, a composition of the present invention has a shelf-life of about 1-2 years. In an embodiment, the shelf-life for Braini® or Braini Lex® powder or capsules is about 18 months. The present invention may be further understood in connection with the following Examples and embodiments. The following non-limiting Examples and embodiments described throughout this application are provided to illustrate the invention.

EXAMPLES

The aforementioned experimental ingredients were confirmed to result in memory improvements in clinical trials. The inventors have conducted in vitro and in vivo experimental trials to understand optimal interactions and synergies in various formulated compositional ratios, as shown in the following examples.

In Vitro Tests

Examples 1-5 disclose the first scientific finding of human SH-SY5Y neural cell challenge recovery improvements resulting from combining purified *Bombyx mori* cocoon silk peptide fiber with refined *Buglossoides arvensis* seed oil and other components. The use of human SH-SY5Y cell cultures as models for neurological systems and for instance neurodegenerative disorders has been published. [71-74]. Please also refer to references listed below.

The tests in Examples 1-5 were designed to mimic the effects of excessive oxidation of human neural cells, and assess neuroprotective or neurotoxic action by compositions defined by Formulas A-E. Formulas A-E are as shown in Table 2 for Examples 1-5. Formulas B-E describe compositions according to the present invention. The formulation is liquid. Peptylin®, *Aframomum melegueta* extract, and Blueberry Extract are powders, and refined *Buglossoides arvensis* seed oil is liquid. For example, for Sample A, 50 mg is prepared by dissolving in 1 ml DMSO. Dilute with Media to set final test concentration. The above method is common in in vitro tests using cell lines.

Example 1

Cell Viability Test

SH-SY5Y (neuroblastoma) cells, from a human body-derived cell line obtained from Korean Cell Bank (Seoul, South Korea) were cultured in 100 ml 10% FBS/MEM (Gibco, US), $5\times10^4$ cells/well in 96-well plates for 24 hours (3TC, 5% $CO_2$). The 10% FBS/MEM was removed and 1% FBS/MEM added to the cells. Composition A, B, C, D, or E was administered. The concentration of each component of Compositions A-E is listed in Table 2 below. Normally, cells are grown for 1-2 days in 10% FBS/MEM. Subsequently, it is replaced with 1% FBS/MEM and stabilized for one day before processing samples.

Cell viability studies were conducted using MTT colorimeter analysis. Cells were cultured for four hours after the administration of the MTT solution (3-(4,5-dimethylthiazol-2-yl)-2,5-diphenyltetrazolium bromide) (Invitrogen/ThermoFisher, Carlsbad Calif., USA). Because of an enzyme in the mitochondria of a surviving cell, tetrazolium unlinks and changes into formazan. The resulting color significantly correlates to the number of living cells, with a deeper/darker color indicating more viable cells than a lighter color. Color was quantified by measuring absorbance with a 570 nm spectrophotometer/well-plate reader. Amounts of sample treatment applied were 10 ul per well.

TABLE 2

| Compositions | | | | |
|---|---|---|---|---|
| Composition | PEPTYLIN® (Purified *Bombyx mori* cocoon silk peptide fiber) (μg) | B. arvensis Seed Oil (μg) | Aframomum melegueta Extract (μg) | Blueberry Extract (μg) |
| Form. A | 20 | 0 | 0 | 0 |
| Form. B | 20 | 50 | 2.5 | 0 |
| Form. C | 20 | 50 | 5 | 0 |
| Form. D | 20 | 50 | 0 | 2.5 |
| Form. E | 20 | 50 | 0 | 5 |

In FIG. 1, dilutions are shown in column bars from left to right: 1.00 (undiluted composition), 0.500, 0.250, 0.125, 0.0625. Dilutions were based on the above composite; compositions re-generated by concentration. As shown in FIG. 1, the results indicated no cytotoxicity was present in any of the dilution ratios (1–0.0625) of Compositions A-E.

Example 2

Evaluation of Improvement in SH-SY5Y Neuroblastoma Cell Viability in the Presence of Compositions of the Present Invention, in an Oxidative Environment ($H_2O_2$ Exposure)

SH-SY5Y neuroblastoma cells were incubated with 100 μl of 10% FBS/MEM in a $5\times10^4$ cells/well 96-well plate and cultured 24 hours, as in Example 1. The 10% FBS/MEM was removed and 1% FBS/MEM added to the cells. Composition A, B, C, D, or E was administered to the wells. Normally, cells are grown for 1-2 days in 10% FBS/MEM. Subsequently, it is replaced with 1% FBS/MEM and stabilized for one day before processing samples. Cell room condition is 3TC, 5% $CO_2$.

After 4 hours, $H_2O_2$ (a toxicity-inducing substance) was administered. In this experiment, 0.25 uM was treated and the MTT test solution used to evaluate cell viability, as in Example 1. MTT assay was performed by adding MTT solution without removal.

Figure 2:
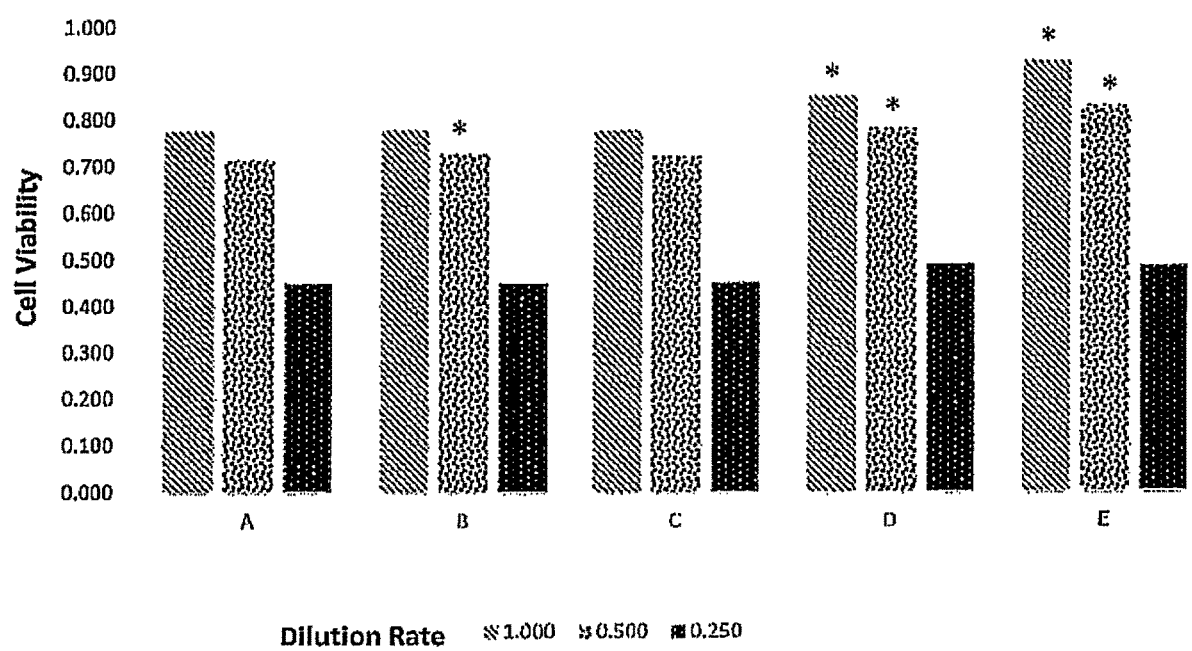
FIG. 2 is a graph showing synergistic in vitro neuroprotective effects of compositions of the present invention (B-E), as compared with purified *Bombyx mori* cocoon silk peptide fiber alone (A), following hydrogen peroxide ($H_2O_2$)-induced damage to neurons.

In FIG. 2, dilutions are shown in column bars from left to right: 1.00 (undiluted composition), 0.5, 0.25. An "*" indicates statistical significance and synergistic effect when compared with Formulation A; $p<0.05$ by Student's t-test. As shown in FIG. 2, Formulas B-E showed improved cell viability compared to Formula A, with Formulas D and E showing statistically significant improvement as compared with Formula A across 2 dilutions, and Formula B showing statistically significant improvement across 1 dilution. An increase in cell viability in an oxidative environment signifies that brain cells can be protected through an antioxidant mechanism.

Example 3

Evaluation of Improvement in SH-SY5Y Neuroblastoma Cell Viability in the Presence of Compositions of the Present Invention, in an Oxidative Environment ($FeSO_4$ Exposure)

SH-SY5Y neuroblastoma cells were incubated with 100 μl of 10% FBS/MEM in a $5\times10^4$ cells/well 96-well plate and cultured 24 hours, as in Example 1. The 10% FBS/MEM was removed and 1% FBS/MEM added to the cells. Composition A, B, C, D, or E was administered to the wells.

After 4 hours, $FeSO_4$ (a toxicity-inducing substance) was administered. In this experiment, 2.5 uM was treated and the MTT test solution used to evaluate cell viability, as in Example 1. MTT assay was performed by adding MTT solution without removal.

Figure 3:
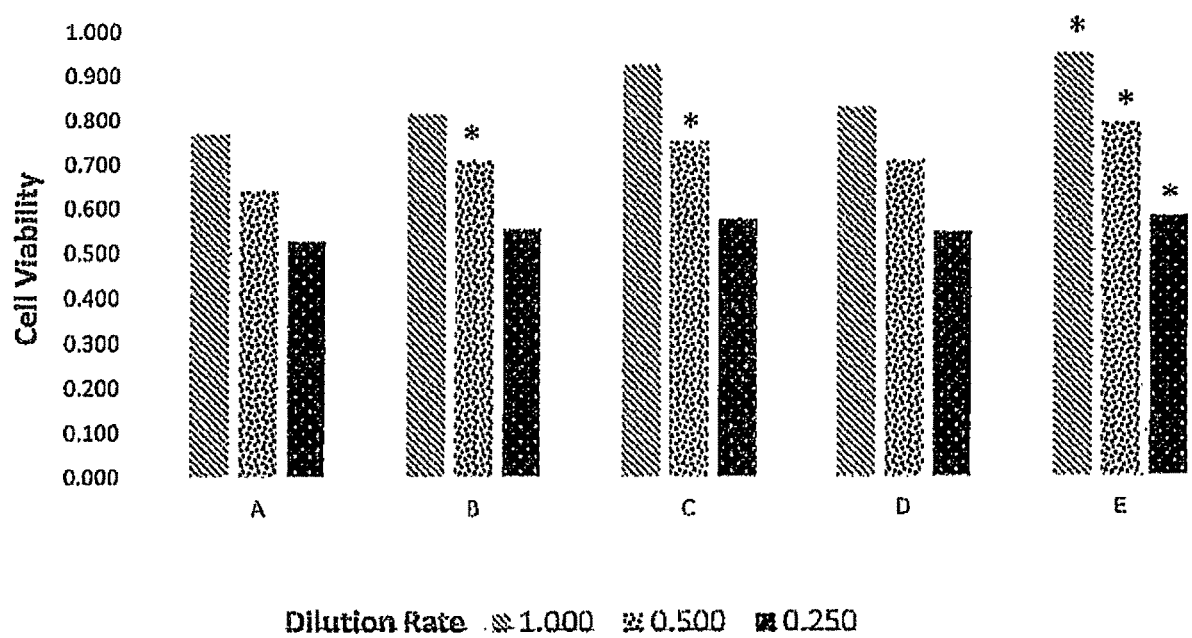
FIG. 3 is a graph showing synergistic in vitro neuroprotective effects of compositions of the present invention (B-E), as compared with purified *Bombyx mori* cocoon silk peptide fiber alone (A), following iron sulfate ($FeSO_4$)-induced damage to neurons.

In FIG. 3, dilutions are shown in column bars from left to right: 1.00 (undiluted composition), 0.5, 0.25. An "*" indicates statistical significance and synergistic effect when compared with Formulation A; $p<0.05$ by Student's t-test. As shown in FIG. 3, compositions B-E showed improved cell viability compared to composition A, similar to Example 2. Formula E shows statistically significant improvement across all 3 dilutions shown, and Formulas B and C show statistically significant improvement across the second dilution. This confirmed the consistent tendency for concentration-dependent cell protective effects in other oxidated environments.

Example 4

Evaluation of the Inhibition of Active Oxygen Production within SH-SY5Y Neuroblastoma Cells by Compositions of the Present Invention (Oxidative Environment by $H_2O_2$ Administration)

Reactive Oxygen Species (ROS) within cells can be quantified by indexing using the fluorescent probe 2',7'-dichlorofluroescin diacetate (DCF-DA) (Sigma-Aldrich, USA). When oxidized to the reactive oxygen metabolite, the DCF-DA can be excited at 485 nm and releases fluorescence at 530 nm.

SH-SY5Y neuroblastoma cells were incubated with 100 μl of 10% FBS/MEM in a $5 \times 10^4$ cells/well 96-well plate and cultured 24 hours, as in Example 1. The 10% FBS/MEM was removed and 1% FBS/MEM added to the cells. Composition A, B, C, D, or E was administered, and then DCF-DA in keeping with the DCF-DA assay described above.

After 4 hours, a 0.25 uM solution of $H_2O_2$ (a toxicity-inducing substance) was administered. Incubation time was for 2 hours before fluorescence test. Subsequently, fluorescence was measured at 530 nm to assess the level of active oxygen production.

Figure 4:
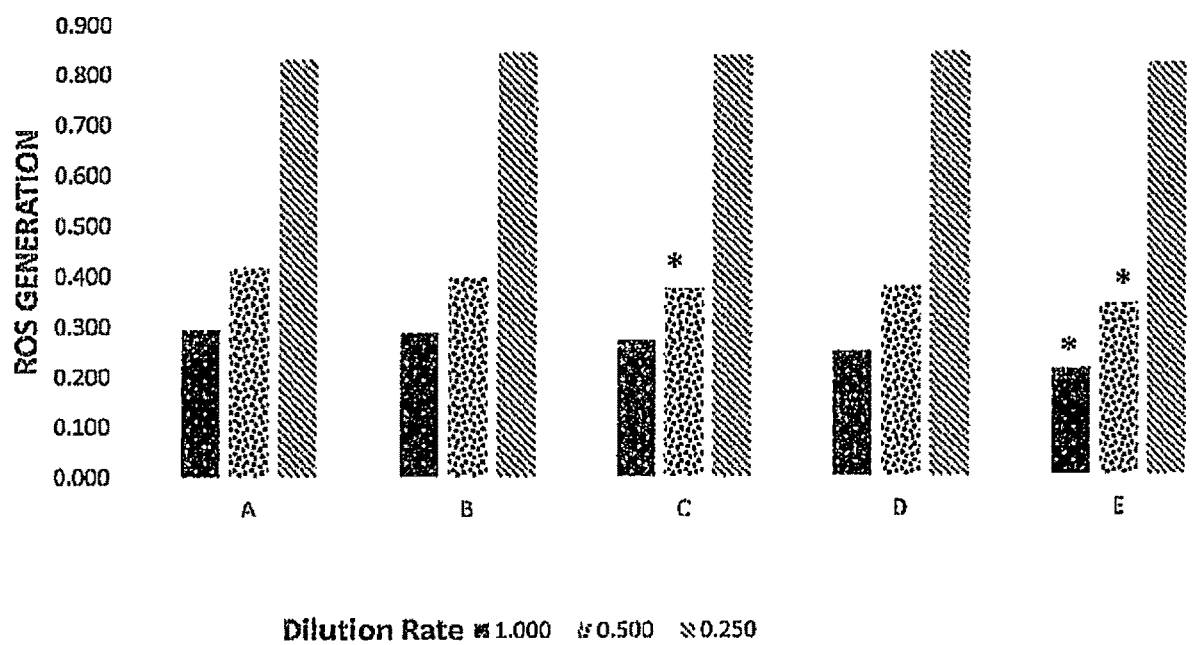
FIG. 4 is a graph showing the synergistic in vitro inhibitory effect of compositions of the present invention (Formulas B-E), as compared with purified *Bombyx mori* cocoon silk peptide fiber alone (Formula A), on the generation of reactive oxygen species (ROS) following exposure to $H_2O_2$.

In FIG. 4, dilutions are shown in column bars from left to right: 1.00 (undiluted composition), 0.5, 0.25. An "*" indicates statistical significance and synergistic effect when compared with Formula A; $p<0.05$ by Student's t-test. As shown in FIG. 4, the results indicate that compositions A-E inhibited the production of ROS in a concentration-dependent manner, in concordance with Examples 2 and 3. Formulas C and E, compositions of the present invention, showed statistically significant protection from ROS generation when compared to Formula A. This tendency shows that in addition to protecting cells, the compositions can also causatively inhibit the generation of ROS, which can cause additional oxidative injury to brain cells.

Example 5

Evaluation of the Inhibition of Active Oxygen Production within SH-SY5Y Neuroblastoma Cells by Compositions of the Present Invention (Oxidative Environment by $FeSO_4$ Administration)

SH-SY5Y neuroblastoma cells were incubated with 100 μl of 10% FBS/MEM in a $5 \times 10^4$ cells/well 96-well plate and cultured 24 hours, as in Examples 1 and 4. The 10% FBS/MEM was changed to 1%, Composition A, B, C, D, or E administered as shown in Table 2 and then the DCF-DA solution administered in the correct concentration as discussed in Example 4.

After 4 hours, 2.5 uM $FeSO_4$ (a toxicity-inducing substance) was administered. Incubation time was for 2 hours before fluorescence test. Subsequently, fluorescence was measured at 530 nm to assess the level of active oxygen production.

Figure 5:
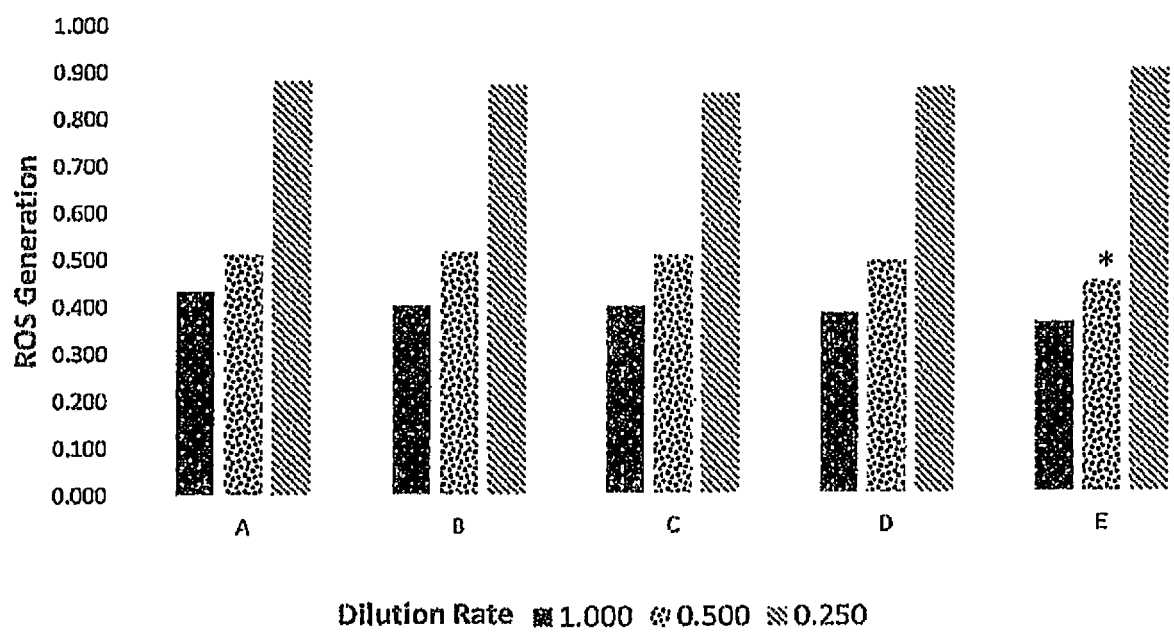
FIG. 5 is a graph showing the synergistic in vitro inhibitory effect of compositions of the present invention (Formulas B-E), as compared with purified *Bombyx mori* cocoon silk peptide fiber alone (Formula A), on the generation of reactive oxygen species (ROS) following exposure to $FeSO_4$.

In FIG. 5, dilutions are shown in column bars from left to right: 1.00 (undiluted composition), 0.5, 0.25. An "*" indicates statistical significance and synergistic effect when compared with Formulation A; $p<0.05$ by Student's t-test. As shown in FIG. 5, the results indicate that formulas A-E inhibited the production of ROS in a concentration-dependent manner. Formula E, a composition of the present invention, showed significantly significant protection from ROS generation when compared to Formula A. The tendency for a consistent concentration-dependent inhibition of the production of ROS in other oxidatve environments was reconfirmed.

Through Examples 1-5 mentioned above, both an antioxidant function and an active oxygen inhibition within the brain cells is shown for all compositions tested, with statistically significant enhancement of results over Formula A for all tested compositions B-E of the present invention: Formula B, Examples 2 and 3; Formula C, Examples 3 and 4; Formula D, Example 2; and Formula E, Examples 2, 3, 4, and 5.

Example 6 and Example 7

Induced Cell Death Challenge

Compositions A-H include combinations of purified *Bombyx mori* cocoon silk peptide fiber) (PEPTYLIN®, refined *Buglossoides arvensis* Seed Oil (NeurXcer), African ginger extract (*Aframomum melegueta* standardized to paradol), and Blueberry standardized extract, as set out in Table 3 below:

TABLE 3

| | Compositions | | | | |
|---|---|---|---|---|---|
| ug | PEPTYLIN | NeurXcel ® | Paradol | Blueberry | NAC* |
| A | 20 | 0 | 0 | 0 | 0 |
| B | 0 | 50 | 0 | 0 | 0 |
| C | 20 | 50 | 2.5 | 0 | 0 |
| D | 20 | 50 | 5 | 0 | 0 |
| E | 20 | 50 | 0 | 2.5 | 0 |
| F | 20 | 50 | 0 | 5 | 0 |
| G | 0 | 0 | 5 | 0 | 0 |
| H | 0 | 0 | 0 | 5 | 0 |
| NAC | 0 | 0 | 0 | 0 | 20 |

*NAC: N-Acetyl-L-cysteine

Compositions A and B include either purified *Bombyx mori* cocoon silk peptide fiber or NeurXcel® Seed Oil, respectively, but not both; while Compositions G and H include neither. Compositions C-F, including both fibroin and NeurXcel® Seed Oil, are compositions according to the present invention.

Figure 6:
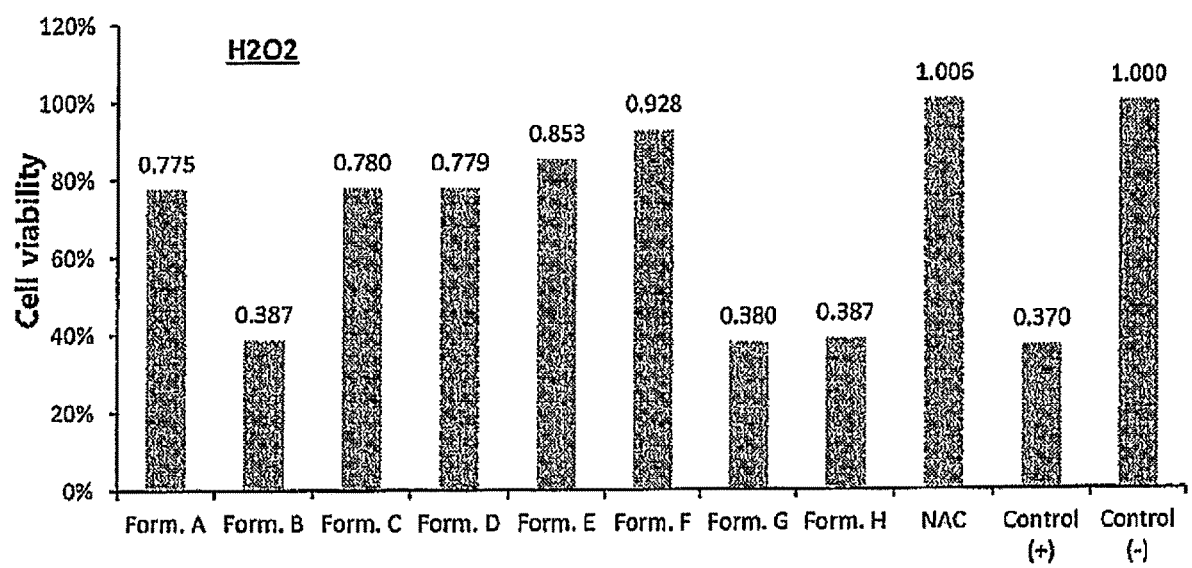
FIG. 6 is a graph showing in vitro results of $H_2O_2$-induced cell death inhibition by compositions of the present invention and various controls.

SH-SY5Y cells were cultured as in Example 2. As shown in FIG. 6, after challenge with $H_2O_2$, Formula A (Peptylin® alone, +77.5%) showed a recovery of +40.5% vs. no treatment (+37%). Accordingly Formula A inhibited induced cell death by +40.5%.

Formula F (+92.8%) performed the best of formulas of the present invention. Formula F showed a recovery of +55.8% vs. no treatment. Formula F synergistically inhibited induced cell death +15.3% better than Formula A (=92.8%–77.5%). This represents a 19.7% relative improvement vs. Peptylin® alone (=92.8%/77.5%). Positive and Negative Controls validate the model, with 37% cell viability remaining after exposure to $H_2O_2$ alone, and 100% cell viability after no exposure to $H_2O_2$. The notation (*) means statistically significant and synergistic increase in cell viability as compared with Formula A. The statistical analysis was performed by Student's t-tests. Each individual in vitro assay was replicated 3 times to assure robustness of the data.

Figure 7:
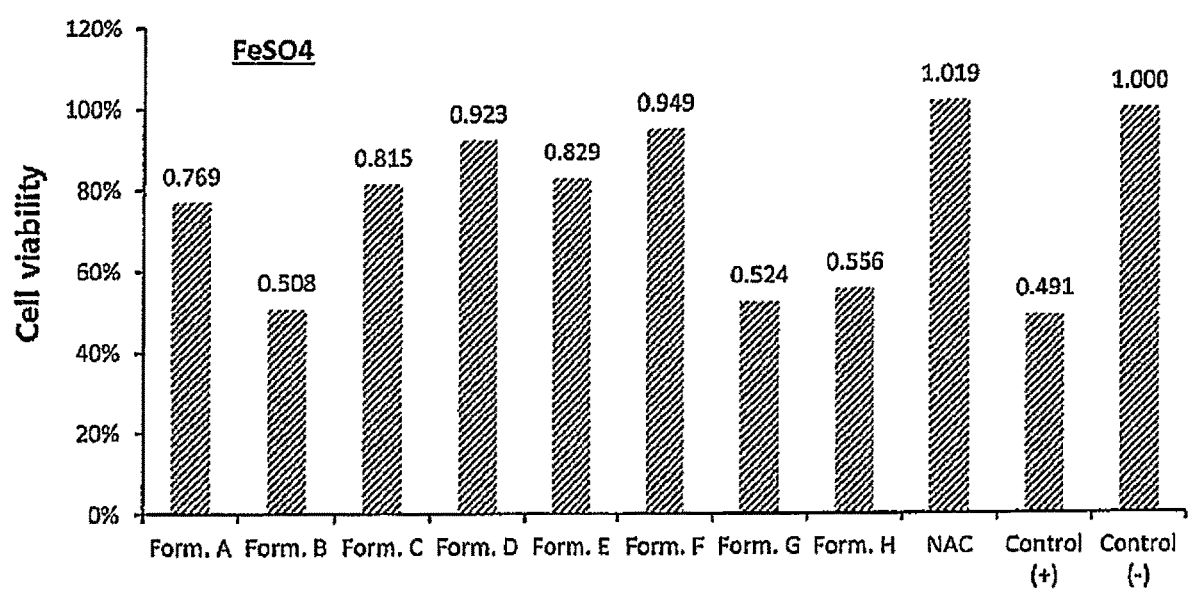
FIG. 7 is a graph showing in vitro results of $FeSO_4$-induced cell death inhibition by compositions of the present invention and various controls.

As shown in FIG. 7, after challenge with $FeSO_4$, Formula A (Peptylin alone, +76.9%) showed a recovery of +27.8% vs. no treatment (+49.1%). Similar to the first experiment, Formula F {+94.9%) performed the highest of the formulations. Specifically, formula F showed a recovery of +45.8% vs. no treatment. Therefore formula F inhibited induced cell death +18.0% better than Formula A(=94.9%–76.9%). This represents a +23.4% relative improvement vs. Peptylin® alone(=94.9%/76.9%). The same controls and replications were followed.

In both induced cell death challenge experiments, the best-performing formulation significantly out-performed Peptylin® alone. The formulation achieved a 45-55% total recovery of neural cells vs. no treatment, an outright cell recovery of up to 95%, and it achieved a 20-23% improvement in cell recovery vs. Peptylin® alone.

Example 8 and Example 9

Reactive Oxygen Species Challenge

In Examples 8 and 9, SH-SY5Y cells were exposed in separate, parallel models to $H_2O_2$ and $FeSO_4$ to induce controlled cell death, but instead of analyzing cell viability in the presence of various active compounds, reactive oxygen species (ROS) generation was measured in the presence of various formulations, following peer-reviewed published methods. ROS is known physiologically as a causative factor in the formation of beta amyloid plaques and damage to key neurotransmitter compounds such as acetylcholine (ACh), and thus is implicated in progressive loss of cognitive function for instance leading to dementia and Alzheimer's disease.

Figure 8:
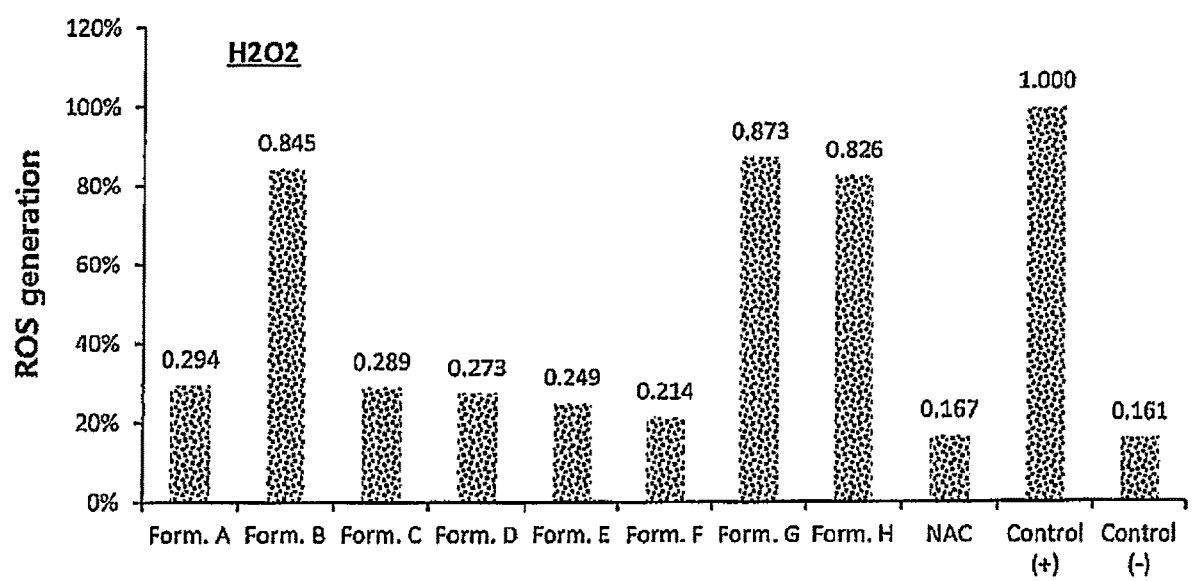
FIG. 8 is a graph showing in vitro inhibition of $H_2O_2$-induced Reactive Oxygen Species (ROS) generation by compositions of the present invention and various controls.
Figure 9:
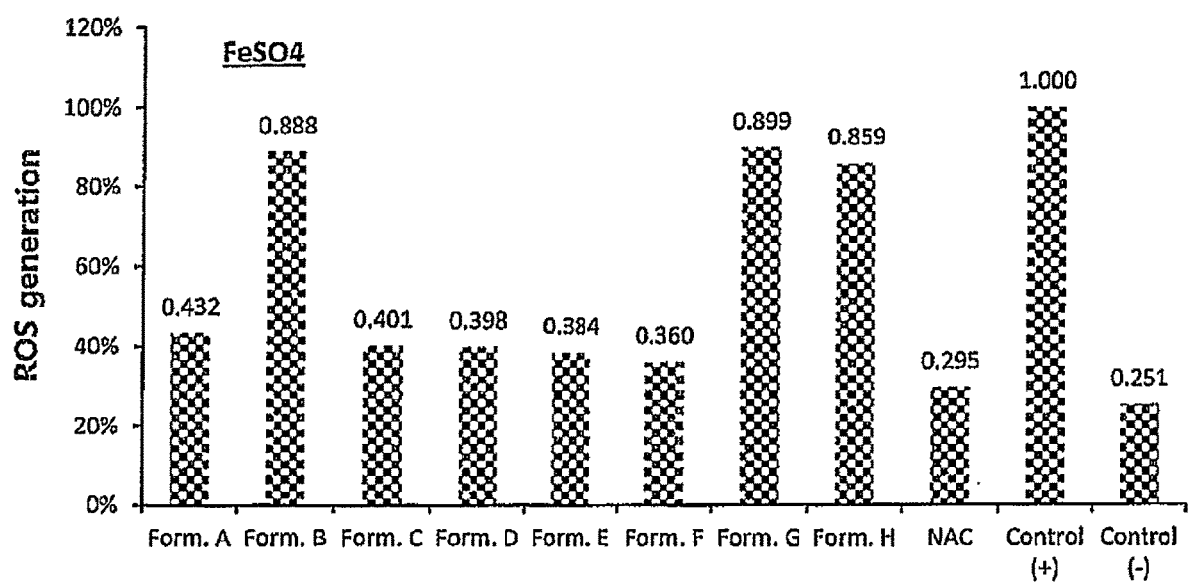
FIG. 9 is a graph showing in vitro inhibition of $FeSO_4$-induced Reactive Oxygen Species (ROS) generation by compositions of the present invention and various controls.

In FIGS. 8 and 9, greater inhibition of ROS is indicated by lower bars, indicating lower ROS generation. Formulations are shown in Table 3.

The results of Example 8 are shown in FIG. 8. FIG. 8 shows formula F achieved the lowest 21.4% ROS generation, compared to formula A (Peptylin®) alone) which achieved 29.4% ROS generation. Therefore formula F out-performed formula A by +8% (=29.4%–21.4%). This represents a +27.2% better, synergistic performance relative to Peptylin® alone (=8%/29.4%). Compared to the positive control (+100% ROS generation), Peptylin® alone showed a +70.6% (=100%–29.4%) ROS inhibition effect and formula F showed a+78.6% ROS inhibition effect(=100%–21.4%).

Similarly, the results of Example 9 (FIG. 9) show that after $FeSO_4$ challenge, formula F achieved the lowest 36% ROS generation, compared to formula A (Peptylin® alone) which achieved 43.2% ROS generation. Therefore formula F out-performed formula A by +7.2% (=43.2%–36%) (*). This represents a +16.7% better, synergistic performance relative to Peptylin® alone (=7.2%/43.2%). Compared to the positive control (+100% ROS generation), Peptylin® showed a +56.8% (=100%–43.2%) ROS inhibition effect and formula F showed a +64% ROS inhibition effect (=100%–36%).

Examples 10-12

Figure 10:
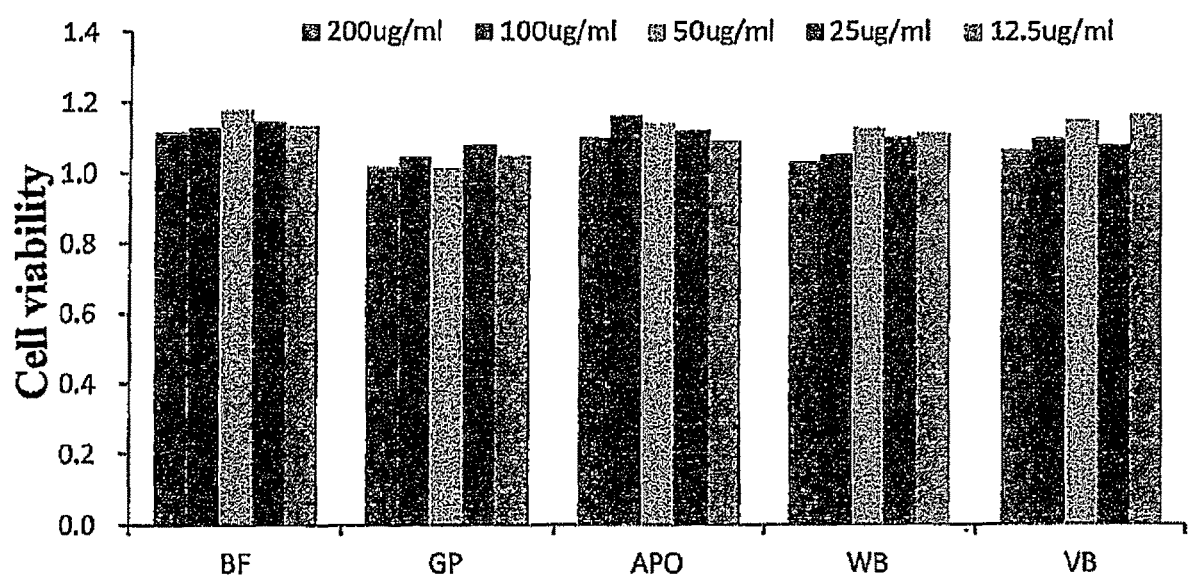
FIG. 10 is a graph showing in vitro cell viability tests of various compositions.

Examples 10-12 disclose similar results achieved with two different Blueberry Extracts of the present invention. The Wild Blueberry (*Vaccinium angustifolium*) powder tested and disclosed for instance at FIG. 10 is wild Canadian Blueberry extract (Blue d'Or) from Fruit d'Or (labeled as "WB"), discussed above. The American Blueberry (*Vaccinium corymbosum*) extract) (VitaBlue® is a powder from Futureceuticals (labeled as "VB"), discussed above.

Example 10

Cell Viability Tests

SH-SY5Y cells were plated on 96-well plates at a density of $5 \times 10^4$ cells/well in 100 ul of 10% FBS/MEM and incubated for 24 hours. The media was replaced with 90 ul of 1% FBS/MEM, and then the compositions shown in the table were added to the cells. After the treatment, bug of MTT (3-(4,5-dimethylthiazol-2-yl)-2,5-diphenyltetrazolium bromide) (Invitrogen/ThermoFisher, Carlsbad Calif., USA) was aseptically added. The cells were incubated for about 2-4 hours and the absorbance of the cells was measured at a wavelength of 570 nm using an ELISA reader. Amounts of sample treatments were 10 ul per well.

Figure 11:
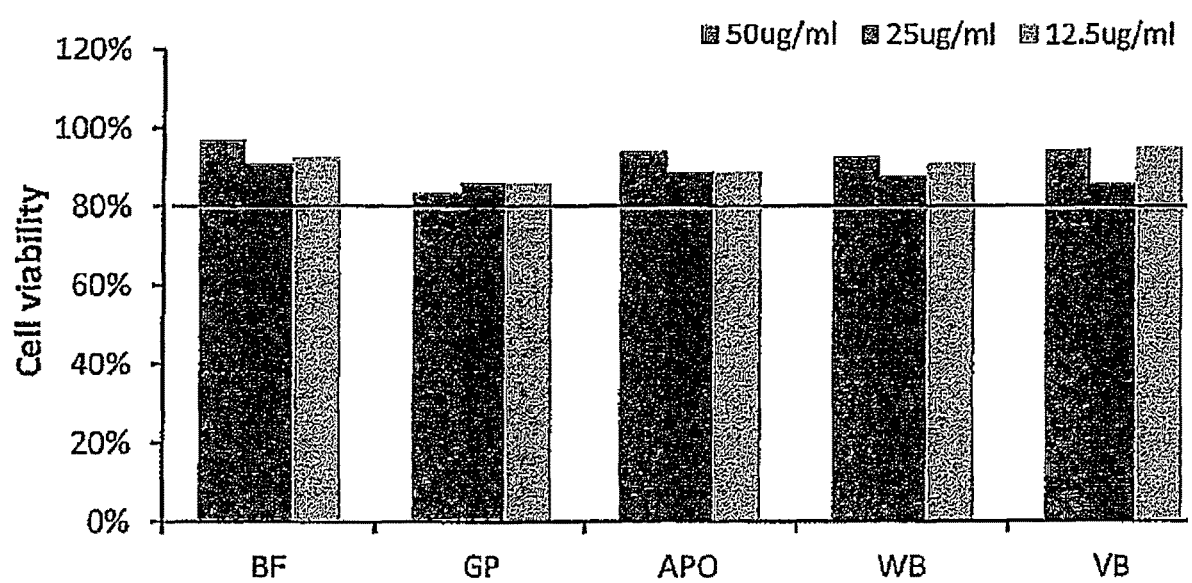
FIG. 11 is a graph showing in vitro cell viability tests of various compositions.

Results are displayed in FIGS. 10 and 11 and Tables 4 (FIG. 10) and 5 (FIG. 11), with dilutions ranging from 200-12.5 ug as applied shown from left to right in column bars for each substance tested. In FIGS. 10 and 11, PP refers to Peptylin® powder, GP to Grains of Paradise (15% 6-paradol powder), AFO to NeurXcel® oil, and WB to Wild blueberry powder, VB to American blueberry powder (VitaBlue®).

FIGS. 10 and 11 show no cytotoxicity was present in any of the dilution ratios (1–0.0625) for any of the substances tested.

TABLE 4

| Conc. (ug/mL) | BF | GP | AFO | WB | VB | Control |
|---|---|---|---|---|---|---|
| 200 | 1.115 | 1.019 | 1.103 | 1.033 | 1.065 | 1.280 |
| 100 | 1.126 | 1.048 | 1.163 | 1.053 | 1.099 | 1.223 |
| 50 | 1.178 | 1.014 | 1.143 | 1.129 | 1.152 | 1.215 |
| 25 | 1.146 | 1.081 | 1.122 | 1.105 | 1.083 | 1.257 |
| 12.5 | 1.135 | 1.048 | 1.092 | 1.114 | 1.166 | 1.224 |

TABLE 5

| Conc. (ug/mL) | BF | GB | AF | WB | VB | F(Control) |
|---|---|---|---|---|---|---|
| 50 ug/ml | 97% | 83% | 94% | 93% | 95% | 100% |
| 25 ug/ml | 91% | 86% | 89% | 88% | 86% | 100% |
| 12.5 ug/ml | 93% | 86% | 89% | 91% | 95% | 100% |

Example 11

Compositions Providing Protection from $H_2O_2$-Induced Cell Death

SH-SY5Y cells were plated on 96-well plates at a density of $5 \times 10^4$ cells/well in 100 ul of 10% FBS/MEM and incubated for 24 hours. The media was replaced with 90 ul of 1% FBS/MEM. Formulations shown in the table below were incubated with the cells for 4 hours (in triplicate, 3 dilutions). $H_2O_2$ was added to the cells and incubated with the cells for 24 hours. After the treatment, bug of MTT (3-(4, 5-dimethylthiazol-2-yl)-2,5-diphenyltetrazolium bromide) (Invitrogen/ThermoFisher, Carlsbad Calif., USA) was aseptically added. The cells were incubated for 3 to 4 hours and the absorbance of the cells measured at 570 nm wavelength using an ELISA reader.

TABLE 6

| ug | PEPTYLIN® | NeurXcel® | Paradol | WB | VB | $H_2O_2$ |
|---|---|---|---|---|---|---|
| Formula A | 20 | 0 | 0 | 0 | 0 | + |
| Formula B | 20 | 50 | 2.5 | 5 | 0 | + |
| Formula C | 20 | 50 | 2.5 | 0 | 5 | + |
| Control (+) | | | | | | + |
| Control (−) | | | | | | − |

Figure 12:
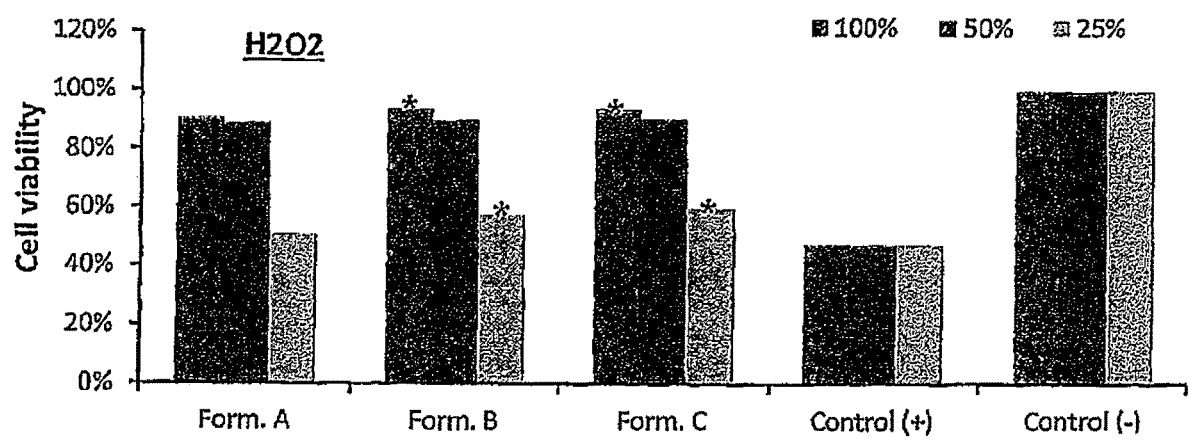
FIG. 12 is a graph showing synergistic in vitro neuroprotective effects by compositions of the present invention after $H_2O_2$ challenge.

FIG. 12 shows a statistically significant increase in cell viability for the 100% and 25% dilutions of Formulas B and C as compared with Formula A, showing the synergistic effect achieved with compositions of the present invention with both blueberry extracts tested. Results as shown in FIG. 12 show dilutions 100%, 50%, 25% from left to right for each Formula. Cell viability tended to decrease as the concentration decreased. In the comparison between formula A, B, and C, the notation (*) means statistically significant, synergistic increase in cell viability as compared with Formula A. Statistical analysis was performed by Student's t-tests.

TABLE 7

| | Formula A | Formula B | Formula C | Control (+) | Control (−) |
|---|---|---|---|---|---|
| 100% | 91% | 94% | 94% | 47% | 100% |
| 50% | 89% | 90% | 90% | 47% | 100% |
| 25% | 51% | 58% | 60% | 47% | 100% |
| Control (+) | 47% | 47% | 47% | | |
| Control (−) | 100% | 100% | 100% | | |

Example 12

Compositions Inhibiting $H_2O_2$-Induced Reactive Oxygen Species Generation

Reactive oxygen species generation induced by $H_2O_2$ was measured by incubation with a fluorescent probe 2',7'-dichlorofluorescin diacetate (DCF-DA). SH-SY5Y cells were stained with LOAM of DCF-DA. The cells were collected, and washed with PBS. Cells stained with DCF-DA were incubated then measured with excitation at 485 nm and emission at 530 nm by fluorometer.

Formulations used in this experiment were as follows:

TABLE 8

| ug | PEPTYLIN® | NeurXcel® | Paradol | WB | VB | $H_2O_2$ |
|---|---|---|---|---|---|---|
| Formula A | 20 | 0 | 0 | 0 | 0 | + |
| Formula B | 20 | 50 | 2.5 | 5 | 0 | + |
| Formula C | 20 | 50 | 2.5 | 0 | 5 | + |
| Control (+) | | | | | | + |
| Control (−) | | | | | | − |

The positive control group, NAC, confirmed that SH-SY5Y cells were restored to normal levels.

Figure 13:
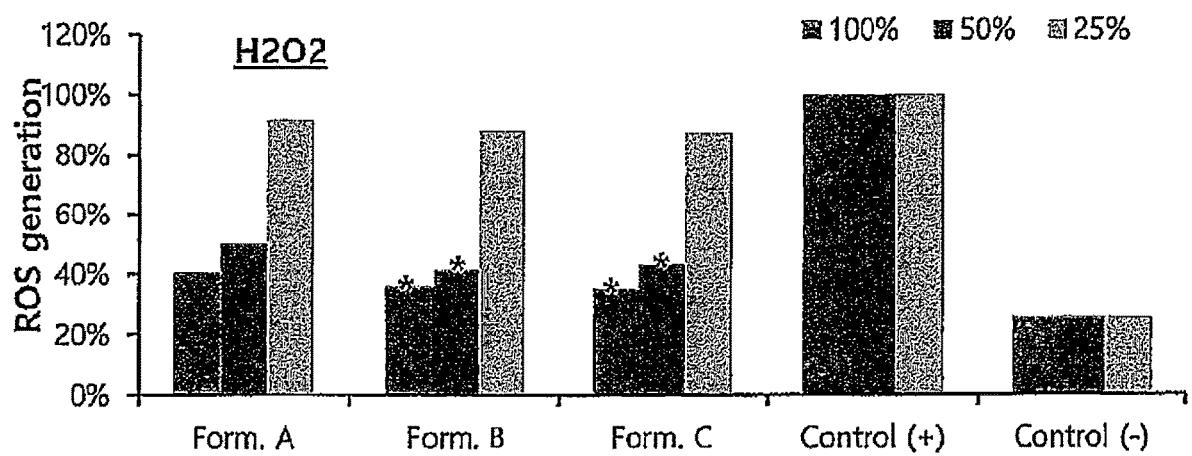
FIG. 13 is a graph showing synergistic in vitro inhibition of Reactive Oxygen Species generation by compositions of the present invention after $H_2O_2$ challenge.

FIG. 13 shows a statistically significant inhibition of ROS generation for the 100% and 50% dilutions of Formulas B and C as compared with Formula A, showing the synergistic effect achieved with both blueberry extracts tested. The results show that the higher the concentration, the more the ROS generation was suppressed. Results as shown in FIG. 13 show dilutions 100%, 50%, 25% in column bars from left to right for each Formula. In the comparison between formula A, B, and C, the notation (*) means statistically significant increase in cell viability as compared with Formula A. Statistical analysis was performed by Student's t-tests.

In Vivo Tests

Examples 13-21

Individual subjects participated in voluntary open label empirical evidence trials using a synergistic composition of the subject invention, Braini®. As discussed above, Braini® is a combination of Peptylin® powder (400 mg/day); NeurXcel® microencapsulated powder (500 mg powder/day); and Blueberry extract powder (*Vaccinium corymbosum*) (100 mg/day). 500 mg NeurXcel® microencapsulated powder includes 250 mg NeurXcel® oil and 250 mg of microencapsulated powder composed primarily of modified food starch, corn syrup solids, antioxidants, and natural flavors. Braini® capsules in the above amounts were administered daily to human subjects of the below Examples. Administration to human subjects was for 28 days, unless indicated otherwise.

In the below Examples, subjects were tested before administration of Braini® capsules, and then after administration of Braini® capsules. The following tests were conducted according to CNS Vital Signs (Morrisville, N.C.) testing protocols, which are reproduced or paraphrased in part as follows: Subject scores were used to assess their Verbal Memory, Psychomotor Speed, Reaction Time, Cognitive Flexibility, Processing Speed, Executive Function, and/or Motor Speed, as described in the Examples below. Scores help identify cognitive deficits and if present, level of impairment, using an age-matched normative comparison database. Standard scores (ss) for subjects of similar age, and percentile ranks (Pr), are auto-scored using an algorithm based on a normative data set of 1600+ subjects, ranging from ages 8-90. In the age-matched normative sample, subjects were (1) in good health, (2) had no past or present psychiatric or neurological disorders, head injury, or learning disabilities, and (3) the sample subjects were free of any centrally-acting medications. CNS Vital Signs cognitive tests are used by thousands of researchers and physicians in over 50 countries, and for instance in the United States by the US military and the Veterans Administration.

The CNS Vital Signs normative data is presented in ten (10) age groups: less than 10 years old, 10-14 years old, 15-19 years old, 20-29 years old, 30-39 years old, 40-49 years old, 50-59 years old, 60-69 years old, 70-79 years old, 80 years and older. Standard scores (ss) above 109 (>74 percentile) are considered as Above Average, High Function and High Capacity; ss of 90-109 (25-74 percentile) are considered as Average, Normal Function and Normal Capacity; ss of 80-89 (9-24 percentile) are considered as Low Average, Slight Deficit and Slight Impairment; ss of 70-79 (2-8 percentile) are considered as Low, Moderate Deficit and Impairment Possible; ss of less than 70 (less than 2 percentile) are considered as Very Low, Deficit and Impairment Likely. For CNS Vital Signs results, the color Red (R) indicates a "Very Low" score as compared with age-normed population cohort; Orange (O)="Low", Yellow (Y)="Low Average", Light Green (LG)="Average", Dark Green (DG)="Above Average". Reaction times are in milliseconds. Generally, higher scores indicate better performance, with the exception of Reaction Time, where a lower score ("*") indicates better functioning. Patient Scores are raw scores calculations generated from data values of individual subtests. Percentile ranks are a mathematical transformation of the standard score and an index of how the subject scored compared with other subjects of the same age on a scale of 1 to 99. Normal aging affects performance on all CNS Vital Signs tests. A subject's standard scores are based on data from normal controls that are the same age. Education and special skills may affect test performance, therefore concern should be taken for subjects that are very intelligent or well educated yet their scores are below average. With any neuropsychological tests, results can be affected by motivation or effort level; the Validity Indicator will help identify those patients. Further information is available on the CNS Vital Signs website, www.cnsvs.com; see for instance the Brief Interpretation Guide.

The below tests are discussed in Examples below:

Verbal Memory (VBM) measures recognition memory for words and geometric figures. Fifteen words are presented, one by one, on the screen every two seconds. For immediate recognition (learning phase), the participant must identify those words nested among fifteen new words. Then, after six more tests, there is a delayed recognition memory trial. Subjects respond by using the space bar on a keypad. VBM is calculated as follows: VBM Correct Hits Immediate+VBM Correct Passes Immediate+VBM Correct Hits Delay+VBM Correct Passes Delay. VBM tests include Learning Words, Memory for Words, Word Recognition, Immediate and Delayed Recall. Real-life examples of Verbal Memory include remembering a scheduled test, recalling an appointment, taking medications, and attending class. VBM is considered a single test domain.

Psychomotor Speed measures how well a subject perceives, attends, responds to visual-perceptual information, and performs motor speed and fine motor coordination. Psychomotor Speed is considered a multiple test domain (combines tests for Motor Speed and Processing Speed). A Finger Tapping Test and a Symbol Digit Coding Test may be used to measure and calculate Psychomotor Speed. Psychomotor Speed is calculated as follows: Finger Tapping Test Right Taps Average+Finger Tapping Test Left Taps Average+Symbol Digit Coding Correct Responses. A Finger Tapping Test has subjects press the space bar on a keypad with their right index finger as many times as they can in 10 seconds. They do this once for practice, and then there are three test trials. The test is repeated with the left hand. A Finger Tapping Test includes motor speed and fine motor control. A Symbol Digit Coding test consists of serial presentations of screens, each of which contains a bank of eight symbols above and eight empty boxes below. The participant types in the number on the number row that corresponds to the symbol that is highlighted. Only the digits from 2 through 9 are used; this is to avoid confusion between "1" and "l" on the keypad. The computer program does not allow a person to use a numerical pad preventing a distinct advantage for those who are skilled at using the numerical pad or for those that are right- versus left-handed. A Symbol Digit Coding test relates to complex information processing accuracy, complex attention, visual-perceptual speed, and information processing speed. Real-life examples relating to Psychomotor Speed include ability to perform simple motor skills and dexterity through cognitive functions such as used of precision instruments or tools, performing mental and physical coordination such as driving a car, playing a musical instrument.

Reaction Time measures how quickly a subject can react, in milliseconds, to a simple and increasingly complex direction set. Reaction time is considered a single test domain. Stroop Test Complex Reaction Time and Stroop Reaction Time may be used to measure and calculate Reaction Time. When considering Reaction Time results, a lower score indicates better functioning (in contrast to other tests described in this application). A Stroop Test has three parts. In the first part, the words RED, YELLOW, BLUE, and GREEN (printed in black) appear at random on the screen, and the participant presses the space bar as soon as the test subject sees the word. In the second part, the words RED, YELLOW, BLUE, and GREEN appear on the screen, printed in color. The participant is asked to press the space bar when the color of the word matches what the word says. In the third part, the words RED, YELLOW, BLUE, and GREEN appear on the screen, printed in color. The participant is asked to press the space bar when the color of the word does not match what the word says. A Stroop Test relates to simple reaction time, complex reaction time, Stroop reaction time, inhibition/disinhibition, and frontal or executive skills. Real-life examples relating to Reaction Time include driving a car, attending to conversation, tracking and responding to a set of simple instructions, taking longer to decide what response to make.

Cognitive Flexibility measures how well a subject is able to adapt to a rapidly changing and increasingly complex set of directions and/or to manipulate the information. Cognitive Flexibility is considered a multiple test domain (Executive Function and Stroop Test) and is calculated as follows: Shifting Attention Test Correct Responses—Shifting Attention Test Errors—Stroop Commission Errors. The Shifting Attention Test is measure of ability to shift from one instruction set to another quickly and accurately. Participants are instructed to match geometric objects either by shape or by color. Three figures appear on the screen, one on top and two on the bottom. The top figure is either a square or a circle. The bottom figures are a square and a circle. The figures are either red or blue (mixed randomly). The participant is asked to match one of the bottom figures to the top figure. The rules change at random (i.e. match the figures by shape, for another, by color) and subject responds by pressing the two shift keys. The Shifting Attention Test relates to executive function, shifting sets: rules, categories, and rapid decision making; and reaction time. Real-life examples relating to Cognitive Flexibility include reasoning, switching tasks, decision-making, impulse control, strategy formation, and attending to conversation.

Processing Speed measures how well a subject recognizes and processes information, that is, perceiving, attending/responding to incoming information, motor speed, fine motor coordination, and visual-perceptual ability. Processing Speed is considered a single test domain. Processing Speed is calculated as follows: Symbol Digit Coding Correct Responses—Symbol Digit Coding Errors. Real-life examples relating to Processing Speed include ability to recognize and respond/react, that is, fitness-to-drive, occupation issues, possible danger/risk signs or issues with accuracy and detail.

Executive Function measures how well a subject recognizes rules, categories, and manages or navigates rapid decision making. Executive Function is considered a single test domain. Executive Function is calculated as follows: Shifting Attention Test Correct Responses—Shifting Attention Test Errors. Real-life examples relating to Executive Function may include the ability to sequence tasks and manage multiple tasks simultaneously as well as tracking and responding to a set of instructions. Executive Function is one of the most difficult neuro-cognitive performance measures to influence, especially without stimulants. Yet for instance in the context of the SAT-RT test (Shifting Attention Test—Reaction Time), healthy senior adult subjects experienced an improvement in this parameter using Braini® capsules for 28 days, as compared with placebo, with an indicative p-value=0.05.

Motor Speed measures a subject's ability to perform movements to produce and satisfy an intention towards a manual action and goal. Motor Speed is considered a single test domain. Motor Speed is calculated as follows: Finger Tapping Test Right Taps Average+Finger Tapping Test Left Taps Average. Real-life examples relating to Motor Speed include the preparation and production of simple manual dexterity actions, such as manipulating and maneuvering objects.

Example 13

Individual healthy seniors participated in a voluntary open label empirical evidence trial using the Braini® composition identified above. Before administration of this composition, individual (human) subjects first took an online battery of standardized memory, cognitive performance, and neuro-physiological tests produced by CNS Vital Signs (Morrisville, N.C.). After 30 days of daily intake of the composition, the subjects took a follow-up standardized CNS Vital Signs test suite. Individual and consolidated results for each subject are shown in FIG. 14. Significant, synergistic improvements in 5 of 7 CNS Vital Signs memory, cognitive performance, and neuro-physiological scores occurred over a cohort of 8 healthy seniors with an average age of 70 years (range: 68-73 years). Average cohort performance improved significantly from +9.4% to +20.8% across the 5 assessment parameters: Verbal Memory; Processing Speed; Reaction Time; Psychomotor Speed; and Motor Speed. For the other two assessment parameters, only modest average cohort improvements occurred. Cognitive Flexibility improved by +0.9% and Executive Function improved by +2.8%.

Example 14

Subjects diagnosed with neurodegenerative diseases such as Parkinson's disease and Multiple Sclerosis consumed a formulated embodiment of the subject invention (Braini® capsules, as described above) for periods of up to 6 months under a physician's observational trial model coupled to the standardized CNS Vital Signs (Morrisville, N.C.) cognitive performance assessment tool given at baseline prior to taking the active composition and monthly thereafter. Such subjects achieved superior and significant, synergistic cognitive performance improvements over baseline within 30-60 days of continuous consumption of the referenced composition. Such subjects then discontinued consuming the formulation after an initial active product consumption phase of up to 4 months. Contrary to expectation, the subjects' cognitive performance sustained at the significantly higher levels over baseline for 30-60 days without significant changes to their dietary or lifestyle regimens, other than the removal of the active formulation, showing a synergistic, structural neuro-physiological effect beyond what is expected from available neuro-protective prescription drugs. After up to 60 days' non-consumption of the embodiment, the subjects' cognitive performance declined significantly, evidencing that their neuro-physiological status was starting to return to baseline conditions. Once the subjects resumed consuming the active formulation, in 30-60 days of resumed active supplementation, their cognitive performance once again improved significantly in at least 4 of 7 cognitive batteries (Verbal Memory, Psychomotor Speed, Reaction Time, Cognitive Flexibility, Processing Speed, Executive Function, Motor Speed) under the CNS Vital Signs (Morrisville, N.C.) assessment tool. See for example MS Subject's performance improvement in FIG. 15. The color Red (R) indicates a "Very Low" score as compared with age-normed population cohort; Orange (O)="Low", Yellow (Y)="Low Average", Light Green (LG)="Average", Dark Green (DG)="Above Average". The above references to color in CNS Vital Signs data apply to other Examples and data as well.

In addition to the above, evidence of remyelination and sustained Executive Function and Cognitive Flexibility in a subject with Multiple Sclerosis was seen with Braini® administration. A senior adult (age 60) began oral administration of a composition of this invention, Braini® capsules as described above, about 187 days after the first entry in the below Table "Days between Tests 0". Administration continued for about 4 months, and then ceased for about 6 weeks (beginning just before "Days Between Tests" below, period of 41 days)". At the end of the 6 weeks, the subject was again administered the Braini® capsules, continuing to take Braini® capsules for about 6 weeks through the end of testing indicated in the below table, and with continuous administration of Braini® capsules through the date of filing this application (about 14 months). No adverse effects were reported by the subject.

Table 9 row 1 shows that before administration of Braini® capsules, the subject tested in the Very Low Category for Psychomotor Speed, Cognitive Flexibility, Processing Speed, and Executive Function. After four months of daily Braini® administration, as shown by the row marked as having 31 days between tests, the subject had steadily improved in each of these areas. Upon resumption of Braini® administration, about 7 months after the initial administration, Cognitive Flexibility, Executive Function, and Processing Speed were dramatically improved in the subject, from Very Low to Average placement. Psychomotor Speed had also dramatically improved to indicate a high functioning test subject, still in the Low Average category. Other improvements may also be seen in the below Table.

In addition, the spouse of the subject with Multiple Sclerosis, having known the subject for 35 years, reported substantial improvements in the subject's abilities with Braini® administration. The spouse commented on the subject's gradual deterioration in verbal memory with the disease, and that the subject's reaction time with Braini® administration is significantly improved, and post-Braini® speech is not as labored as pre-Braini® speech.

Also, before Braini® administration, the spouse reported the subject experienced a noticeable decline in motor function, speech, and reaction time. The spouse reported the subject had always been a "list maker" but that, as the disease progressed, the subject had stopped planning and making lists. However, Braini® administration restored some of that function to the subject. The spouse further continued that after only a week to 10 days of Braini® administration, the subject with multiple sclerosis began to improve noticeably. Also, the spouse commented that the subjects local neurologist had noted improvements in the subject's motor speed, in keeping with that observed with data reported herein from CNS Vital Signs testing. Also, the spouse commented that the subject's specialist neurologist (Mass General Hospital, Boston, Mass.) noted re-myelination in the subject's most recent MRI images.

TABLE 9

Administration of Braini ® capsules to an adult senior with Multiple Sclerosis, 0-7 months

| Days between Tests | Verbal Memory Std Scores | Psychomotor Speed Std Scores | Reaction Time Std Scores | Cognitive Flexibility Std Scores | Processing Speed Std Scores | Executive Function Std Scores | Motor Speed Std Scores |
|---|---|---|---|---|---|---|---|
| 0 | 109 | 59 | 85 | 31 | 59 | 33 | 73 |
| 216 | 77 | 61 | 92 | 44 | 75 | 44 | 67 |
| 17 | 96 | 69 | 97 | 86 | 81 | 87 | 73 |
| 17 | 106 | 75 | 104 | 86 | 83 | 88 | 79 |
| 15 | 99 | 76 | 96 | 78 | 94 | 80 | 74 |
| 31 | 115 | 74 | 119 | 89 | 87 | 88 | 74 |
| 41 | 115 | 75 | 99 | 71 | 83 | 72 | 79 |
| 14 | 112 | 71 | 106 | 79 | 85 | 81 | 73 |
| 31 | 112 | 84 | 92 | 75 | 92 | 78 | 86 |
| 29 | 115 | 81 | 100 | 99 | 94 | 100 | 80 |

Tables 10 and 11 show CNS Vital Signs testing results for the senior adult with Multiple Sclerosis about 18 months after beginning Braini® administration, with administration halted for about 6 weeks as mentioned above. The subject scored Average in Reaction Time, Cognitive Flexibility, Processing Speed, and Executive Function, and Low Average in Psychomotor Speed and Motor Speed. No Very Low or Low Average scores were assessed during this test, showing no impairment or deficit in the subject. These results show that chronic administration of Braini® capsules provided a continued benefit to the subject, transforming the subject's profile from impairments in several categories into a subject with no apparent impairments or deficits. As of the date of the filing of this application, the subject continues to take Braini® capsules with no adverse effects and with continued improvement or maintenance scores as compared with pre-Braini® scores (21 months' since beginning Braini® capsule administration). The data are consistent with providing neuroprotection and remyelination in the subject. In addition to the above data, the subject is described as dramatically improved in speech, demeanor, and cognitive function after long-term administration of Braini® capsules.

TABLE 10

Improvement 21 Months After Beginning Administration of Braini ® Capsules to an Adult Senior Subject With Multiple Sclerosis

| Patient Profile | | Percentile Range<br>Standard Score Range | | >74<br>>109 | 25-74<br>90-109 | 9-24<br>80-89 | 2-8<br>70-79 | <2<br><70 |
|---|---|---|---|---|---|---|---|---|
| Domain Scores | Patient Score | Standard Score | Percentile | Valid Score** | Above | Average | Low Average | Low | Very Low |
| Psychomotor Speed | 127 | 84 | 14 | Yes | | | X | | |
| Reaction Time* | 695 | 101 | 53 | Yes | | X | | | |
| Cognitive Flexibility | 35 | 99 | 47 | Yes | | X | | | |
| Processing Speed | 40 | 95 | 37 | Yes | | X | | | |
| Executive Function | 38 | 100 | 50 | Yes | | X | | | |
| Motor Speed | 87 | 81 | 10 | Yes | | | X | | |

TABLE 11A

Finger Tapping Test (FTT)

| Tested Information | Score | Standard | Percentile |
|---|---|---|---|
| Right Taps Average | 48 | 89 | 23 |
| Left Taps Average | 39 | 76 | 5 |

The FTT is a test of motor speed and fine motor control ability. There are three rounds of tapping with each hand. The FTT test measures the speed and the number of finger-taps with each hand. Low scores indicate motor slowing. Speed of manual motor activity varies with handedness. Most people are faster with their preferred hand but not always.

TABLE 11B

Symbol Digit Coding (SDC)

| Tested Information | Score | Standard | Percentile |
|---|---|---|---|
| Correct Responses | 40 | 93 | 32 |
| Errors* | 0 | 114 | 82 |

The SDC test measures speed of processing and draw upon several cognitive processes simultaneously, such as visual scanning, visual perception, visual memory, and motor functions. Errors may be due to impulsive responding, misperception, or confusion.

TABLE 11C

Stroop Test (ST)

| Tested Information | Score | Standard | Percentile |
|---|---|---|---|
| Simple Reaction Time* | 379 | 87 | 19 |
| Complex Reaction Time Correct* | 553 | 110 | 75 |
| Stroop Reaction Time Correct* | 836 | 93 | 32 |
| Stroop Commission Errors* | 3 | 92 | 30 |

The ST measures simple and complex reaction time, in libition/disinhibition, mental flexibility or directed attention. The ST helps assess how well a subject is able to adapt to rapidly changing and increasingly complex set of directions. Prolonged reaction times indicate cognitive slowing/impairment. Errors may be due to impulsive responding, misperception, or confusion.

TABLE 11D

Shifting Attention Test (SAT)

| Tested Information | Score | Standard | Percentile |
|---|---|---|---|
| Correct Responses | 42 | 94 | 34 |
| Errors* | 4 | 109 | 73 |
| Correct Reaction Time* | 1251 | 93 | 32 |

Example 15

Subjects diagnosed with dyslexia consumed a formulated embodiment of the subject invention for at least 30 days under a physician's observational model coupled to the standardized CNS Vital Signs (Morrisville, NC) cognitive assessment tool given at baseline prior to taking the active composition, and again after 30 days of continuous consumption of the active composition. The fact of the subjects' dyslexia is captured readily in their relatively poor performance in the Cognitive Flexibility and Executive Function scores. See FIG. 16A where each subject scored normatively in the 30-39 range ("Very Low") in both assessments. Yet, unexpectedly, given that healthy non-dyslexic subjects in FIG. 16A showed, on average, relatively little improvement in Cognitive Flexibility and Executive Function as a result of consuming the active composition for at least 30 days, the dyslexic subjects showed dramatic improvements in Cognitive Flexibility and Executive Function scores (ranging from +142% to +176%) after 30 days, improving their normative results from "Very Low" to "Average" in their respective population age cohorts. This shows an unexpected, synergistic improvement in functional cognition by dyslexic subjects as compared to non-dyslexic subjects in the general population.

FIG. 16B shows results from a physician's observational trial after Braini® administration for at least 30 days in 6 dyslexic subjects (5 adults, 1 child). Data reported in FIG. 16B includes data from the subjects identified in FIG. 16A plus additional subjects, for a total of 6 dyslexic subjects studied. All subjects studied experienced significant improvement in Cognitive Flexibility and Executive Function outcomes measures using the CNS Vital Signs standardized cognitive performance assessment tool, after taking Braini® as directed for at least 30 days. A consistent pattern of regular Braini® use driving improved Cognitive Flexibility and Executive Function outcomes is novel and unique to dyslexic subjects. As shown in FIG. 16B, after 30 days' administration of Braini®, dyslexic subjects enjoyed from 16% to 187% improvement in Cognitive Flexibility and about 19% to 174% in Executive Function.

Further, all 6 dyslexic subjects experienced notable improvements in their Reaction Time outcome measures. As it was discovered that participants in the university controlled human clinical trials experienced significant improvement in their SAT-RT scores, it is noteworthy that dyslexic subjects' overall Reaction Time scores consistently improved.

Example 16

Individual healthy seniors participated in a voluntary open label empirical evidence trial intended to determine whether any significant changes in cognitive performance occur after a subject consumed Peptylin® for 30 days and then switched to Braini® (a composition of the present invention) for an additional 30 days. Before administration of the first composition (Peptylin®, 400 mg/day), individuals first took an online battery of standardized memory, cognitive performance, and neuro-physiological tests produced by CNS Vital Signs (Morrisville, N.C.), noted as "SS1". After 30 days of daily intake of the Peptylin formulation, the subjects then took a follow-up standardized CNS Vital Signs test suite. Standardized scores were recorded, noted as "SS2". The subjects then switched immediately to Braini® and consumed it as directed for an additional 30 days. The subjects took an additional CNS Vital Signs test suite, with recorded scores noted as "SS3". Individual and average results for each subject are shown in FIG. 17. After consuming Braini® for 30 days, significant, synergistic improvements vs. Peptylin® alone in Cognitive Flexibility and Executive Function (+21%, +23% respectively) occurred. No other significant changes in 5 other cognitive performance and neuro-physiological test scores occurred, the standard of significance being a 7% or greater change in scores. This shows that there is a therapeutic benefit in taking Braini® over and above pure Peptylin®, and that the observed synergistic effect of in vitro compositions of the present invention such as Braini® vs. Peptylin® in Examples 1-12 (above) correlates therapeutically to the significant improvements in Cognitive Flexibility and Executive Function in humans who consume Braini® vs Peptylin®.

Example 17

Physician's Observational Data

FIGS. 18-23 show the results of CNS Vital Signs testing on 43 human subjects before and after administration of Braini®. Braini LLC has conducted open-label physician observed studies comparing healthy subjects' cognitive and neurophysiological performance using the CNS Vital Signs online self-test assay suite. These empirical studies have been carried out comparing a subject's outcome scores on Day 0 (prior to taking Braini®) and again after 30-60 days of taking Braini® as directed, using six of the CNS Vital Signs standardized outcome measures. In some cases, subjects were re-tested more than 60 days after their Day 0 test, because they delayed their initial start taking Braini. This suite of tests is notable for having been used in federally-backed neurological research, including for the US military, by over 10,000 physicians and 40 million test subjects. It is considered a standard for assessing memory and cognitive performance. General statements regarding CNS Vital Signs are applicable to other Examples using the CNS Vital Signs test suite.

Overall, 43 healthy subjects (age 11-80) completed the Braini Physician's Observational Trial. After taking Braini for at least 28 days, an average of 76% of subjects experienced notable average 9-12% improvements in CNS Vital Signs (CNS VS) outcome measures, as follows:

TABLE 12

Summary of CNS Vital Signs outcome measures

| CNS VS Outcome Measure | Average Change |
| --- | --- |
| Psychomotor Speed | +12.0% |
| Reaction Time | +10.3% |
| Cognitive Flexibility | +9.8% |
| Processing Speed | +9.6% |
| Executive Function | +9.8% |
| Motor Speed | +9.0% |
| Compiled Average All | +10.1% |

Since Braini LLC started human subject testing in 2018, no subjects have reported any serious adverse events.

Subjects were tested for Psychomotor Speed, Reaction Time, Cognitive Flexibility, Processing Speed, Executive Function, and Motor Speed.

Psychomotor Speed 35 of the 43 subjects (about 81%) saw improvement (positive change) in Psychomotor Speed after Braini® administration, ranging from about 1% to about 110% improvement compared to testing before Braini administration, as shown in FIG. 18. On average, Psychomotor Speed improved about 12% with Braini® administration. As also noted in FIG. 18, 5 subjects did not improve in the Psychomotor Speed category with Braini administration, and 3 subjects experienced no change.

Each Psychomotor Speed test result was noted as having a positive Validity Indicator under the test protocol (i.e. a reading of "Yes" to indicate valid test results). A negative Validity Indicator would suggest the test subject be evaluated to determine whether the subject understood the test, put forth their best effort, or has a clinical condition requiring further evaluation.

Reaction Time 35 of the 43 subjects (about 81%) saw improvement (positive change) in Reaction Time after Braini® administration, ranging from about 1% to about 40% improvement compared to testing before Braini administration, as shown in FIG. 19. On average, Reaction Time improved about 10% with Braini® administration. As also noted in FIG. 19, 6 subjects did not improve in the Reaction Time category with Braini administration, and 2 subjects experienced no change.

All but 2 test results (Subject ID #27, 36; test after Braini® administration) were noted as having a positive Validity Indicator under the Reaction Time test protocol (i.e. a reading of "Yes" to indicate valid test results). A negative Validity Indicator would suggest the test subject be evaluated to determine whether the subject understood the test, put forth their best effort, or has a clinical condition requiring further evaluation.

Cognitive Flexibility 31 of the 43 subjects (about 72%) saw improvement (positive change) in Cognitive Flexibility after Braini® administration, ranging from about 1% to about 51% improvement compared to testing before Braini administration, as shown in FIG. 20. On average, Cognitive Flexibility improved about 10% with Braini® administration. As also noted in FIG. 20, 11 subjects did not improve in the Cognitive Flexibility category with Braini administration, and 1 subject experienced no change.

All but 1 test result (Subject ID #17; test preceding Braini® administration) was noted as having a positive Validity Indicator under the Cognitive Flexibility test protocol (i.e. a reading of "Yes" to indicate valid test results). A negative Validity Indicator would suggest the test subject be evaluated to determine whether the subject understood the test, put forth their best effort, or has a clinical condition requiring further evaluation.

Processing Speed 33 of the 43 subjects (about 77%) saw improvement (positive change) in Processing Speed after Braini® administration, ranging from about 2% to about 60% improvement compared to testing before Braini administration, as shown in FIG. 21. On average, Processing Speed increased about 10% with Braini® administration. As also noted in FIG. 21, 8 subjects did not improve in the Processing Speed category with Braini administration, and 2 subjects experienced no change.

Each Processing Speed test result was noted as having a positive Validity Indicator under the test protocol (i.e. a reading of "Yes" to indicate valid test results). A negative Validity Indicator would suggest the test subject be evaluated to determine whether the subject understood the test, put forth their best effort, or has a clinical condition requiring further evaluation.

Executive Function 31 of the 43 subjects (about 72%) saw improvement (positive change) in Executive Function after Braini® administration, ranging from about 1% to about 50% improvement compared to testing before Braini administration, as shown in FIG. 22. On average, Executive Function increased about 10% with Braini® administration. As also noted in FIG. 22, 10 subjects did not improve in the Executive Function category with Braini administration, and 2 subjects experienced no change.

All but 2 test results (Subject ID #17, 32; test preceding Braini® administration) were noted as having a positive Validity Indicator under the Reaction Time test protocol (i.e. a reading of "Yes" to indicate valid test results). A negative Validity Indicator would suggest the test subject be evaluated to determine whether the subject understood the test, put forth their best effort, or has a clinical condition requiring further evaluation.

Motor Speed 30 of the 43 subjects (about 70%) saw improvement (positive change) in Motor Speed after Braini® administration, ranging from about 2% to about 97% improvement compared to testing before Braini administration, as shown in FIG. 23. On average, Motor Speed increased about 9% with Braini® administration. As also noted in FIG. 23, 9 subjects did not improve in the Motor Speed category with Braini administration, and 4 subjects experienced no change.

Each Motor Speed test result was noted as having a positive Validity Indicator under the test protocol (i.e. a reading of "Yes" to indicate valid test results). A negative Validity Indicator would suggest the test subject be evaluated to determine whether the subject understood the test, put forth their best effort, or has a clinical condition requiring further evaluation.

Parkinson's Disease

Two subjects in the above study were diagnosed with Parkinson's Disease prior to administration with Braini® capsules (Subject born 1952; 16-year diagnosis); Subject born 1953, 10 year diagnosis)). CNS Vital Signs Testing showed improvement in the subjects after (post-Braini®) about 30 consecutive days of Braini® administration, as compared with the subjects' test scores before Braini® administration (pre-Braini®), as shown in Tables 13 and 14.

TABLE 13

Improvements in Parkinson's Disease after 28 days' Braini ® Administration

| CNS Vital Signs Testing | Psycho-motor Speed | Re-action Time | Cognitive Flexibility | Pro-cessing Speed | Executive Functioning | Motor Speed |
|---|---|---|---|---|---|---|
| Pre-Braini ® | 81 | 111 | 105 | 98 | 103 | 75 |
| Post-Braini ® | 92 | 117 | 112 | 102 | 111 | 88 |
| Score Change | +11 | +6 | +7 | +4 | +8 | +13 |

TABLE 14

Improvements in Parkinson's Disease after 28 days' Braini ® Administration

| CNS Vital Signs Testing | Psycho-motor Speed | Re-action Time | Cognitive Flexibility | Pro-cessing Speed | Executive Functioning | Motor Speed |
|---|---|---|---|---|---|---|
| Pre-Braini ® | 104 | 102 | 93 | 99 | 94 | 108 |
| Post-Braini ® | 109 | 103 | 101 | 102 | 102 | 112 |
| Score Change | +5 | +1 | +8 | +3 | +8 | +4 |

Dysgraphia and Anxiety Disorder

A young subject (11 years old) in the above study was diagnosed with Dysgraphia and with Anxiety Disorder prior to administration with Braini® capsules. CNS Vital Signs Testing showed improvement in the subject after (post-Braini®) about 30 consecutive days of Braini® administration, as compared with the subject's test scores before Braini® administration (pre-Braini®), as shown in Table 15.

TABLE 15

Improvements in Dysgraphia and in Anxiety Disorder after 28 days' Braini ® Administration

| CNS Vital Signs Testing | Psycho-motor Speed | Re-action Time | Cognitive Flexibility | Pro-cessing Speed | Executive Functioning | Motor Speed |
|---|---|---|---|---|---|---|
| Pre-Braini ® | 90 | 63 | 75 | 84 | 74 | 97 |
| Post-Braini ® | 93 | 84 | 87 | 84 | 88 | 101 |
| Score Change | +3 | +21 | +12 | +0 | +14 | +4 |

Dementia

A subject in the above study was diagnosed with Early Onset Dementia prior to administration with Braini® capsules (Subject born 1962)). CNS Vital Signs Testing showed improvement in the subject after (post-Braini®) about 30 consecutive days of Braini® administration, as compared with the subject's test scores before Braini® administration (pre-Braini®), as shown in Table 16.

TABLE 16

Improvements in Early Onset Dementia after 30 days' Braini ® Administration

| CNS Vital Signs Testing | Psycho-motor Speed | Re-action Time | Cognitive Flexibility | Pro-cessing Speed | Executive Functioning | Motor Speed |
|---|---|---|---|---|---|---|
| Pre-Braini ® | 26 | 74 | 59 | 66 | 59 | 27 |
| Post-Braini ® | 54 | 96 | 89 | 80 | 88 | 53 |
| Score Change | +28 | +22 | +30 | +14 | +29 | +27 |

Attention-Deficit Disorders

Two subjects were diagnosed with ADHD (attention deficit-hyperactivity disorder) prior to administration with Braini® capsules (Subjects born 1990, 1983). CNS Vital Signs Testing showed improvement in the subject after (post-Braini®) about 30 consecutive days of Braini® administration, as compared with the subject's test scores before Braini® administration (pre-Braini®), as shown in Tables 17-18. Cognitive Flexibility and Executive Functioning in particular increased with Braini® administration in each subject; Processing Speed or Reaction Time also improved. This data is similar to that seen in dyslexic subjects that were administered Braini® capsules.

Without being bound by theory, these improvements may be due to subjects that have some difficulty with the uptake and/or processing of raw omega 3-6-9. For instance, these subjects may lack the ability to enzymatically digest raw omega. *B. arvensis* (Ahiflower®; NeurXcel®) oil according to the present invention includes omega SDA and GLA that have already been converted and may be easier for certain populations to absorb.

TABLE 17

Improvements in ADHD after 28 days' Braini ® Administration Subject born 1990

| CNS Vital Signs Testing | Psycho-motor Speed | Re-action Time | Cognitive Flexibility | Pro-cessing Speed | Executive Functioning | Motor Speed |
|---|---|---|---|---|---|---|
| Pre-Braini ® | 79 | 102 | 73 | 74 | 73 | 91 |
| Post-Braini ® | 93 | 102 | 106 | 98 | 108 | 93 |
| Score Change | +14 | +0 | +33 | +24 | +35 | +2 |

TABLE 18

Improvements in ADHD after 28 days' Braini ® Administration Subject born 1983

| CNS Vital Signs Testing | Psycho-motor Speed | Re-action Time | Cognitive Flexibility | Pro-cessing Speed | Executive Functioning | Motor Speed |
|---|---|---|---|---|---|---|
| Pre-Braini ® | 103 | 73 | 108 | 10 | 107 | 102 |
| Post-Braini ® | 106 | 101 | 118 | 10 | 122 | 104 |
| Score Change | +3 | +28 | +10 | −2 | +15 | +2 |

Example 18

Improvement in Concentration in Young Adults with Braini® Administration

In a randomized double-blinded, placebo-controlled clinical trial with young adults as subjects, aged 18-30, the administration of Braini® improved concentration by 85%, as compared with placebo.

Figure 24:
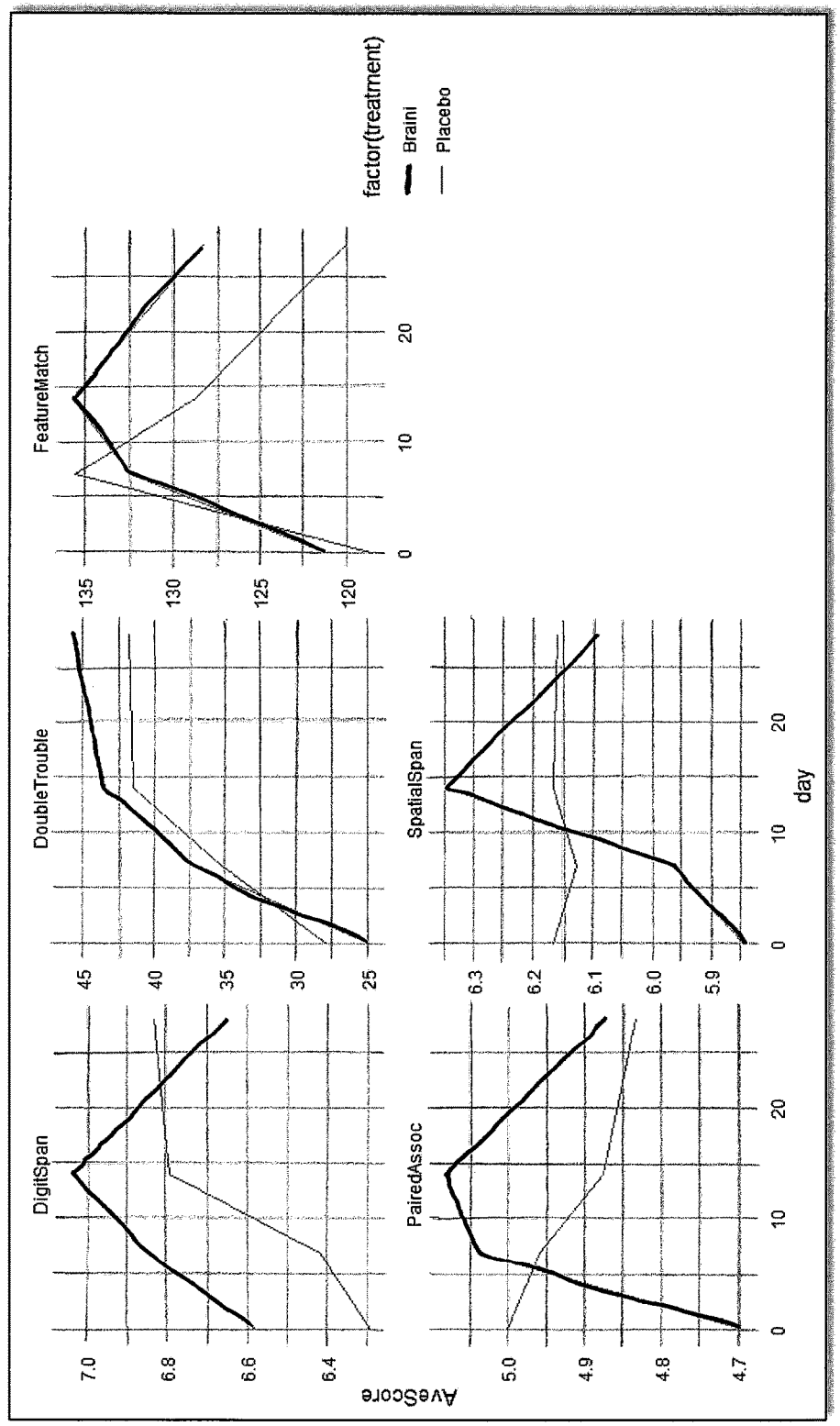
FIG. 24 is a series of graphs including a Cambridge Brain Sciences DoubleTrouble graph, showing improved concentration in subjects administered Braini®.

During the study, 23 active subjects were administered Braini® for 28 days, and 17 placebo subjects took a placebo composition for the same number of days. The Double-Trouble concentration test (Cambridge Brain Sciences, Toronto, Ontario, Canada) was taken by each subject as a baseline before beginning administration of Braini® or placebo, and then taken again upon completion of the entire course. The Double Trouble test is based upon the Stroop task and assesses response inhibition, that is, the ability to concentrate on relevant information to make an appropriate response, even when distracting information or interference is present. Response inhibition is a key component of concentration. As mentioned above, the group that was administered Braini® experienced an 85% improvement in the Double Trouble concentration test. See for instance Table 19 below, showing in part an increase in the Double-Trouble concentration scores of subjects administered Braini®, from 24.73 to about 45.74, showing 85% improvement; and see FIG. 24, where the upper line reaching past an average score of 45 in the DoubleTrouble entry shows Braini® subjects' improvement in concentration, and the lower line plateauing between an average score of 40 and 42.5 represents average placebo subject scores.

Signs (Morrisville, N.C.) computerized neuro-cognitive performance self-testing suite. After the dietary study concluded, 10 outcome measures were assessed independently between the active Braini® (A) and placebo (P) cohorts in each age group by the pharmaceutical statistical analysis firm Pharmalnitiatives (Chapel Hill, N.C.).

Young Adult Subjects

The university IRB-reviewed randomized double-blinded placebo-controlled study of young adult subjects included 30 participants with 14 active (administered Braini®) and 16 placebo subjects. Overall, 92% of all participants improved by at least 2.5% on the following 6 CNS Vital Signs tests: Psychomotor Speed, Reaction Time, Cognitive Flexibility, Processing Speed, Executive Function, Motor Speed. 61% of all subjects improved by at least 2.5% to 15.1% in Cognitive Flexibility.

77% of all subjects improved by at least 2.5% to 19.5% in Executive Function.

One subject improved 42.5% in Processing Speed; another subject improved by 37.3%, and a third improved by 29%.

Executive Function

Of the 6 CNS Vital Signs outcome measures scored for each subject in the above-described trials, scores related to Executive Function showed greatest improvement. As discussed above, Executive Function is one of the most difficult neuro-cognitive performance measures to influence, especially without stimulants. Executive Function measures how well a subject recognizes rules, categories, and manages or navigates rapid decision making, and relates to one's ability to sequence tasks and manage multiple tasks simultaneously

TABLE 19

|  | time | n | mean | sd |  | time | n | mean | sd |
|---|---|---|---|---|---|---|---|---|---|
|  | DigitSpan |  |  |  |  | PairedAssoc |  |  |  |
| Placebo | Baseline | 24 | 6.29 | 1.12 | Placebo | Baseline | 24 | 5.00 | 1.02 |
| Placebo | Post | 18 | 6.83 | 1.29 | Placebo | Post | 18 | 4.83 | 1.54 |
| Braini | Baseline | 26 | 6.58 | 1.10 | Braini | Baseline | 26 | 4.69 | 0.79 |
| Braini | Post | 23 | 6.65 | 1.19 | Braini | Post | 23 | 4.87 | 0.69 |
|  | DoubleTrouble |  |  |  |  | SpatialSpan |  |  |  |
| Placebo | Baseline | 22 | 27.73 | 16.17 | Placebo | Baseline | 24 | 6.17 | 0.87 |
| Placebo | Post | 19 | 41.74 | 16.28 | Placebo | Post | 19 | 6.16 | 1.12 |
| Braini | Baseline | 26 | 24.73 | 15.89 | Braini | Baseline | 26 | 5.85 | 1.01 |
| Braini | Post | 23 | 45.74 | 14.79 | Braini | Post | 23 | 6.09 | 0.90 |
|  | FeatureMatch |  |  |  |  |  |  |  |  |
| Placebo | Baseline | 24 | 118.58 | 34.53 |  |  |  |  |  |
| Placebo | Post | 18 | 120.00 | 37.76 |  |  |  |  |  |
| Braini | Baseline | 26 | 121.15 | 30.59 |  |  |  |  |  |
| Braini | Post | 23 | 128.13 | 37.58 |  |  |  |  |  |

Example 19

Improved Executive Function in Braini® Clinical Trials for Young Adults and Seniors In two randomized double-blinded, placebo-controlled clinical trials, one in healthy young adults (ages 18-30) and one in healthy seniors (ages 50-80), subjects took either the Braini® supplement or placebo as directed for 28 days.

The trials assessed subjects' overall cognitive performance at baseline prior to starting administration of Braini® or placebo, and then again at 28 days, using the CNS Vital as well as tracking and responding to a set of instructions. This is a shifting attention test.

Both studies had to be curtailed because of the coronavirus pandemic, which limited subject recruitment and made it harder to achieve statistical significance. Nonetheless, after the clinical trial concluded and the study was unblinded, the following key findings were identified.

Figure 25:
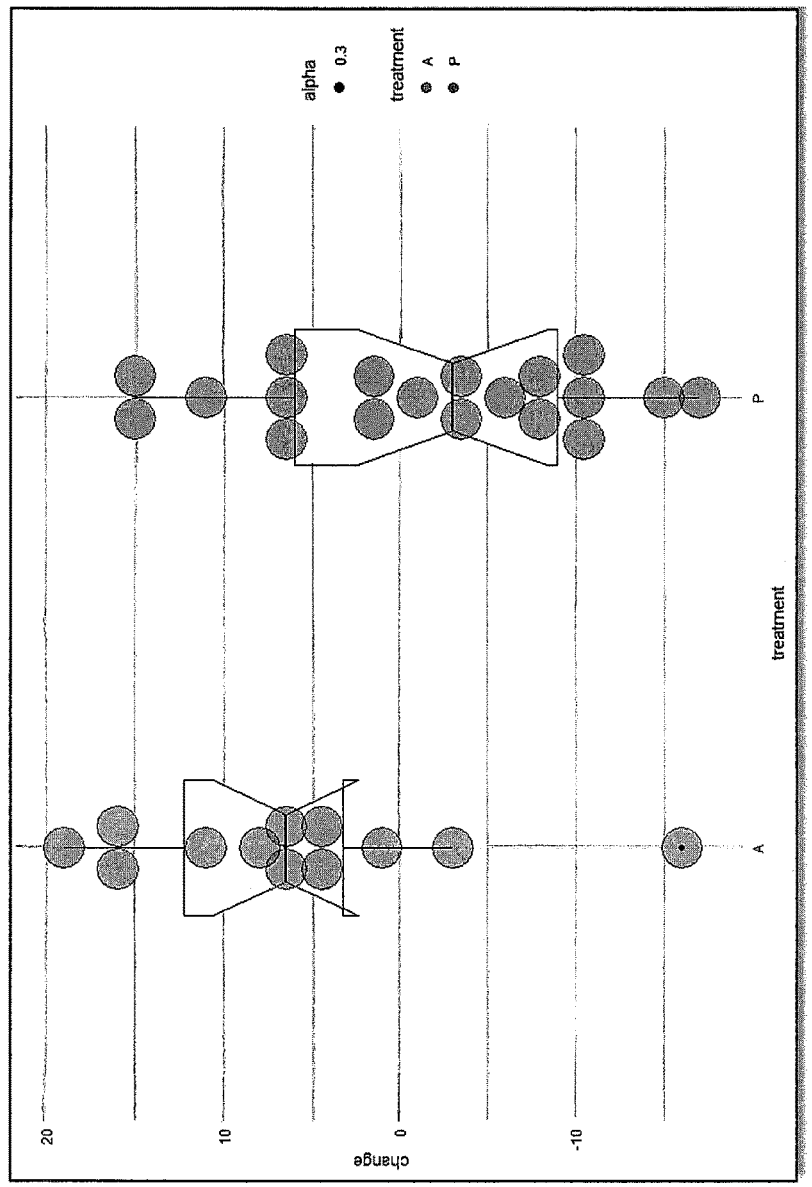
FIG. 25 is a non-parametric model showing statistically significant improvement in Executive Function in healthy young adult human subjects administered Braini® (A) compositions of this invention, as compared with subjects administered a Placebo (P) composition.

See for instance FIG. 25, a non-parametric model (Asymptotic Wilcoxon-Mann-Whitney Test) showing improvements in Executive Function (p=0.03; Z=2.152) in young adult subjects administered Braini® (A) compositions of this invention, compared with a Placebo (P) composition.

TABLE 20

| Treatment | Baseline (mean) | Baseline (SD) | Change (mean) | Change (SD) |
|---|---|---|---|---|
| A (Braini ®) | 101.7857 | 17.40989 | 6.166667 | 9.504385 |
| P (Placebo) | 110.6000 | 12.71303 | −1.578947 | 9.645470 |

Some slides indicate that baseline scores were lower in those administered Braini® compositions, showing that even if the placebo cohort performed better at Baseline on average, the fact they were taking a placebo still reverted to almost no overall change in this outcome measure. If the results were biased because this cohort was "smarter" they would be expected to achieve a higher overall improvement after 28 days, but this didn't happen.

Figure 26:
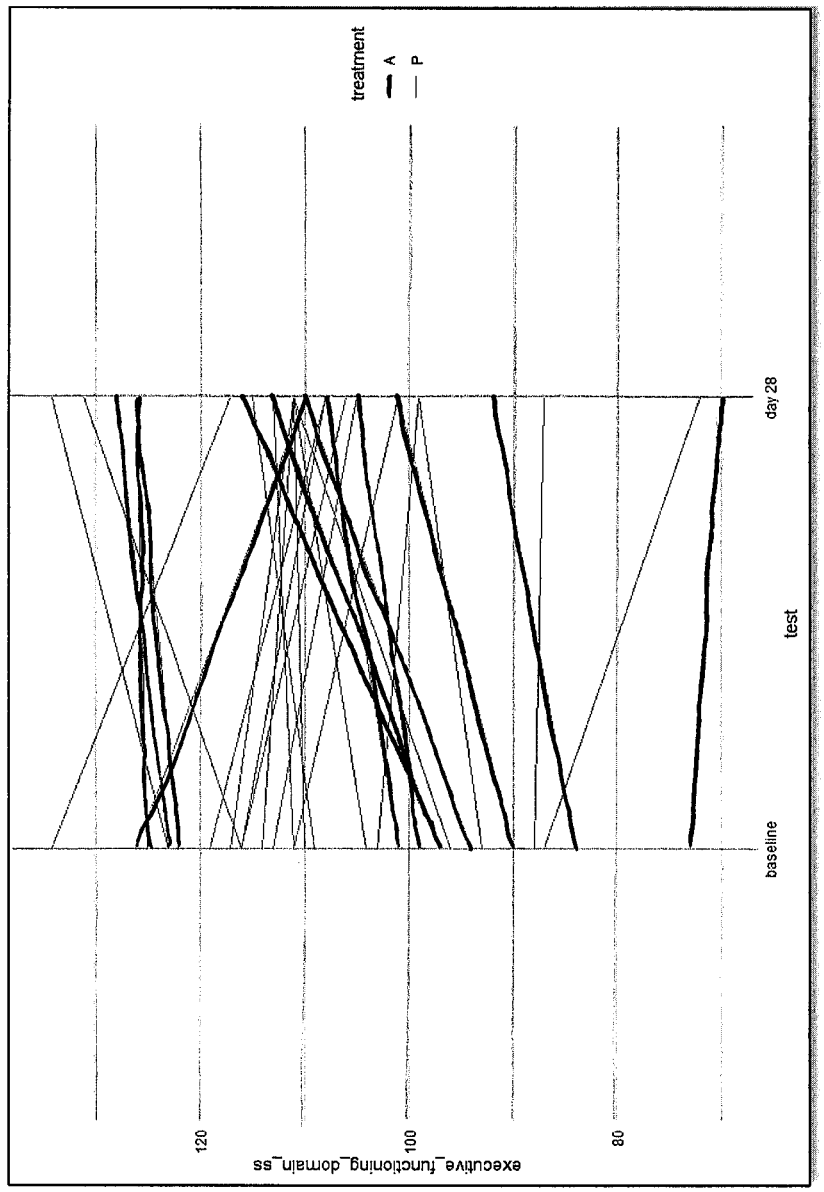
FIG. 26 is a parametric model showing statistically significant improvement in Executive Function in healthy young adult human subjects administered Braini® (A) compositions of this invention, as compared with subjects administered a Placebo (P) composition.

In FIG. 26, a parametric model shows that young adult subjects taking Braini® (A, Active) improved in Executive Function performance consistently with administration Braini® (A) regardless of baseline, as compared with Placebo (P). Placebo results were mixed, but did not show strong regression to the mean.

TABLE 21

Parametric Model, Residuals and Coefficients

| | | Residuals | | |
|---|---|---|---|---|
| Min | 1Q | Median | 3Q | Max |
| −22.1667 | −6.4211 | −0.1667 | 7.5789 | 16.5789 |

| | | Coefficients | | |
|---|---|---|---|---|
| | Estimate | Std. Error | t value | Percentile |
| (Intercept) | 6.167 | 2.769 | 2.227 | 0.0339* |
| Treatment (P) | −7.746 | 3.537 | −2.190 | 0.0367* |

*Significance code 0.05
Residual standard error: 9.592 on 29 degrees of freedom (3 observations deleted due to subject absence). Multiple R-squared: 0.1419, Adjusted R-squared: 0.1123, F-statistic: 4.796 on 1 and 29 DF, p-value: 0.03672

Figure 27:
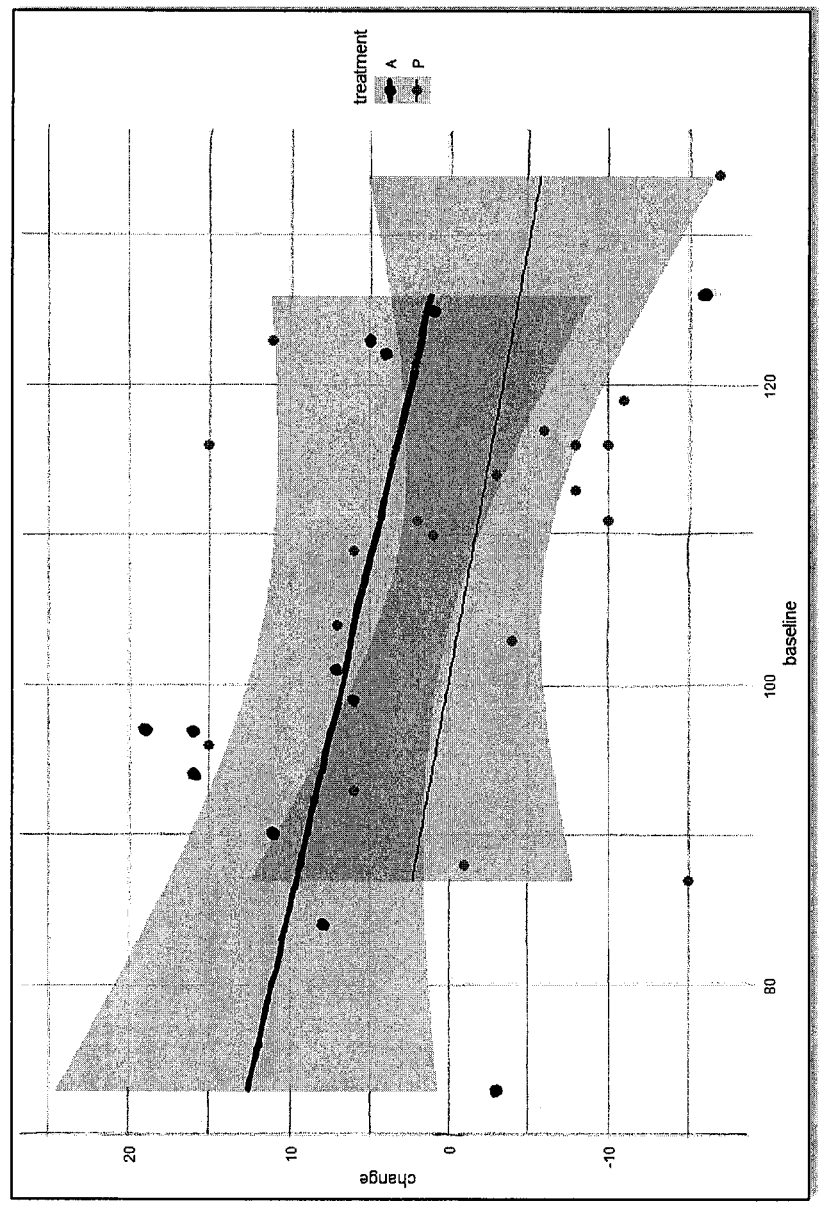
FIG. 27 is a multiple regression model showing improvement in Executive Function in healthy young adult human subjects administered Braini® (A) compositions of this invention, as compared with subjects administered a Placebo (P) composition, based on baseline analyses.

In FIG. 27, a multiple regression model incorporating baseline scores shows improvement in Executive Function in healthy young adult subjects with administration of Braini® (A) over Placebo (P) (p=0.08).

Parallel lines with downward slopes support consistent effects across baseline scores.

TABLE 22

| | | Residuals | | |
|---|---|---|---|---|
| Min | 1Q | Median | 3Q | Max |
| −17.8865 | −5.4223 | −0.5217 | 5.8953 | 17.8757 |

| | | Coefficients | | |
|---|---|---|---|---|
| | Estimate | Std. Error | t value | Percentile |
| (Intercept) | 26.5496 | 12.6713 | 2.095 | 0.0453* |
| Treatment (P) | −6.3765 | 3.5363 | −1.803 | 0.0821• |
| Baseline | −0.1987 | 0.1207 | −1.646 | 0.1109 |

*Significance code 0.05;
•Significance code 0.1
Residual standard error: 9.321 on 28 degrees of freedom (3 observations deleted due to subject absence). Multiple R-squared: 0.2176, Adjusted R-squared: 0.1617, F-statistic: 3.894 on 2 and 28 DF, p-value: 0.0322

Figure 28:
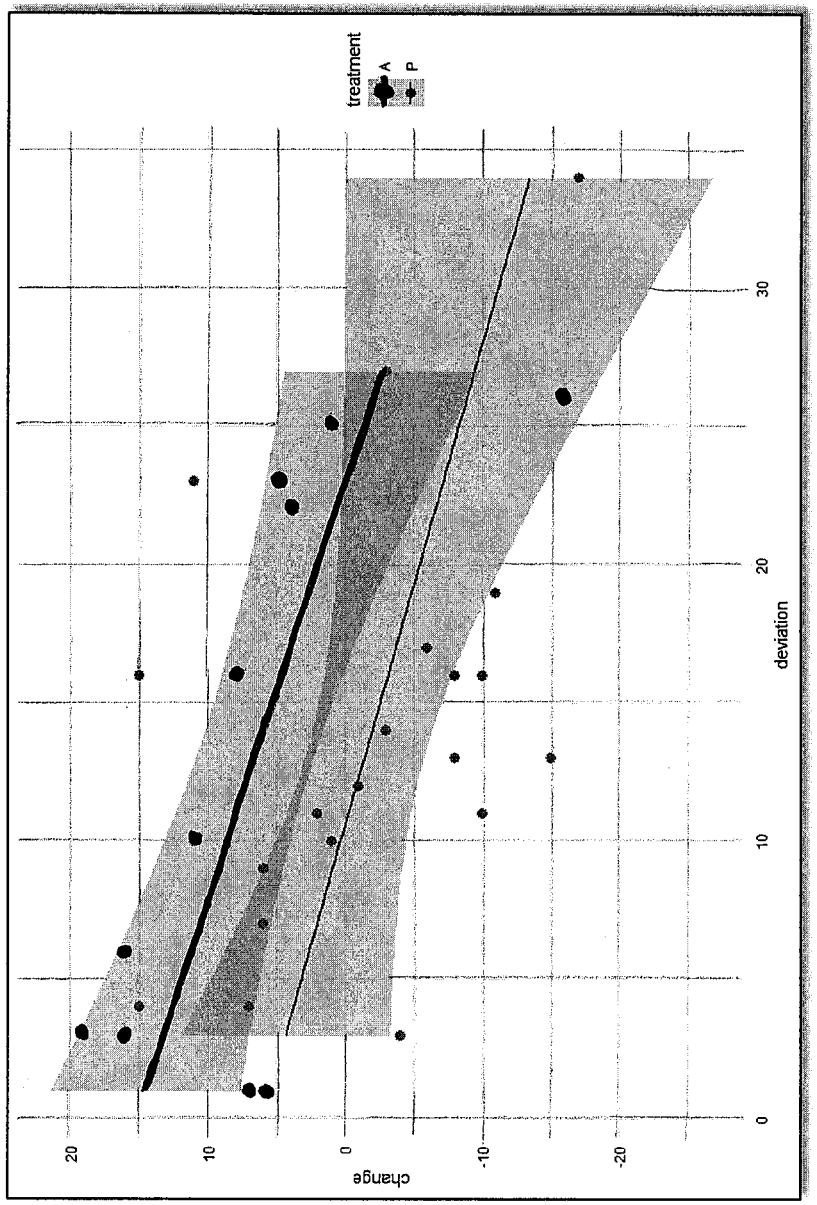
FIG. 28 is a multiple regression model showing improvement in Executive Function in healthy young adult human subjects administered Braini® (A) compositions of this invention, as compared with subjects administered a Placebo (P) composition, based on analysis of absolute deviation from the scaled mean of 100.

FIG. 28 improves the above multiple regression model by analyzing absolute deviation from the scaled mean of 100 instead of baseline. The effect of very high values is significant, showing clear and beneficial improvement in young adult subjects administered Braini® (A) as compared with subjects administered Placebo (P).

TABLE 23

| | | Residuals | | |
|---|---|---|---|---|
| Min | 1Q | Median | 3Q | Max |
| −14.4238 | −6.2144 | 0.5441 | 3.5068 | 18.6507 |

| | | Coefficients | | |
|---|---|---|---|---|
| | Estimate | Std. Error | t value | Percentile |
| (Intercept) | 14.6370 | 3.2955 | 4.441 | 0.000127*** |
| Treatment (P) | −7.9453 | 2.9698 | −2.675 | 0.012328* |
| Baseline | −0.6236 | 0.1720 | −3.626 | 0.001134** |

*Significance code 0*, 0.001**, 0.01*
Residual standard error: 8.053 on 28 degrees of freedom (3 observations deleted due to subject absence). Multiple R-squared: 0.4161, Adjusted R-squared: 0.3744, F-statistic: 9.976 on 2 and 28 DF, p-value: 0.0005356

Discussion

Executive Function in Healthy Young Adults

In healthy young adults aged 18-30, subjects taking Braini® for 28 days experienced significant improvement over placebo in Executive Function (p=00215). The Braini subjects improved by an average of 7.8% over the placebo subjects, with changes from baseline ranging from −12.7% to +19.6% in the Braini cohort compared with a range of −17.2% to +15.6% in the placebo cohort. Also, the researchers found that subjects taking Braini® experienced significantly improved CNS correct response shifting attention reaction time (SAT-RT, important in Executive Function) compared with placebo by an average $\frac{1}{10}^{th}$ of a second (p=0.007). Researchers consider a p-value of less than 0.05 to be significant.

Senior Adult Subjects

A university IRB-reviewed randomized double-blinded placebo-controlled study of senior adult subjects (ages 50-80) included 30 participants with 14 active (administered Braini®) and 16 placebo subjects. The trial was suspended early due to the coronavirus pandemic, so statistical power in the subject pools was difficult to achieve.

As a cohort, the baseline scores of the active Braini® subject group was extremely high, with the vast majority of the participants scoring in the "high function" category (>110) in 1 or more CNS outcome measures.

92.8% of active (Braini®) subjects had 2.5% or better improvement on at least 1 of 6 cognitive performance measures.

Executive Function in Healthy Seniors

Healthy high-functioning seniors aged 55-80, after oral administration of Braini® for 28 days, experienced significant improvement in Executive Function including SAT-RT vs placebo (p value of 0.05) achieving an average of 66.8 millisecond improvement in this parameter.

Reaction Time in Healthy Young Adult Subjects and in Healthy Seniors

In both age groups, subjects experiencing a slower baseline Reaction Time before Braini® administration experienced greater improvement in Reaction Times after 28 days of Braini® administration, compared to subjects taking placebo.

Example 20

Continuing Evidence of Dramatic Improvement in Executive Function and Cognitive Flexibility Outcome Measures in Subjects with Dyslexia and/or Self-Reported Learning Differences A young adult (age 18) and a senior adult (age 62) were orally administered Braini® capsules of this invention, as described above, for 28 days. In these and other dyslexic subjects, the lowest test scores are typically in Executive Function and Cognitive Flexibility. All tests and scores shown in Table 24 (young adult) below had a positive Validity Indicator. In Table 25, a negative Validity Indicator is indicated by "¹".

As shown in the below Tables, Cognitive Flexibility and Executive Function dramatically increased in the young adult and senior adult tested, from Low Average (young adult) or Very Low Average (senior adult) to Average functioning in these areas for both age groups. Other improvements in this area may also be seen in the below Tables and other data provided.

Without being bound by theory, these improvements may be due to subjects, such as those presenting with dyslexia and/or ADHD, that have difficulty with the uptake and/or processing of raw omega 3-6-9. For instance, these subjects may lack the ability to enzymatically digest raw omega. *B. arvensis* (Ahiflower®; NeurXcel®) oil according to the present invention includes omega SDA and GLA that have already been converted and may be easier for certain populations to absorb.

In the young adult subject with dyslexia discussed in this Example, evidence of dyslexia in CNS Vital Signs scores was accompanied by a diagnosis of calcification of the heart, possibly representing that the subject's body cannot break down omegas and possibly, rather, accumulates them. Fats were severely restricted from his diet, including healthy fats such as from nuts and avocados, because people with his condition cannot digest them. The subject responded very well to 30 days' administration of Braini® capsules. Without being bound by theory, Braini® capsules may have improved absorption and/or processing of SDA and GLA and facilitated SDA and GLA entry with *B. mori* fiber of this invention into the brain. *B. mori* fiber (Peptylin®; BF-7; of the present invention) has been shown to reduce ischemic stroke in animal models.

TABLE 24

Improved Cognitive Flexibility and Executive Function in Young Adult having Dyslexia

| Patient Profile | Pre-Administration of Braini ® | | | | Post-Administration of Braini ® | | | |
|---|---|---|---|---|---|---|---|---|
| (Young Adult) Domain/Scores | Patient Score | Standard Score | Percentile | Status | Patient Score | Standard Score | Percentile | Status |
| Verbal Memory | 58 | 121 | 92 | Above Ave. | 55 | 109 | 73 | Ave. |
| Psychomotor Speed | 175 | 99 | 47 | Ave. | 160 | 90 | 25 | Ave. |
| Reaction Time* | 841 | 59 | 1 | Very Low | 790 | 69 | 2 | Very Low |
| Cognitive Flexibility | 33 | 81 | 10 | Low Ave. | 49 | 104 | 61 | Ave. |
| Processing Speed | 59 | 98 | 45 | Ave. | 54 | 92 | 30 | Ave. |
| Executive Function | 36 | 84 | 14 | Low Ave. | 51 | 105 | 63 | Ave. |
| Motor Speed | 115 | 100 | 50 | Ave. | 101 | 89 | 23 | Low Ave. |

*Lower scores are better. (If no *, higher scores are better/an improvement).

Test Results—Pre-Braini® Administration (Young Adult)

TABLE 24A

Verbal Memory Test (VBM)

| Tested information | Score | Standard | Percentile |
|---|---|---|---|
| Correct Hits - Immediate | 15 | 118 | 88 |
| Correct Passes - Immediate | 13 | 84 | 14 |
| Correct Hits - Delay | 15 | 123 | 94 |
| Correct Passes - Delay | 15 | 113 | 81 |

Verbal Memory test: Subjects have to remember 15 words and recognize them in a field of 15 distractors. The test is repeated at the end of the battery. The VBM test measures how well a subject can recognize, remember, and retrieve words e.g. exploit or attend literal representations or attribute. "Correct Hits" refers to the number of target words recognized. Low scores indicate verbal memory impairment.

TABLE 24B

Finger Tapping Test (FTT)

| Tested Information | Score | Standard | Percentile |
|---|---|---|---|
| Right Taps Average | 61 | 102 | 55 |
| Left Taps Average | 54 | 97 | 42 |

The FTT is a test of motor speed and fine motor control ability. There are three rounds of tapping with each hand. The FTT test measures the speed and the number of finger-taps with each hand. Low scores indicate motor slowing. Speed of manual motor activity varies with handedness. Most people are faster with their preferred hand but not always.

TABLE 24C

Symbol Digit Coding (SDC)

| Tested Information | Score | Standard | Percentile |
|---|---|---|---|
| Correct Responses | 60 | 98 | 45 |
| Errors* | 1 | 103 | 58 |

The SDC test measures speed of processing and draw upon several cognitive processes simultaneously, such as visual scanning, visual perception, visual memory, and motor functions. Errors may be due to impulsive responding, misperception, or confusion.

TABLE 24D

Stroop Test (ST)

| Tested Information | Score | Standard | Percentile |
|---|---|---|---|
| Simple Reaction Time* | 411 | 54 | 1 |
| Complex Reaction Time Correct* | 787 | 61 | 1 |
| Stroop Reaction Time Correct* | 895 | 65 | 1 |
| Stroop Commission Errors* | 3 | 83 | 13 |

The ST measures simple and complex reaction time, inhibition/disinhibition, mental flexibility or directed attention. The ST helps assess how well a subject is able to adapt to rapidly changing and increasingly complex set of directions. Prolonged reaction times indicate cognitive slowing/impairment. Errors may be due to impulsive responding, misperception, or confusion.

Test Results—Post-Braini® Administration (Young Adult)

TABLE 24E

Verbal Memory Test (VBM)

| Sub-tests | Score | Standard | Percentile |
|---|---|---|---|
| Correct Hits - Immediate | 14 | 110 | 75 |
| Correct Passes - Immediate | 15 | 110 | 75 |

TABLE 24E-continued

Verbal Memory Test (VBM)

| Sub-tests | Score | Standard | Percentile |
|---|---|---|---|
| Correct Hits - Delay | 12 | 104 | 61 |
| Correct Passes - Delay | 14 | 100 | 50 |

TABLE 24F

Finger Tapping Test (FTT)

| Sub-tests | Score | Standard | Percentile |
|---|---|---|---|
| Right Taps Average | 56 | 95 | 37 |
| Left Taps Average | 45 | 83 | 13 |

TABLE 24G

Symbol Digit Coding (SDC)

| Tested Information | Score | Standard | Percentile |
|---|---|---|---|
| Correct Responses | 59 | 97 | 42 |
| Errors* | 5 | 62 | 1 |

TABLE 24H

Stroop Test (ST)

| Tested Information | Score | Standard | Percentile |
|---|---|---|---|
| Simple Reaction Time* | 396 | 59 | 1 |
| Complex Reaction Time Correct* | 692 | 79 | 8 |
| Stroop Reaction Time Correct* | 887 | 67 | 1 |
| Stroop Commission Errors* | 2 | 93 | 32 |

TABLE 25

Improved Cognitive Flexibility and Executive Function in Senior Adult Having Dyslexia

| Patient Profile (Senior Adult) Domain/Scores | Pre-Administration of Braini ® | | | | Post-Administration of Braini ® | | | |
|---|---|---|---|---|---|---|---|---|
| | Patient Score | Standard Score | Percentile | Status | Patient Score | Standard Score | Percentile | Status |
| Verbal Memory | 46 | 87 | 19 | Low Ave. | 48 | 94 | 34 | Ave. |
| Psychomotor Speed | 163 | 107 | 68 | Ave. | 174 | 114 | 82 | Above Ave. |
| Reaction Time* | 841 | 84 | 14 | Low Ave. | 740 | 96 | 40 | Ave. |
| Cognitive Flexibility | −33[1] | 38 | 1 | Very Low | 42 | 105 | 63 | Ave. |
| Processing Speed | 47 | 105 | 63 | Ave. | 55 | 115 | 84 | Above Ave. |
| Executive Function | −32[1] | 37 | 1 | Very Low | 43 | 104 | 61 | Ave. |
| Motor Speed | 116 | 108 | 70 | Ave. | 118 | 110 | 75 | Above Ave. |

*Lower scores are better. (If no *, higher scores are better/an improvement).
[1]Indicates a negative Validity Indicator.

Test Results—Pre-Braini® Administration (Senior Adult)

TABLE 25A

Verbal Memory Test (VBM)

| Tested Information | Score | Standard | Percentile |
|---|---|---|---|
| Correct Hits - Immediate | 12 | 102 | 55 |
| Correct Passes - Immediate | 13 | 86 | 18 |

TABLE 25A-continued

Verbal Memory Test (VBM)

| Tested Information | Score | Standard | Percentile |
|---|---|---|---|
| Correct Hits - Delay | 11 | 104 | 61 |
| Correct Passes - Delay | 10 | 64 | 1 |

TABLE 25B

Finger Tapping Test (FTT)

| Tested Information | Score | Standard | Percentile |
|---|---|---|---|
| Right Taps Average | 62 | 113 | 81 |
| Left Taps Average | 54 | 102 | 55 |

TABLE 25C

Symbol Digit Coding (SDC)

| Tested Information | Score | Standard | Percentile |
|---|---|---|---|
| Correct Responses | 47 | 103 | 58 |
| Errors* | 0 | 114 | 82 |

TABLE 25D

Stroop Test (ST)

| Tested Information | Score | Standard | Percentile |
|---|---|---|---|
| Simple Reaction Time* | 313 | 98 | 45 |
| Complex Reaction Time Correct* | 726 | 91 | 27 |
| Stroop Reaction Time Correct* | 956 | 81 | 10 |
| Stroop Commission Errors* | 1 | 103 | 58 |

Test Results—Post-Braini® Administration

TABLE 25E

Verbal Memory Test (VBM)

| Tested Information | Score | Standard | Percentile |
|---|---|---|---|
| Correct Hits - Immediate | 12 | 102 | 55 |
| Correct Passes - Immediate | 13 | 86 | 18 |
| Correct Hits - Delay | 11 | 104 | 61 |
| Correct Passes - Delay | 12 | 82 | 12 |

TABLE 25F

Finger Tapping Test (FTT)

| Tested Information | Score | Standard | Percentile |
|---|---|---|---|
| Right Taps Average | 63 | 114 | 82 |
| Left Taps Average | 55 | 104 | 61 |

TABLE 25G

Symbol Digit Coding (SDC)

| Tested Information | Score | Standard | Percentile |
|---|---|---|---|
| Correct Responses | 56 | 115 | 84 |
| Errors* | 1 | 103 | 58 |

TABLE 25H

Stroop Test (ST)

| Tested Information | Score | Standard | Percentile |
|---|---|---|---|
| Simple Reaction Time* | 293 | 101 | 53 |
| Complex Reaction Time Correct* | 653 | 99 | 47 |
| Stroop Reaction Time Correct* | 827 | 94 | 34 |
| Stroop Commission Errors* | 1 | 103 | 58 |

In dyslexic subjects, the lowest test scores are typically in Executive Function and Cognitive Flexibility. Dyslexic subjects administered a composition according to the present invention (Braini® capsules, as above), for about 28 days, or more, showed very good, even strong improvement in CNS Vital Signs test outcome measures.

Executive Function is tightly linked to ADHD and other attention deficit disorders. Four of the CNS Vital Signs tests used in the Braini® clinical trials described in this application are used to measure ADHD. They are Executive Function, Reaction Time, Cognitive Flexibility and Processing Speed. CNS Vital Signs is used throughout the world as a clinical tool to evaluate and manage ADHD. Executive Functioning, sometimes called executive control system, is generally considered a frontal lobe neurocognitive system that controls and manages other cognitive processes. It is considered a higher☐ order brain function, which includes attention, behavioral planning and response inhibition, and the manipulation of information in problem☐solving tasks. Executive Function is sometimes referred to as the "command and control" or the "conductor" of many cognitive skills (Iverson et al., J. Affect Disord. 132(3):360-367 (2011)). Likewise, Cognitive Flexibility is related to Mood Disorders according to Iverson et al. and CNS Vital Signs reports.

Example 21

A senior adult healthy woman self-administered Braini® capsules as described above, daily for about 23 months. CNS Vital Signs testing was conducted and all scores improved over time.

Specifically, the subject's Psychomotor Speed improved from 111 to 138 (24% improvement), and the subject's Motor Speed improved from 120 to 141 (18% improvement); test scores are capped at 130 in terms of percentile ranking and the like.

The subject's greatest improvement was seen in Processing Speed, improving from 88 to 121 (38% improvement). Other improvements include in Reaction Time (from 96 to 102; 6% improvement), Cognitive Flexibility (from 93 to 107; 15% improvement), and Executive Function (from 94 to 109; 16% improvement).

These results show that improvements from Braini® show benefit over time, including providing neuroprotection with consistent administration.

Example 22

In this Example, Scanning Electron Microscope (SEM) images of the Braini® composition described above, and its individual constituents Peptylin® powder, NeurXcel powder, and wild blueberry powder, show that the Braini® composition contains bonding between the ingredients and interactions to indicate the formation of a new physical structure.

As shown below, each of the three initial components (Peptylin® powder, NeurXcel powder, and wild blueberry powder) has a distinctive morphology that allows it to be easily identified by shape in the Braini® compositions tested. The Braini® compositions all comprise and in an embodiment consist of agglomerates where the individual particles are made up of two or more of the initial components.

In the unencapsulated powders, there is merging between the primary particles making up the Braini® agglomerates, more than would be seen for mere electrostatic attraction.

In the encapsulated formulations, the degree of merging and interaction between the ingredients is even more evident than in the unencapsulated materials. There is a clear change in morphology and a skin of some material not seen in the micrographs of the initial ingredients appears to be covering the agglomerates and bonding them together.

Materials:
Braini® Capsules
Braini Lex® Capsules
Braini® Powder
Braini Lex® Powder
NeurXcel® lot #19100359c
Peptylin® (BF-7) lot #71908002
Wild dried blueberry powder lot #18355

Methods:

Capsules were split with a scalpel and the powder inside analyzed. For each sample, a small amount of powder was dispersed onto a Leit tab (sticky pad made of carbon) and mounted on an aluminum stub. Each was coated with a 20 nm thick layer of gold using a Polaron T sputter coater fitted with a FT7690 film thickness monitor.

Images were obtained with a Carl Zeiss Evo-60 microscope fitted with a LaB6 emitter running at 1.96 A, the second emission current. The working distance was between 7-8 mm, the EHT 20 kV, 100 pA probe current, chamber vacuum of 5×10-6 mBar. Images were collected using the Thornley-Everhart secondary electron detector. Beam alignment was checked and corrected hourly.

Figure 29:
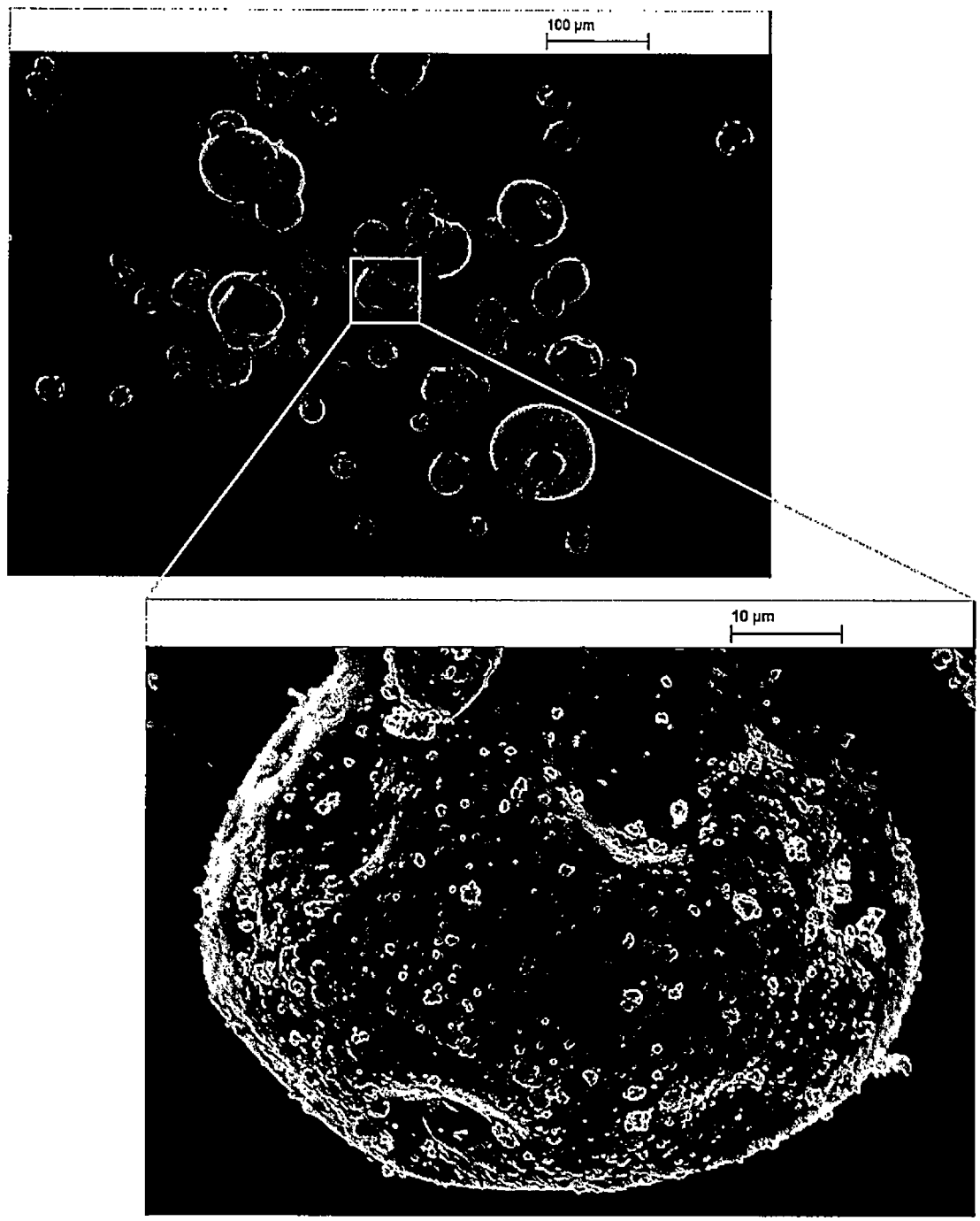
FIG. 29 is a scanning electron micrograph showing NeurXcel® powder in discrete, 10-100 um spheres. (Scale: top: 100 um; bottom: 10 um).

Results:

NeurXcel® powder is shown as discrete spheres in FIG. 29, ranging from 10-100 um in diameter. The surface of the spheres is pitted and has a covering of smaller particles of the order of 0.5 to 1 um in diameter. (Scale top: 100 um; bottom: 10 um).

Figure 30:
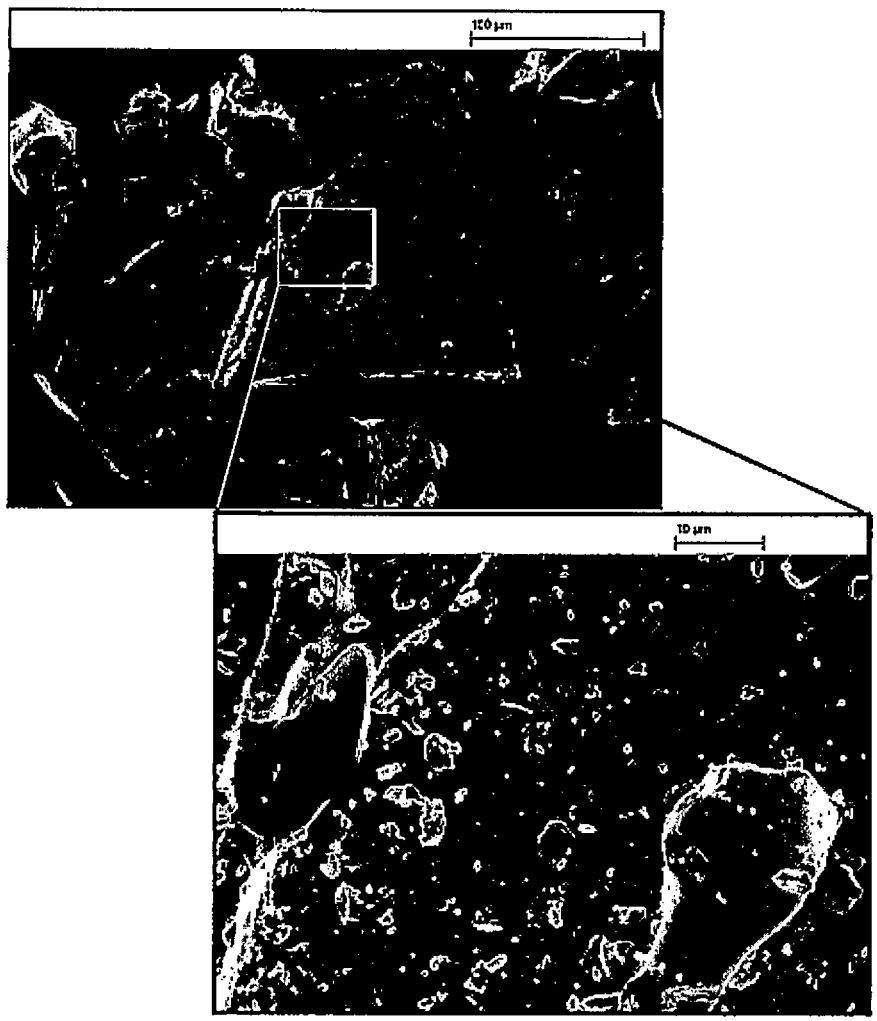
FIG. 30 is a scanning electron micrograph showing Peptylin® powder as an angular crystal-like material. (Scale top: 100 um; bottom: 10 um).

Peptylin® powder is shown in the form of a dispersion of angular crystal-like material in FIG. 30. Particle size varies from the millimeter to micron range. The surface of the larger particles are covered with smaller crystalline particles in the sub-micron size range. (Scale top: 100 um; bottom: 10 um).

Figure 31:
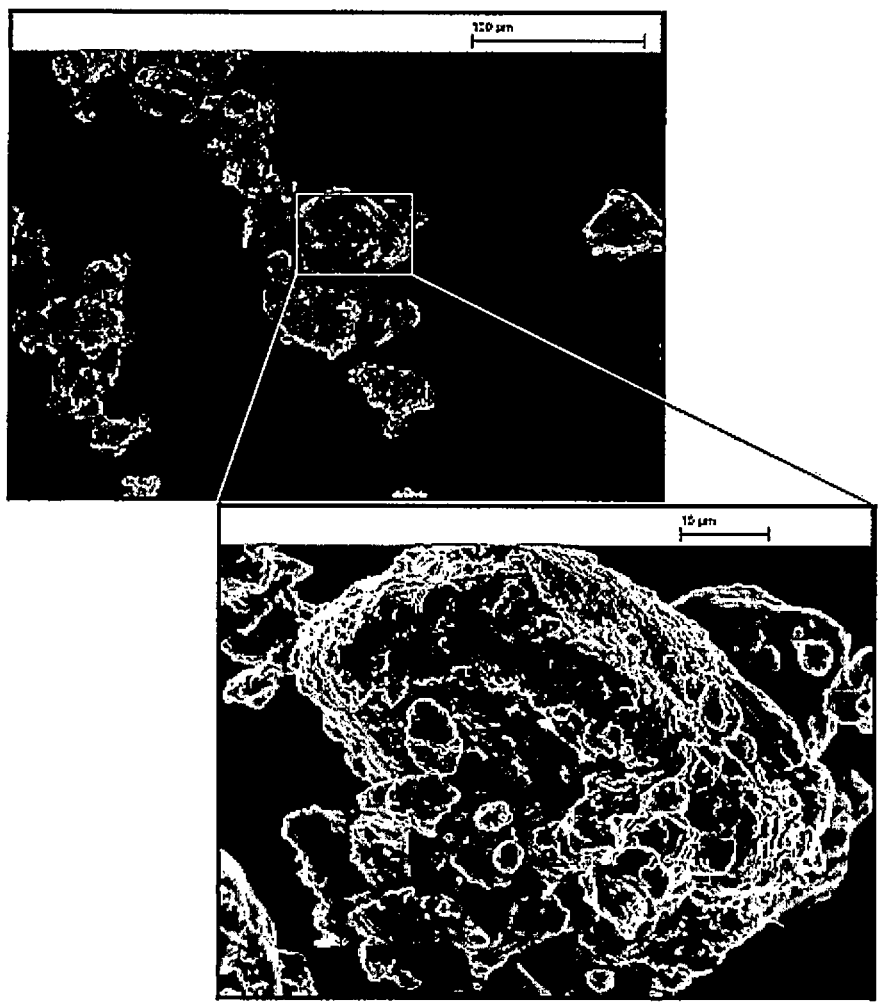
FIG. 31 is a scanning electron micrograph showing Wild blueberry powder particles ranging from 10-50 um across. (Scale top: 100 um; bottom: 10 um).

Wild blueberry powder is shown as relatively amorphous particles in FIG. 31 ranging from 10-50 um across. (Scale top: 100 um; bottom: 10 um).

Figure 32:
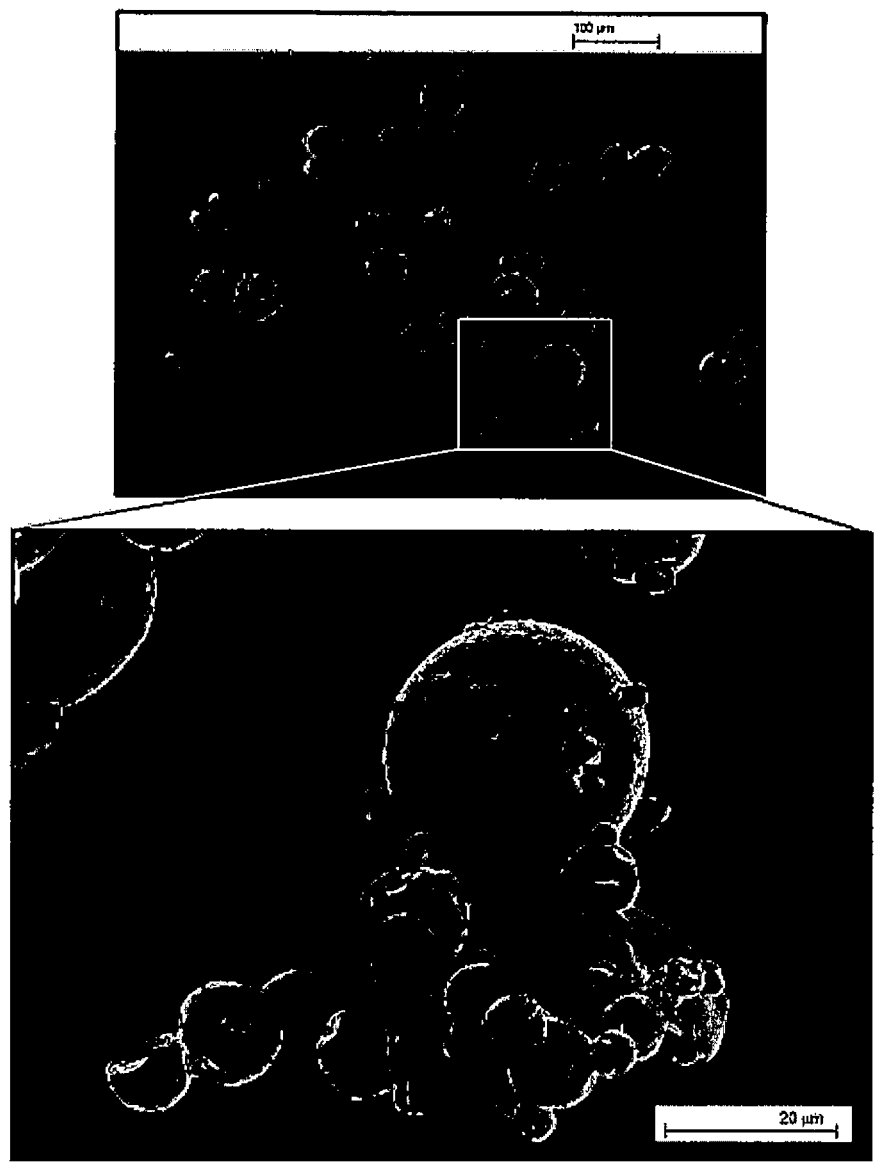
FIG. 32 is a scanning electron micrograph showing Braini® powder as an agglomerate of NeurXcel® powder, Peptylin® powder, and Wild blueberry powder. (Scale top: 100 um; bottom: 20 um).

Braini® powder is analyzed in FIG. 32. The powder is easily dispersed, in the form of discrete particles. As shown in FIG. 32, each particle is an agglomerate of two or three of the initial ingredients. The magnified image clearly shows all three materials in one particle. (Scale top: 100 um; bottom: 20 um).

Figure 33:
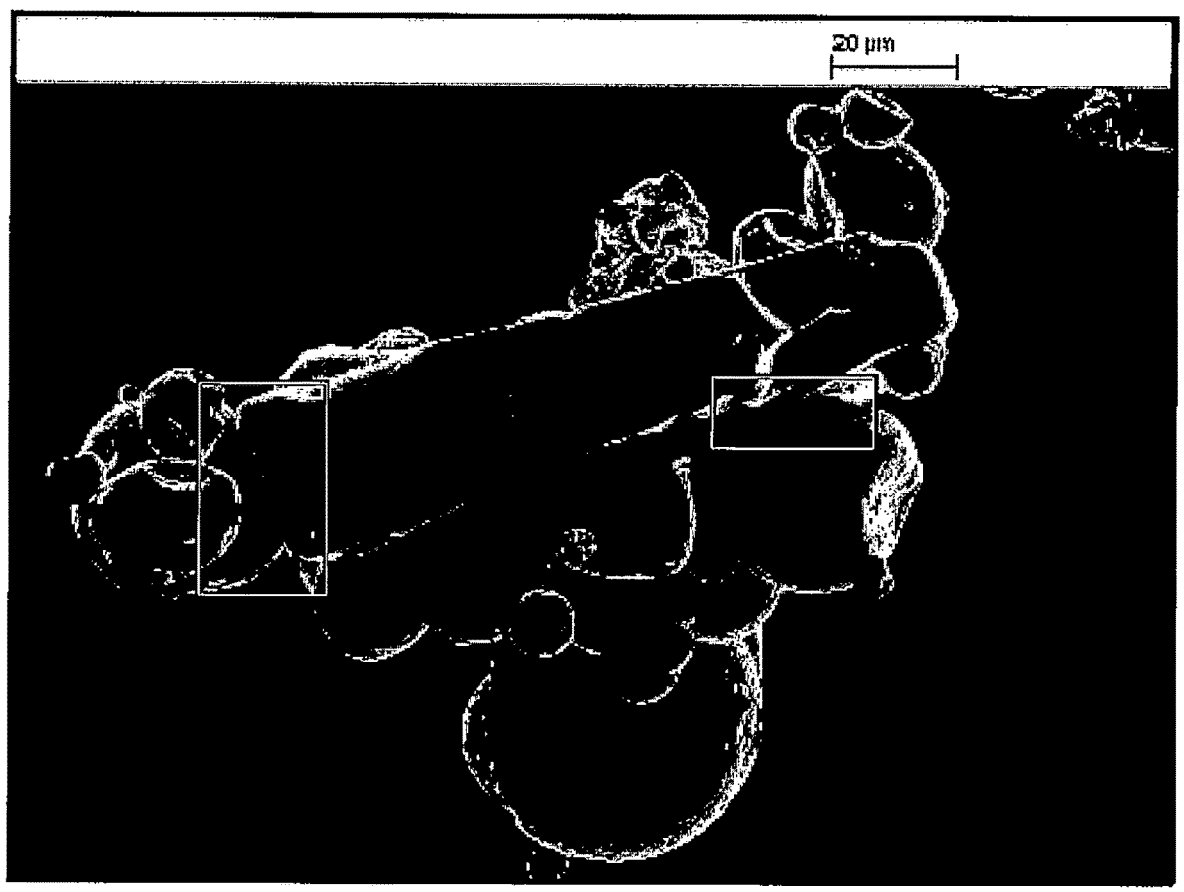
FIG. 33 is a scanning electron micrograph showing Braini® powder as an agglomerate of NeurXcel® powder, Peptylin® powder, and Wild blueberry powder. (Scale: 20 um).
Figure 34:
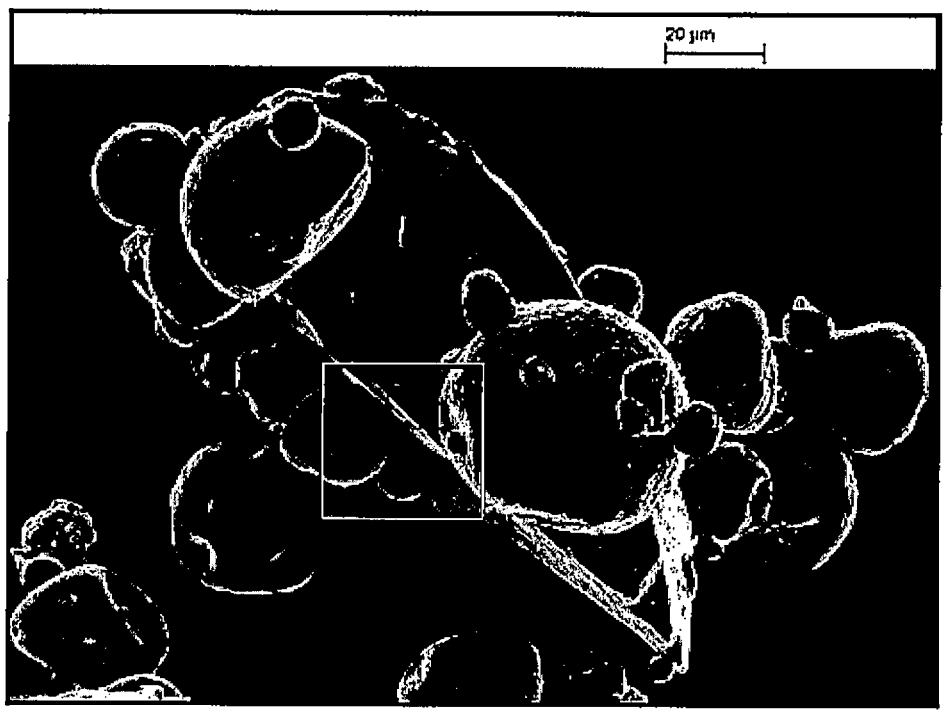
FIG. 34 is a scanning electron micrograph showing Braini® powder as an agglomerate of NeurXcel® powder, Peptylin® powder, and Wild blueberry powder. (Scale: 20 um).
Figure 35:
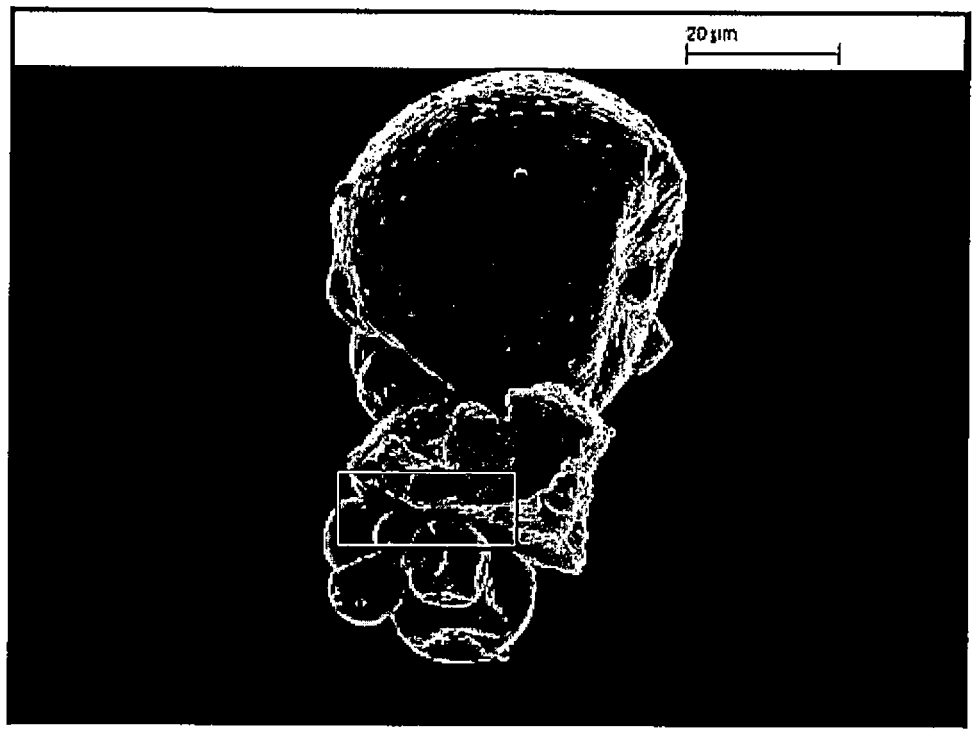
FIG. 35 is a scanning electron micrograph showing Braini® powder as an agglomerate of NeurXcel® powder, Peptylin® powder, and Wild blueberry powder. (Scale: 20 um).

FIGS. 33-35 further show Braini® powder in the form of particles made of agglomerates of Peptylin® powder, NeurXcel powder, and wild blueberry powder. Highlighted areas provide evidence of constituent ingredients merging and bonding together more than would be expected for particles merely held together by electrostatic attraction. (Scale: 20 um).

In addition, in several areas (highlighted in FIG. 35), evidence can be seen of a 'neck' of material between adjoining particles, adhering them together. This merging of particles is not seen in particles held together by electrostatic forces (where the particles would remain unchanged) and indicates interaction between the materials to form a new physical structure. (Scale: 20 um).

Figure 36:
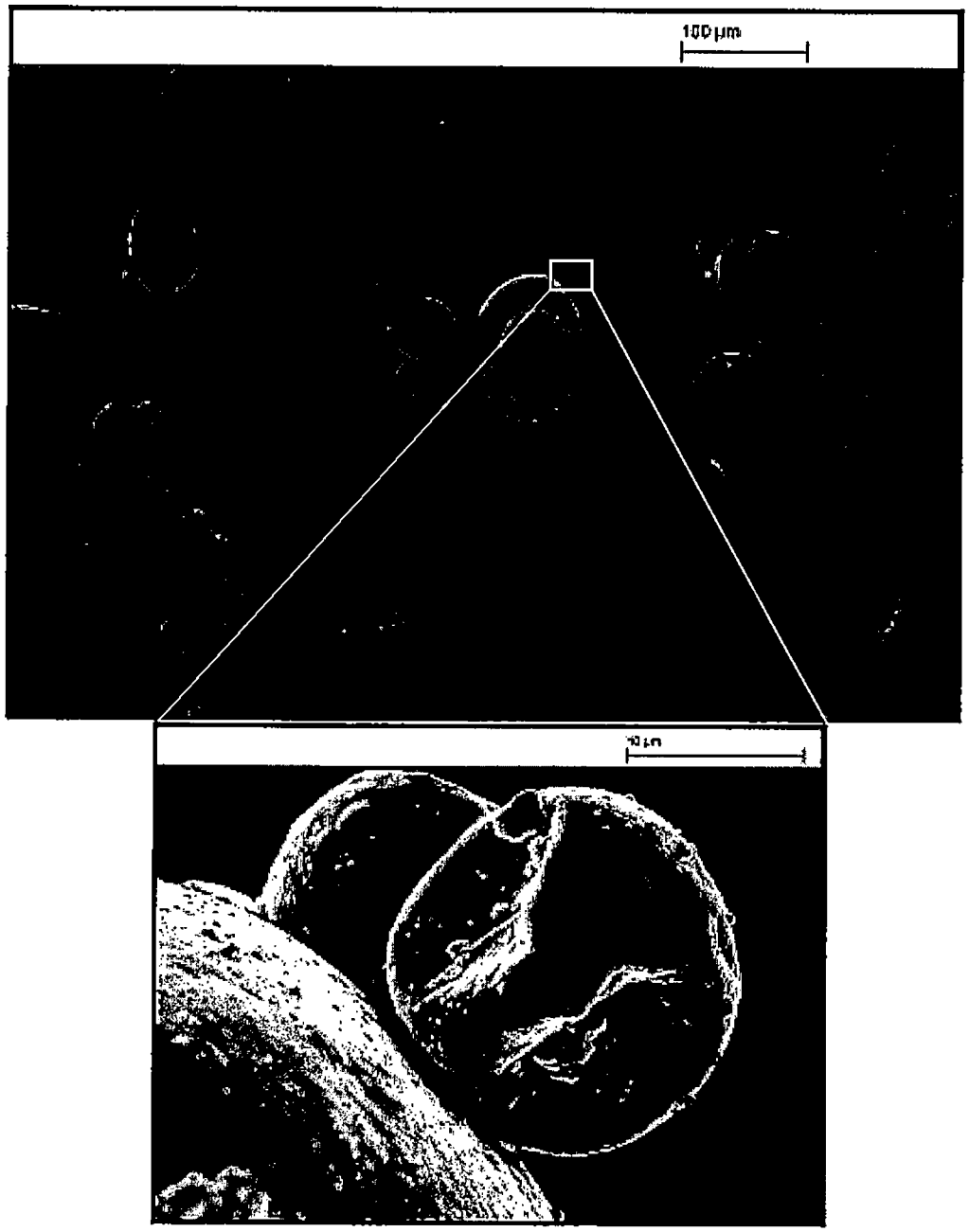
FIG. 36 is a scanning electron micrograph showing Braini Lex® powder as an agglomerate of NeurXcel® powder, Peptylin® powder, and Wild blueberry powder. (Scale top: 100 um, bottom: 10 um).

Braini Lex® powder was analyzed and found to have similar characteristics to the Braini® powder. As shown in FIG. 36, the Braini Lex® particles are agglomerations of the three ingredients (Peptylin® powder, NeurXcel powder, and wild blueberry powder), and there is evidence of merging of the ingredients in the formation of the particles. (Scale top: 100 um; bottom: 10 um).

Figure 37:
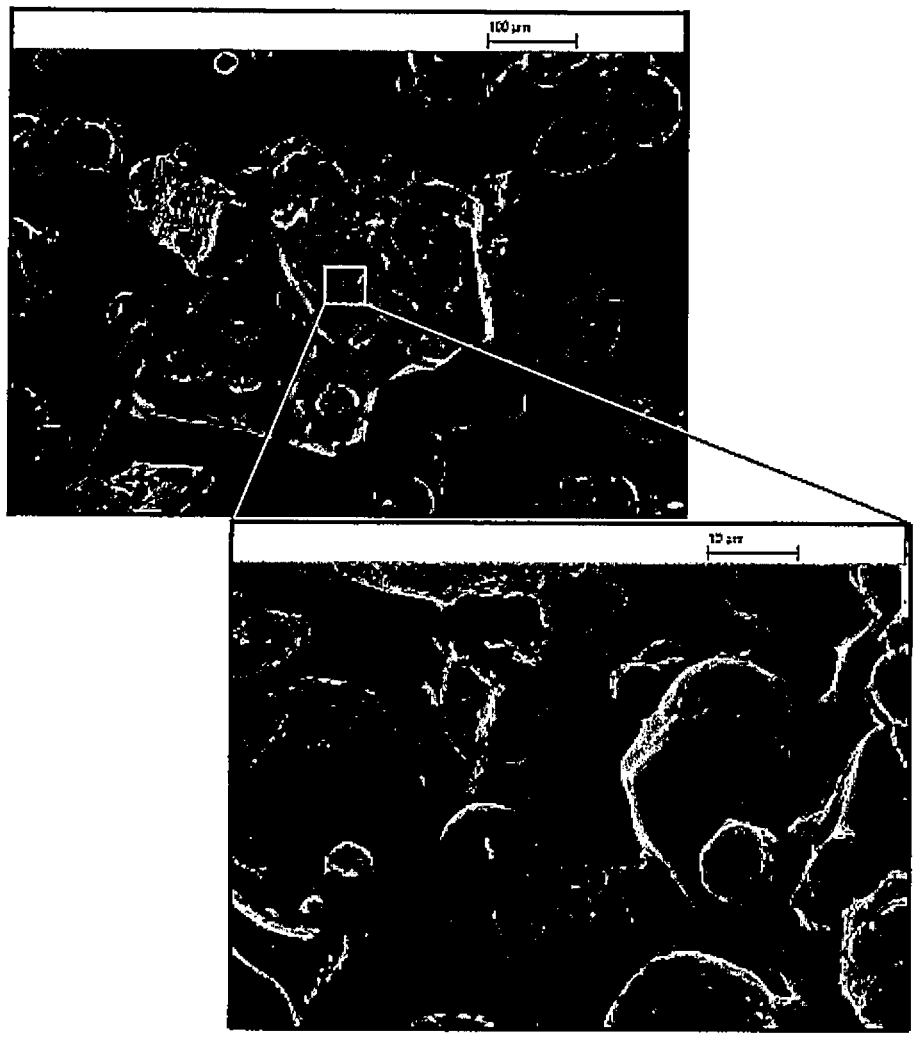
FIG. 37 is a scanning electron micrograph showing powder from Braini® capsules as an agglomerate of NeurXcel® powder, Peptylin® powder, and Wild blueberry powder. (Scale top: 100 um, bottom: 10 um).
Figure 38:
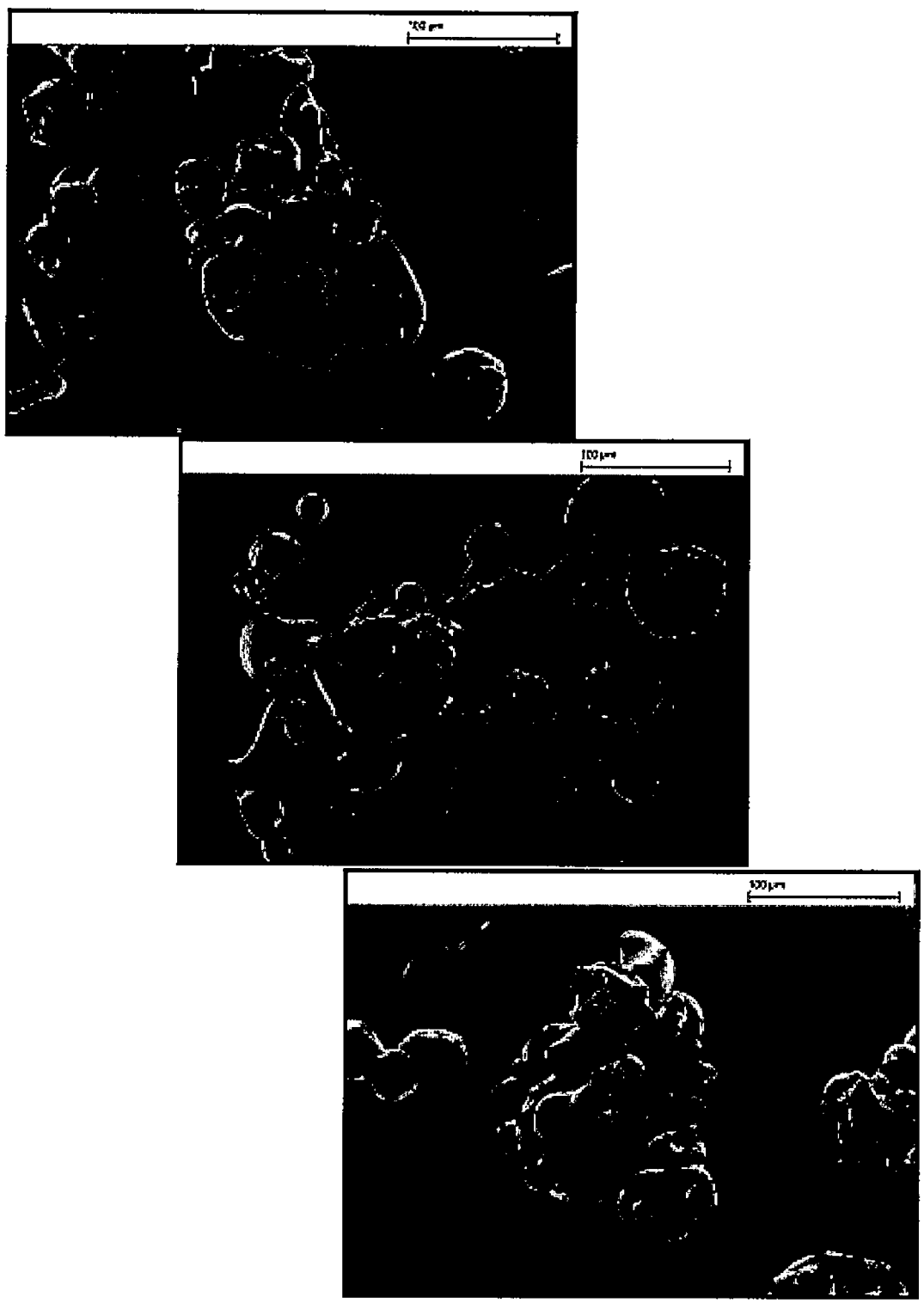
FIG. 38 is a scanning electron micrograph showing powder from Braini® capsules as an agglomerate of NeurXcel® powder, Peptylin® powder, and Wild blueberry powder. (Scale top, middle, bottom: 100 um).

FIG. 37 shows the encapsulated material from Braini® Capsules is, on the surface, different from the Braini® powder. The encapsulated material is composed of discrete particles, recognizably containing each of the ingredients. There is a very high degree of what appears to be a coating over the entire surface of the particles. This is possibly an excess of the material seen in small necks in the Braini® powder that was holding the particles together. The processing of the three ingredients has resulted in a clear change, showing that this is not a simple mixture of the three components. (Scale top: 100 um; bottom: 10 um). FIG. 38 also shows that the encapsulated material from Braini® Capsules includes a high degree of merging of the initial ingredients. (Scale top, middle, bottom: 100 um).

Figure 39:
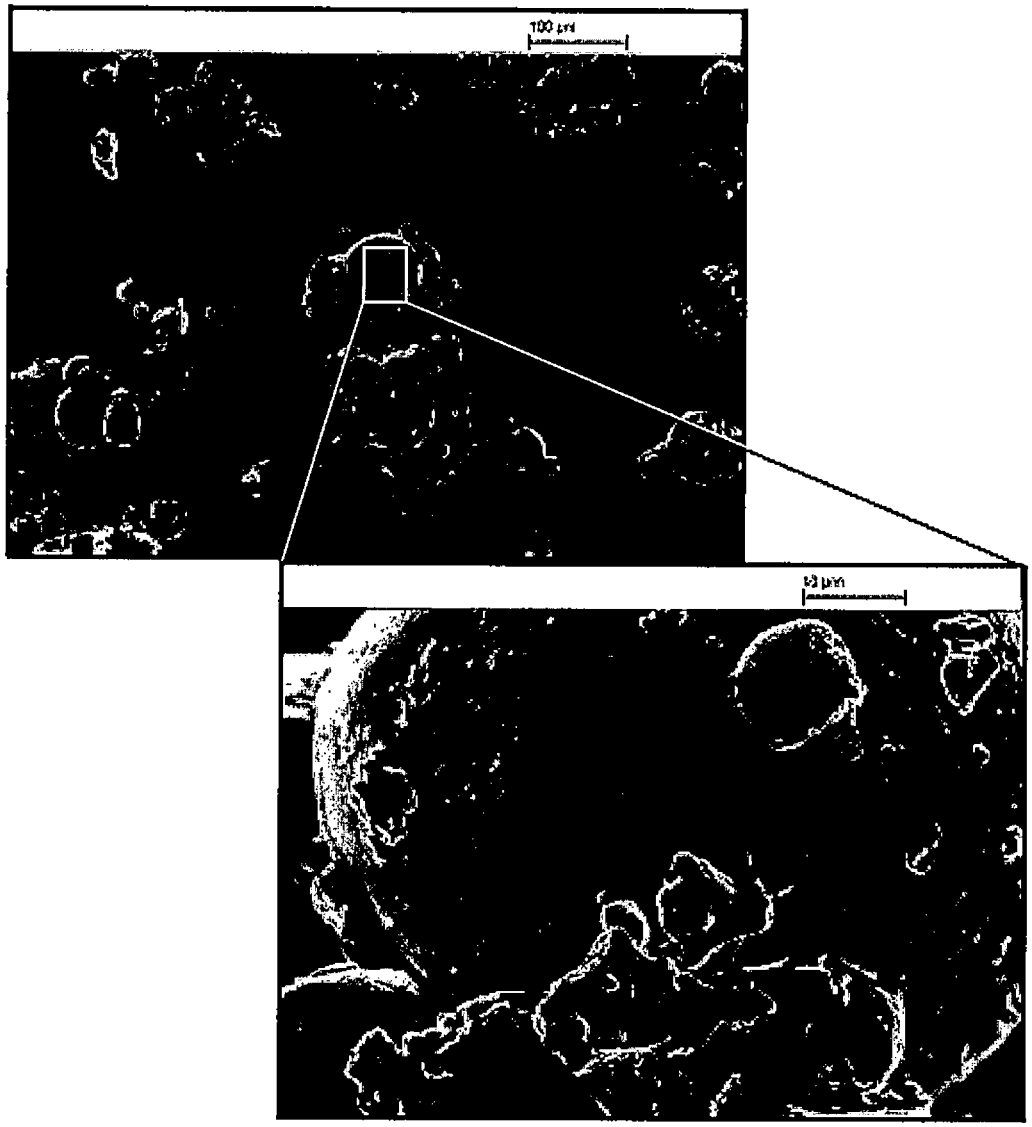
FIG. 39 is a scanning electron micrograph showing powder from Braini Lex® capsules as an agglomerate of NeurXcel® powder, Peptylin® powder, and Wild blueberry powder. (Scale top: 100 um, bottom: 10 um).

As shown in FIG. 39, the encapsulated material from Braini® Lex capsules also includes a high degree of merging of the initial ingredients, such that all three ingredients have merged together to form discrete particles. (Scale top: 100 um; bottom: 10 um).

Figure 40:
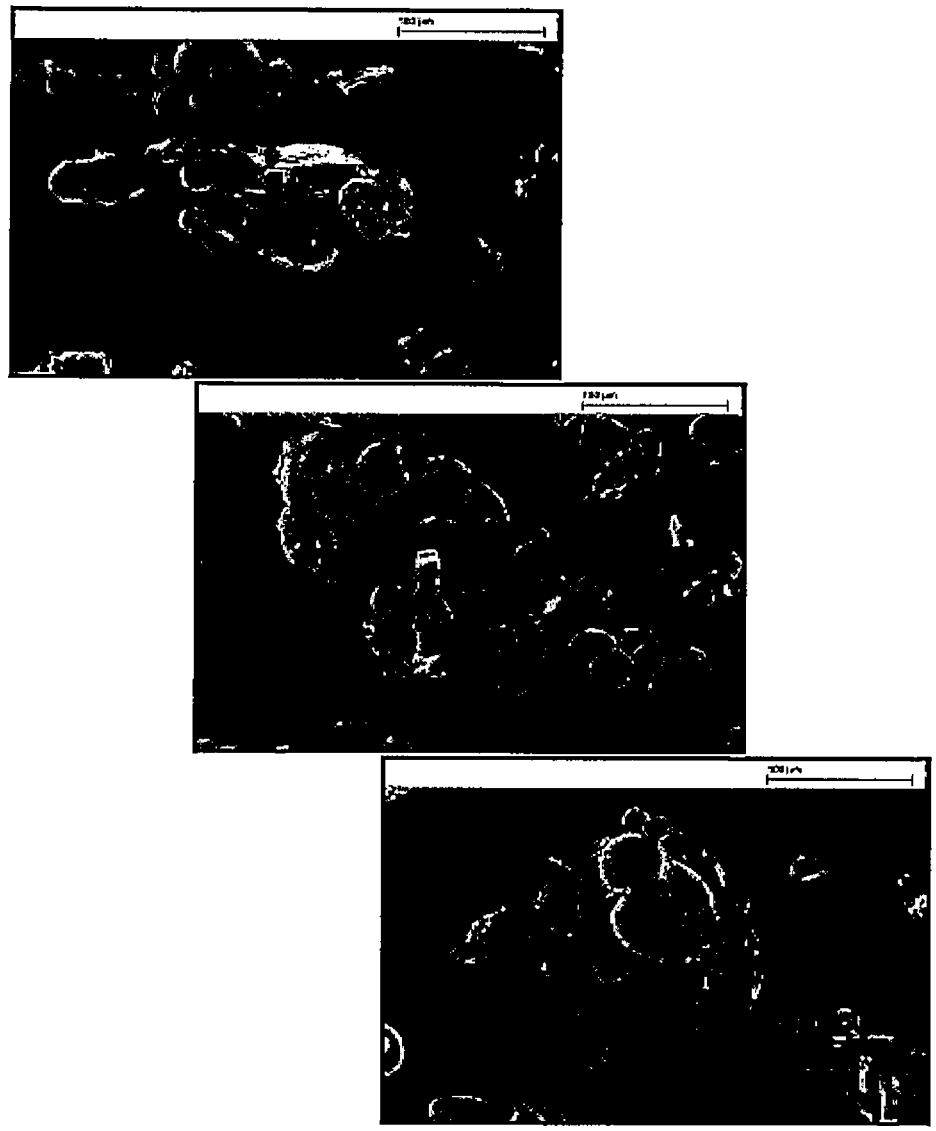
FIG. 40 is a scanning electron micrograph showing powder from Braini® capsules as an agglomerate of NeurXcel® powder, Peptylin® powder, and Wild blueberry powder. (Scale top, middle, bottom: 100 um).

Finally, FIG. 40 shows further images of the Braini Lex® capsule material, showing a high degree of merging of the Peptylin® powder, NeurXcel® powder, and wild blueberry powder. (Scale top, middle, bottom: 100 um).

Further evidence of merging and transformation of particles as seen under the Scanning Electron Microscope may be seen by the substantial amount of empty space around the particles throughout these photomicrographs. Also, without being bound by theory, it is noted that the encapsulated material tested was prepared in an earlier batch than the powder provided for this experiment, and so may have had additional time to agglomerate.

Example 23

HPLC Mass Spectrometry Analysis of Braini® Ingredients and Formulation

HPLC mass spectrometry was carried out on diluted ethanol extracts of Peptylin®, NeurXcel® (NeurXcel®) seed oil encapsulated powder, BLUEd'OR Wild Dried Blueberry powder (60 mesh), Braini® bulk powder, Braini R capsules, BrainiLex® bulk powder, and BrainiLex R capsules.

Figure 41:
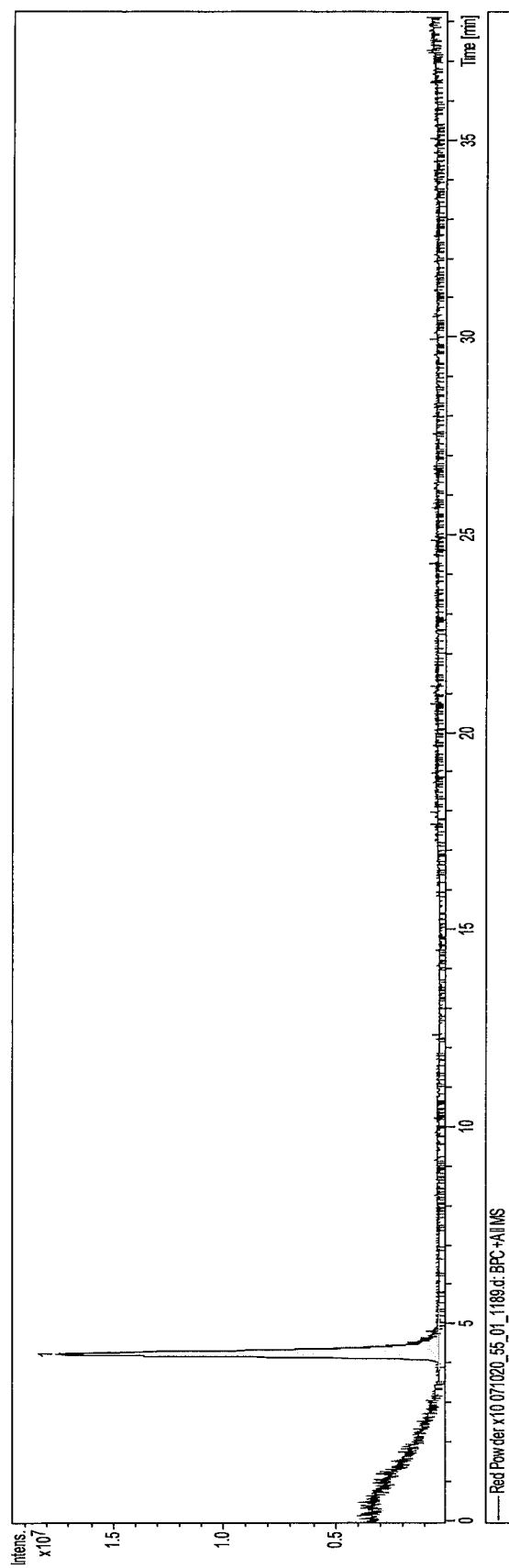
FIG. 41 show HPLC mass spectra of (top to bottom) Braini® capsule, Braini® powder, Peptylin® powder, NeurXcel® powder, Wild Blueberry Extract powder.
Figure 41:
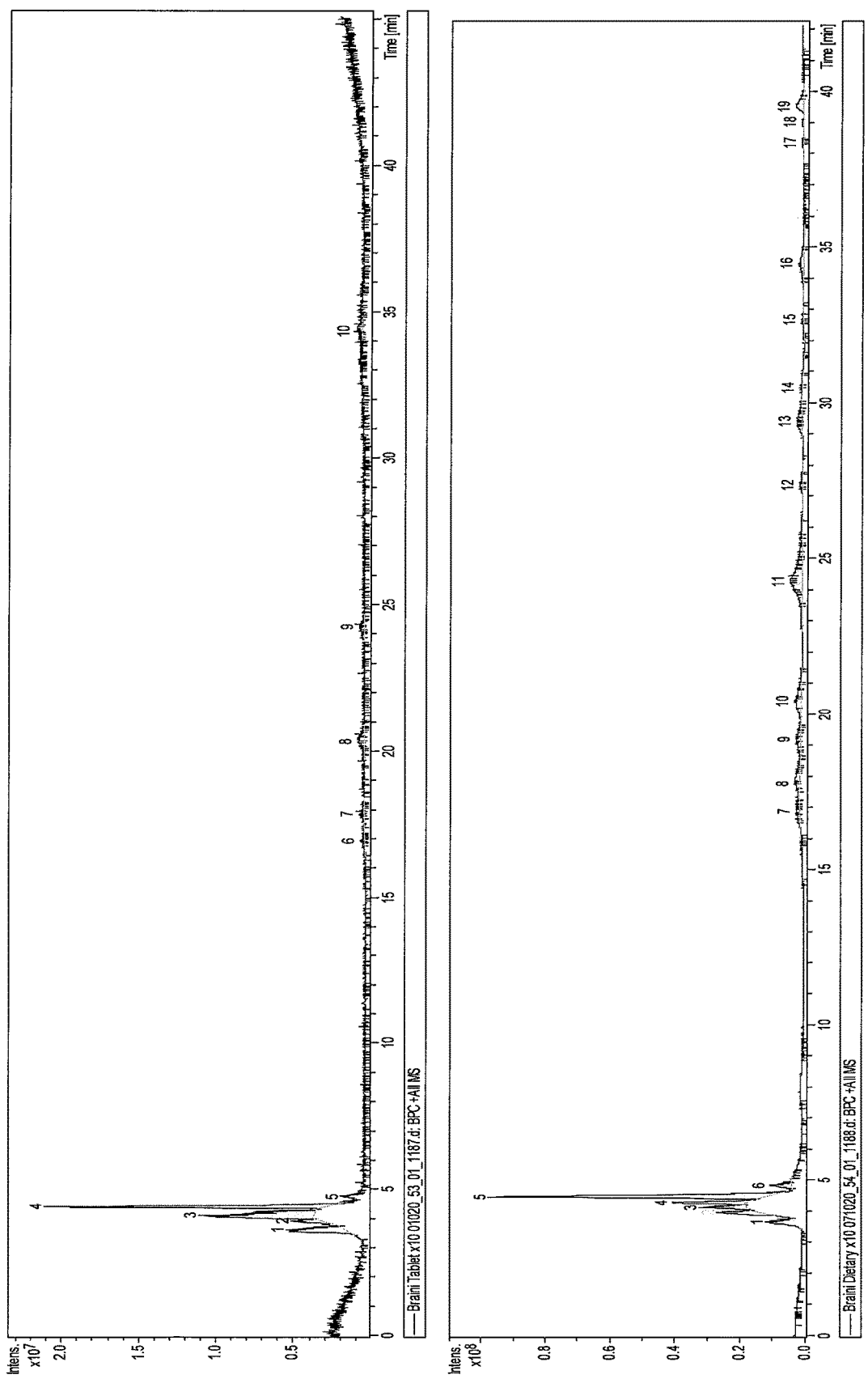
Figure 41:
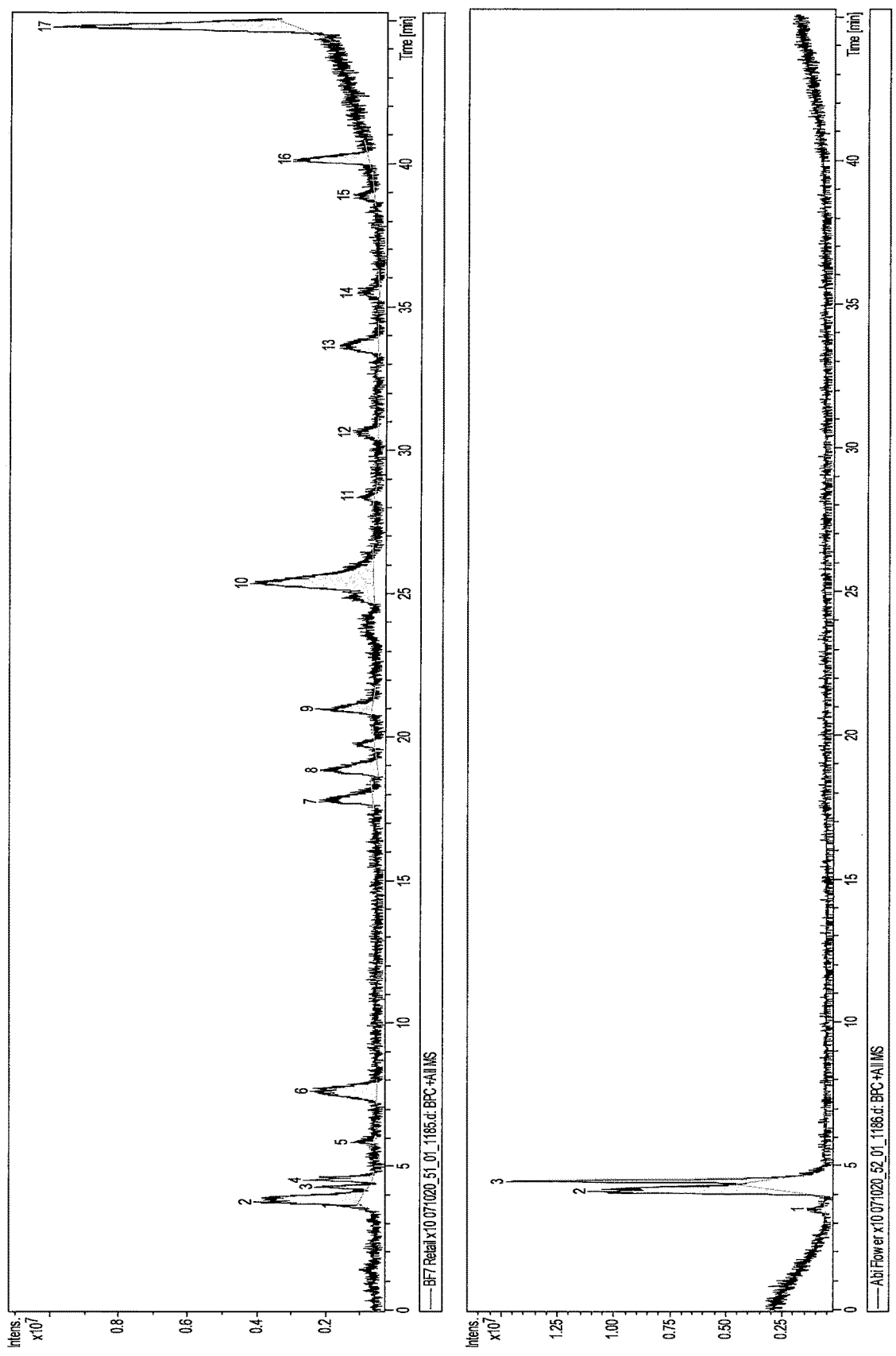

Some striking differences are evident between the Peptylin, NeurXcel, and Blueberry starting compounds and the Braini® and BrainiLex® products shown in FIG. 41. For instance, peak #17 in the Peptylin® spectra (middle) is the dominant peak in the starting material, but is completely absent in the products (either the powder or the capsules; top 2 spectra). Peak #16 in the Peptylin spectra is not present in the Braini® product spectra. Also, Peak #6 is not present in the Braini® product spectra.

In addition, Peak #10 in the Peptylin spectra appears to have shifted to a lower retention time (Peak #11) in the Braini dietary supplement spectra. Peak #10 in the Peptylin spectra is part of a group of 5 peaks. The retention times of Peaks #7 and #8 in the Peptylin spectra have not altered in the Braini dietary supplement spectra, but Peak #10 has shifted to a lower retention time (Peak #11) in the Braini product spectra. The disappearance of Peak #17 and Peak #16 from the Peptylin spectra in particular indicates that a component of the Peptylin starting material underwent a transformation including some form of molecular change when combined the other ingredients to form a Braini® product.

The present invention is directed to decreasing inflammation and/or oxidative stress, and providing neuroprotection, in a subject with compositions of this invention. Methods of this invention include the treatment and/or prevention of diseases and/or disorders by decreasing inflammation, decreasing oxidative stress, or providing neuroprotection, for instance where the inflammation and/or oxidative stress is caused by a sugar, such as a polysaccharide. The below Examples study cell viability, TNF-alpha, and IL-6 in cultured cells exposed to Peptylin®, NeurXcel®, and other substances. For the purposes of the present invention, NeurXcel® oil (eg. FFA) and NeurXcel® EE oil may be used interchangeably.

The Braini® active complex of the present invention, comprising Peptylin® +NeurXcel® and optionally Blueberry Extract, exhibits a statistically significant ($p<0.001$) anti-neuroinflammatory effect in microglial RAW264.7 cells vs. NeurXcel® alone (+7.8% better) and vs. Peptylin® alone (which by itself exhibited no such effect). See e.g. Examples 24 and 25.

For instance, Peptylin® alone may reduce the presence of interleukin-6 (IL-6), while NeurXcel® alone may have a higher effect in reducing the presence of IL-6 (in the range of 24%-55% as shown Example 25 below). In combination, Peptylin® and NeurXcel® together provide a greater effect on IL-6 reduction (in a range of 52-68% reduction as shown Example 25 below). Compare with Peptylin® alone or NeurXcel® alone at comparable concentrations.

In the same cell challenge model, the Braini® active complex of Peptylin® +NeurXcel® significantly and unexpectedly outperforms omega-3 DHA by as much as 38%. DHA is globally recognized as part of the standard of care for preventing or ameliorating the effects of age-related dementia and for treating traumatic brain injuries, concussions, and other pro-inflammatory insults to the brain.

Overall, the Braini formulation comprising Peptylin® and NeurXcel® has shown a significant anti-inflammatory response, which is inclusive of all physiologic systems, examples of which are inflammatory diseases, auto-immune diseases, cardiovascular diseases, many types of cancer, inflammatory neurological diseases, inflammatory gastrointestinal diseases, and other diseases or conditions in which inflammation is inherent. In an embodiment, a method of the present invention includes a method of treating and/or preventing an inflammatory disease, an auto-immune disease, a cardiovascular disease, and a type of cancer. In an embodiment, such inflammatory disease is an inflammatory neurological disease or an inflammatory gastrointestinal disease.

In an embodiment, the present invention is a method of treating or preventing inflammation and/or oxidative stress. In an embodiment, the present invention is a method of treating brain trauma, or brain injury, decreasing neuroinflammation, treating or preventing ALS (Amyotrophic Lateral Sclerosis), treating or preventing inflammatory diseases including systemic, infectious diseases, treating auto-immune diseases such as Multiple Sclerosis, treating or preventing an auto-immune disease; treating and/or preventing arthritis including rheumatoid arthritis, lupus, inflammatory bowel disease (IBD), Crohn's disease, Addison's disease, Grave's disease, myasthenia gravis, Hashimoto's disease, celiac disease, ulcerative colitis, gastritis; treating and/or preventing cardiovascular disease and/or aiding recovery from a cardiovascular incident, a stroke, calcification of the heart, myocardial infarction; treating a type of cancer or epilepsy; treating and/or preventing an inflammatory neurological disease; treating and/or preventing meningoencephalitis, inflammatory mechanisms in neural conditions (such as inflammatory mechanisms in Alzheimer's, Parkinson's, Huntington's disease, ALS, stroke, traumatic brain injury). See for instance Degan et al. (2018). Without being bound by theory, the present invention activates glial cells and complement-mediated pathways, synthesis of inflammation mediators, and/or recruits leukocytes.

In an embodiment, the present invention decreases inflammation in the body. In an embodiment, the present invention decreases oxidative stress in the body. In an embodiment, the present invention promotes neurogenesis in the body. In an embodiment, a method of the present invention treats and/or prevents, and/or decreases inflammation and oxidative stress, in leaky brain and related neurological and psychiatric disorders, and in major depressive disorder. See for instance Morris et al. (2018). In an embodiment, a method of the present invention may decrease inflammation and/or oxidative stress and thereby treat, prevent, or aid in treatment/prevention of Alzheimer's disease, chronic pain, neurodegenerative disorders, brain disease. See for instance Salter (2017) and Kwon et al. (2020).

In an embodiment, a method of treatment and/or prevention according to this invention comprises the steps of providing a composition having an effective amount of *Buglossoides arvensis* seed oil and purified *Bombyx mori* cocoon silk peptide fiber, and optionally blueberry extract, and administering an effective amount of the composition to a subject to treat and/or prevent as specified. In an embodiment, a method of decreasing inflammation and/or decreasing oxidative stress according to this invention comprises the steps of providing a composition having an effective amount of *Buglossoides arvensis* seed oil and purified *Bombyx mori* cocoon silk peptide fiber, and optionally blueberry extract, and administering an effective amount of the composition to a subject to treat and/or prevent as specified. In an embodiment, an "effective amount" is as defined throughout this application, and in particular with regard to a method of treating and/or preventing a disease, condition, or disorder, or decreasing inflammation and/or oxidative stress, a mass balance ratio of oil:peptide fiber of about 0.15-0.5:1, for instance about 0.18-about 0.43:1, and about 0.25-0.35:1, and about 0.3:1. In an embodiment, a daily dose of amounts of refined *B. arvensis* oil and *B. mori* peptide fiber according to this invention include ranges of amounts as defined throughout this application and in keeping with the above ratios. In an embodiment, an effective amount according to this invention includes as a composition and/or a daily dose a combination of about 100-5500 mg Peptylin® (for instance 1093-5464 mg or 100-1000 mg or 200-1000 mg or 400-600 mg) and of about 25-3000 mg NeurXcel® (for instance about 25-750 mg or 250-750 mg or 25-3000 mg, 50-1000 mg, 100-800 mg, 200-750 mg, 250-750 mg, 25-400 mg). Timeframes for administration of the present compositions in a method of the present invention include those described throughout this application, and for instance 1 day, 2-6 days, 1 week, 2 weeks, 1 day-1 month, 1 month-2months or more, and so on.

In an embodiment, the present invention includes a method of a sequential treatment or administration with refined *Buglossoides arvensis* oil (NeurXcel®) of the present invention. Said method includes the steps of providing a composition comprising an effective amount of refined *Buglossoides arvensis* seed oil (e.g. NeurXcel®) as defined above, and then administering the composition to a subject already taking a daily or regular dose of Peptylin®. In an embodiment, such a composition, and/or a daily dose of said refined *Buglossoides arvensis* seed oil, is up to 3000 mg, including for instance 25-3000 mg, 50-1000 mg, 100-800 mg, 200-750 mg, 250-750 mg, 25-400 mg, or other amount appropriate to the subject. In an embodiment, the subject is human.

The present invention uses the synergistic effects of different natural-based products (silk fibroin peptide (Peptylin®), NeurXcel® (including plant-based omega), and optionally blueberry extract) to promote health in all aspects of the nervous system—central, peripheral, and autonomic—to decrease inflammation, decrease oxidative stress, and promote neurogenesis. Compositions and methods of the present invention may protect against oxidative stress. These activities, collectively, both promote health and help to decrease the burden of inflammatory conditions in the nervous system, including but not limited to cognitive decline, multiple sclerosis, Parkinson's Disease, Alzheimer's disease, dementia, cognitive decline, a seizure disorder, depression, and anxiety. In an embodiment, the method of the present invention may treat Alzheimer's disease, dementia, cognitive decline, and other conditions arising from elevated blood sugars (see e.g. the below Examples and anti-inflammatory responses from elevated saccharide LPS (lipopolysaccharide).

Generally, no effect on cell viability in WST-8 assays was found after exposure of the cells for instance to EPA EE (eicosapentaenoic acid, ethyl ester), Peptylin®, Peptylin® in combination with NeurXcel®, Peptylin in combination with EPA EE, NeurXcel® Oil EE, or NeurXcel Oil FFA (as defined in above). In one study, Peptylin® alone was found to increase cell viability by 10-25%.

In cell cultures challenged with LPS to stimulate TNF-alpha production, compared with lipopolysaccharide (LPS) controls, EPA EE alone was found to reduce TNF-alpha production in BV-2 cells by 25% in one study, 18% in another study, and 27-33% in a third study. In RAW264.7 cells, EPA EE reduced TNF-alpha production by 32%. By comparison, Peptylin® reduced TNF-alpha production by 31-39% in BV-2 cells. Lower concentrations of 50 ug/ml negated Peptylin®'s pro-inflammatory effect. Peptylin® combined with EPA EE reduced TNF-alpha production by 35-42% in BV-2 cells. Peptylin® in combination with NeurXcel® in one study achieved a 30-56% reduction in TNF-alpha production in RAW264.7 cells. NeurXcel® Oil EE alone reduced TNF-alpha production in RAW264.7 cells by 31-58%, and then again, by 37-52%. NeurXcel Oil EE was not cytoxic at lower concentrations, but became cytotoxic at higher concentrations (>300 ug/ml). NeurXcel Oil FFA did not affect TNF-alpha production in some preliminary studies.

Summary of Studies on Peptylin® and NeurXcel® on LPS-Induced TNF-Alpha Production in BV-2 and RAW264.7 Cells In cell viability studies where EPA EE had no effect, Peptylin® alone increased cell viability by 10-25%. NeurXcel® Oil EE and NeurXcel Oil FFA (considered physiologically equivalent for the purposes of this invention as discussed above) also had no effect on cell viability. Where a 25% reduction in LPS-induced TNF-a production was seen by EPA EE exposure to BV-2 cells, a 31-39% reduction in TNF-a production was found with Peptylin® alone, and a 35-42% reduction in TNF-a production found with Peptylin®+EPA EE. NeurXcel Oil alone (EE or FFA) and Peptylin+NeurXcel had no effect on LPS-induced TNF-a production in BV-2 cells. NeurXcel® Oil EE reduced viability of RAW264.7 cells by 14-19%. Also in that study, NeurXcel® Oil EE reduced LPS-induced TNF-a production by 31-58%, compared with reductions of 21-42% (DHA EE), 32% (EPA EE), and 35-71% (toxic amount of SDA EE) (see above discussion of omega-3 and omega-6 studies).

In a study using RAW264.7 cells, where Peptylin®, Peptylin® +NeurXcel®, and NeurXcel Oil EE had no effect on cell viability, the effect of Peptylin® alone caused an increase of 3-71% in LPS-induced TNF-a production, causing an antagonist effect. Peptylin® at a 50 ug/ml exposure increased TNF-a production by 3%; 100 ug/ml increased TNF-a production by 38%; 150 ug Peptylin®/ml increased TNF-a production by 41%; and 200 ug Peptylin®/ml increased TNF-a production by 71%. In contrast, NeurXcel Oil EE reduced TNF-a production by 35-45% (35% with a 30 uM concentration of NeurXcel® and 45% with a concentration of 50 uM NeurXcel®). Taken together, 50 ug/ml Peptylin®+50 uM NeurXcel® increased TNF-a production by 10%; 100 ug/ml Peptylin®+50 uM NeurXcel® increased TNF-a production by 17%; 150 ug/ml Peptylin®+50 uM NeurXcel® increased TNF-a production by 13%; and 200 ug/ml Peptylin®+50 uM NeurXcel® increased TNF-a production by 21%.

In a study challenging RAW264.7 cells in 3 batches (discussed above), where SDA EE reduced LPS-induced TNF-a production by 16-24% and DGLA EE reduced TNF-a production by 11-18%, NeurXcel® Oil EE reduced TNF-a production by 55-79%. In another study, Peptylin®, Peptylin®+NeurXcel®, and NeurXcel® Oil EE had no effect on RAW264.7 cell viability. 50 ug/ml Peptylin® did not increase or decrease LPS-induced TNF-a production, however, in combination with 50 uM NeurXcel®, Peptylin® and NeurXcel® reduced TNF-a production by 30%; and 50 ug/ml Peptylin® and 100 uM NeurXcel® reduced TNF-a production by 56%. Taken alone, NeurXcel® 50 uM reduced TNF-a production by 37% and 100 uM NeurXcel® reduced TNF-a production by 52%. Overall, Peptylin®+ NeurXcel® taken together reduced LPS-induced TNF-a production by a statistically significant 30-56%, whereas Peptylin® alone had no effect on TNF-a production, and NeurXcel® Oil EE (50,100 uM) reduced TNF-a production by 37-52%. In a further study, Peptylin®+NeurXcel® did not diminish RAW264.7 cell viability. Peptylin® (60 ug/ml) alone did not affect LPS-induced TNF-a production, however, Peptylin® (60 ug/ml) in combination with 50 uM and 100 uM NeurXcel® reduced TNF-a production by 44 and 57% respectively. Taken alone, NeurXcel® reduced TNF-a production 39 and 54% respectively. Overall, Peptylin®+ NeurXcel® reduced TNF-a production 44-57%, whereas Peptylin® alone had no effect and NeurXcel® alone reduced TNF-a production by 39-54%.

In a further study, Peptylin® and Peptylin®+NeurXcel® did not diminish RAW264.7 cell viability, but where Peptylin® had no effect on LPS-induced TNF-a production and NeurXcel® reduced TNF-a production by 42-50%, Peptylin®+NeurXcel® reduced TNF-a by statistically significant 49-58% (p<0.001). Peptylin® was used in an amount of 60 ug/ml in this study; NeurXcel® was used at 50 uM and 100 uM (43% and 50% reduction in TNF-a, respectively), and Peptylin® (60 ug/ml)+NeurXcel® (50 uM and 100 uM) reduced TNF-a by 49% and 58%, respectively.

It is noted that lower concentrations of Peptylin®, such as 50 ug-60 ug/ml, negate pro-inflammatory effects, and that optimal TNF-a suppression occurs at 60 ug/ml Peptylin®+ 100 uM NeurXcel®. Suppression of TNF-a production is improved by 7-8% with Peptylin®+NeurXcel®, compared with NeurXcel® alone (p<0.001). Peptylin®+NeurXcel® provide a synergistic effect on TNF-a production. NeurXcel® is not cytotoxic at lower concentrations, but is cytotoxic at higher concentrations (>300 ug/ml). Optimal TNF-a suppression with NeurXcer+Peptylin® or NeurXcel® alone is at 100 ug/ml NeurXcel®.

In an additional study, LPS-induced production of IL-6 was measured in RAW264.7 cells. Exposure of Peptylin® alone to the LPS-treated cells resulted in a decrease in IL-6 production of 17.20%. NeurXcel® at 30 uM, 50 uM, and 70 uM concentrations reduced LPS-induced IL-6 production by 24.16%, 36.11%, and 54.57%, respectively. NeurXcel® (30 uM, 50 uM, 70 uM)+Peptylin® (50 ug/ml) reduced LPS-induced IL-6 production by 51.67%, 67.69%, and 66.69%, respectively.

Overall, Peptylin® alone reduced the presence of IL-6 by a relatively small amount (about 17%) compared with the upper range achieve by NeurXcel® alone (24-55%). However, Peptylin® +NeurXcel® combined provided a greater effect on IL-6 reduction (52-68%). The combined reduction of IL-6 Peptylin®+NeurXcel® was overall greater than Peptylin® alone and NeurXcel® alone, and the reduction of IL-6 by NeurXcel® alone was greater than by Peptylin® alone.

Example 24

Effect of Peptylin® and NeurXcel® on LPS-induced Microglial Activation in RAW264.7 Cells 1. Executive Summary
1.1 Aim The aim of the present study is to assay the effect of NeurXcel® and Peptylin®, used in combination or alone, in the LPS-induced TNF-a production in the mouse macrophage RAW264.7 cell line.

1.2 Methods

RAW264.7 cells were seeded in 96 well plates at a density of 20,000 cells/well. On day 2, the cells were serum starved for 24 h in DMEM. Then, the cells were pre-treated with 60 µg/ml of Peptylin® alone or in combination with 50 µM or 100 µM NeurXcel® EE diluted in DMEM. Appropriate vehicle controls have been included, i.e. 0.5% EtOH+1.2% $H_2O$. On day 4 the cells were LPS-induced (500 ng/ml) for 1.5 h and the supernatants were collected. A WST-8 assay was performed to measure cell viability and the supernatants were used for an ELISA assay to measure TNF-a levels. All the experiments were carried out with 9 replicates (for control and LPS treated cells) or 24 replicates (for cells treated with NX and/or PT). A t-test was used to compare the media of TNF-α levels between the treatment of NX alone and in combination with PT.

1.3 Results

According to the WST-8 assay none of the treatments affected cell viability. The PT alone did not reduce TNF-α levels. The treatment with 50 µM NX induced a reduction of 42% in TNF-α and the cotreatment with PT further reduced these levels 49%. The TNF-α was reduced 50% when cells were treated with 100 µM NX while the co-treatment with PT induced a reduction of 58%. In both cases there was a significant difference between treating the cells with NX alone or in combination with PT (p<0.001).

1.4 Conclusion

The NeurXcel® reduces the TNF-a levels in RAW264.7 cells induced with LPS. The co-treatment of cells with Peptylin® significantly improves the protective effect of NeurXcel®.

1. Introduction

Microglia are the primary antigen-presenting cells in the central nervous system. These immune-like cells can be activated in response to injury, disease, or inflammation, leading to the secretion of a variety of factors such as proinflammatory cytokines, prostaglandins, and reactive oxygen/nitrogen species, each of which can cause neuronal damage. LPS triggers an array of microglial response by interacting with the membrane receptor Toll-like receptor 4 (TLR4), leading to the production of proinflammatory mediates (e.g., cytokines and interleukins, TNFα, and IFNγ) and the self-activation of the nuclear factor NF-κB system. In this assay, the effect of Peptylin® and NeurXcel®, alone or in combination, in the production of TNFα was measured in LPS-induced RAW264.7 cells.

3. Materials and Methods
3.1 Reagents and Equipment
3.1 Reagents and Equipment

TABLE 26

Reagents and Equipment

| Reagent/Equipment and Catalogue and Lot Numbers | Supplier |
| --- | --- |
| RAW264.7 (# Cat. ATCC TIB-71) | ATCC |
| Dulbecco's Modified Eagle's Medium-high glucose-(# Cat. D6429) | Sigma-Aldrich |
| FBS (# Cat. F7524) | Sigma-Aldrich |
| Penicillin/Streptomycin (# Cat. 15240) | Gibco |
| Trypsin-EDTA 0.5% (w/v) (# Cat. 25300) | Gibco |
| PBS (# Cat. D8537) | Sigma-Aldrich |
| Cell counting Kit-8, WST-8 (# Cat. 96992 ) | Sigma-Aldrich |
| 3-(4,5-Dimethyl-2-thiazolyl)-2,5-diphenyl-2H-tetrazolium bromide (# Cat. 111714) | Millipore |
| Mouse TNF-alpha DuoSet ELISA (# Cat. DY410) | R&D Systems |
| DuoSet ELISA Ancillary Reagent Kit 2 (# Cat. DY008) | R&D Systems |
| Lipopolysaccharide, LPS (# Cat. L4391) | Sigma-Aldrich |
| Laminar flow cabinet (# ESCO class II BSC) | Lab Culture |

TABLE 26-continued

Reagents and Equipment

| Reagent/Equipment and Catalogue and Lot Numbers | Supplier |
| --- | --- |
| Incubator (# Model 381 S/N 314342) | Thermo Scientific |
| Synergy II microplate reader | BioTek Instruments |

3.2 Test Compounds

TABLE 27

Test Compound: Peptylin ®

| | |
| --- | --- |
| Test Item | Peptylin ® (powdered), a Purified *Bombyx mori* Cocoon Silk Peptide Fiber of this invention |
| Manufacturer | Famenity Co., Uiwang-si, S. Korea |
| Storage Conditions | The compound was protected from light and stored at room temperature. After reconstitution of the powder, samples were kept at 4° C. |
| Dilution protocol | Peptylin ® powder was dissolved in water to a concentration of 5 mg/ml. From this stock, the final 60 μg/ml concentration was prepared in DMEM (final $H_2O$ concentration of 1.2%). |

TABLE 28

Test Compound NeurXcel ® EE

| | |
| --- | --- |
| Test Item | NeurXcel ®, ethyl ester (NeurXcel ® EE), a Refined *Buglossoides arvensis* Seed Oil of this invention |
| Manufacturer | Nature's Crops International Ltd., Kensington, PE, Canada |
| Storage Conditions | The compound was protected from light and stored at −20° C. |
| Molecular Weight | 305 |
| Dilution protocol | NeurXcel ® EE oil was provided as a 100% active compound. First, 20 mM and 10 mM dilutions were prepared in 100% ethanol, from which the 100 and 50 uM working concentrations were prepared in DMEM medium (final ethanol concentration of 0.5%). |

3.3 Cell Culture

The mouse RAW264.7 cells were cultured in DMEM medium supplemented with 10% FBS in T75 flasks for 3 days. Cultures were maintained at 37° C. in a humidified atmosphere with 5% CO2.

3.4 Experimental procedure RAW264.7 cells were seeded in 96-well plates at a density of 20,000 cells/well in DMEM+10% FBS. The next day, the cells were washed once with DPBS and serum starved for 24 h in 150 μL of DMEM. Then, the cells were treated with 150 μL of 60 μg/ml of Peptylin® and 100 or 50 μM NeurXcel® EE that were used either alone or in combination. Appropriate vehicle controls were also included in the assay, i.e. 0.5% ethanol +1.2% H2O. After 24h, the cells were incubated for 1.5h with 10 μL of LPS (7500 ng/ml) to reach a final concentration of 500 ng/ml. After the incubation, the supernatants were collected and a WST-8 assay was carried out. CCK-8 reagent (WST-8) was diluted 1:10 in DMEM media and 100 μL were added to each well and the plate was incubated at 37° C. After 15 minutes the absorbance was measured at 450 nm using the Synergy II microplate reader. WST-8 is bioreduced by cellular dehydrogenases to an orange formazan product that is soluble in tissue culture medium. The amount of formazan produced is directly proportional to the number of living cells. The ELISA assay was performed following the manufacturer's instructions. The TNF-α levels produced under each condition were normalized to the corresponding vehicle control (with or without EtOH). All the experiments were carried out with 9 replicates (for control and LPS treated cells) or 24 replicates (for cells treated with NX and/or PT). To determine if the levels of TNF-α between the treatment of NX alone and in combination with PT were significantly different, a t-test was carried out. Using Microsoft Excel the following formula was used to calculate the p-value: =T.TEST(array1, array2,tails,type), where array1 corresponds to the TNF-α values for one treatment, array2 corresponds to TNF-α values for the co-treatment, one-tail test has been considered and type is 2 (two sample equal variance t-test). A p-value of 0.05 was used as the cutoff for significance.

4 Results 4.1 Cell Viability

Figure 42:
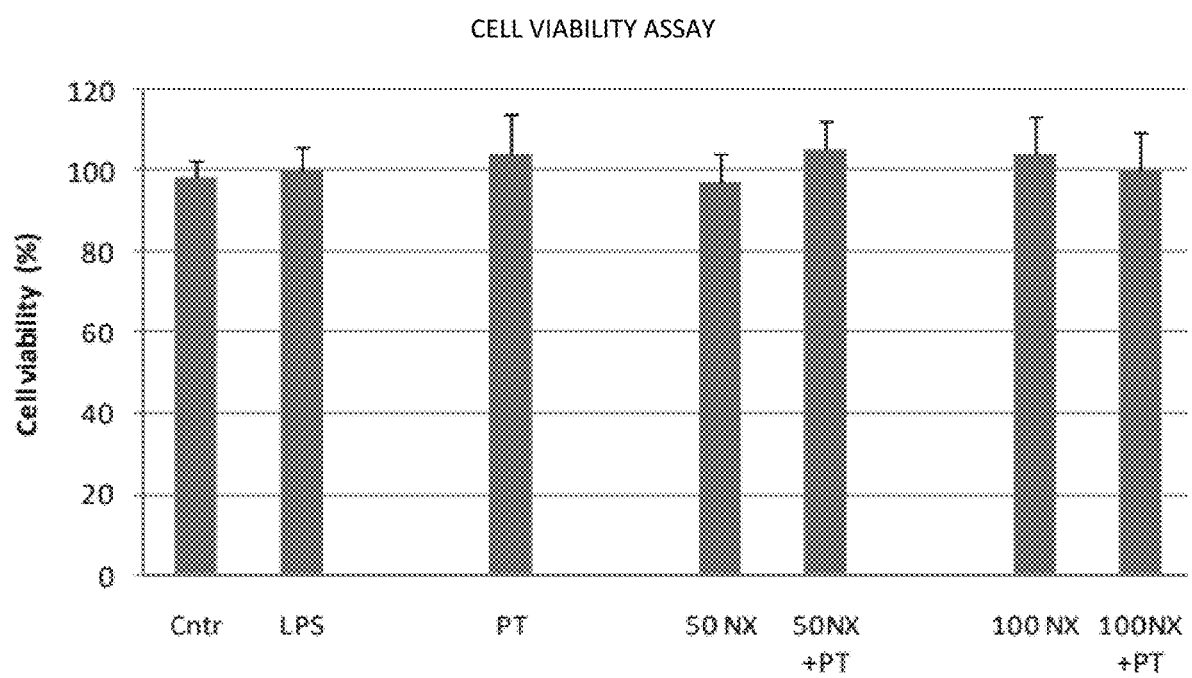
FIG. 42 is a graph showing WST-8 cell viability assay results after exposure of RAW264.7 cells to Peptylin® and NeurXcel®.

RAW264.7 cells were serum starved for 24 hours, pre-treated for 24 h with 60 μg/ml of Peptylin® and 100 or 50 μM NeurXcel®, alone or in combination. Then, the cells were induced for 1.5 h with 500 ng/ml LPS. After the treatments, the supernatants were collected and the cells were incubated with the CCK-8 reagent for 15 minutes. The absorbance was measured at 450 nm using the Synergy II microplate reader (FIG. 42).

Cell viability was determined by WST-8 analyzing the amount of formazan product produced by the cells, which is proportional to the number of living cells. Control: cells maintained in DMEM; LPS: LPS-induced cells in DMEM+ 0.5% EtOH+1.2% H2O; PT: cells pre-treated with 60 μg/ml of Peptylin® for 24 h; 50 NX and 100 NX: cells treated with 50 or 100 μM NX for 24 h; 50NX+PT and 100NX+PT: cells pre-treated with 50 or 100 μM NX and 60 μg/ml PT for 24 h. Then the cells were induced with 500 ng/ml LPS for 1.5 h. The data has been normalized to the corresponding LPS control which is considered to be 100% viability. The data represent the mean±SD of an experiment performed in nine replicates (for Cntr and LPS) or 24 replicates (for PT and NX treatments).

According to the WST-8 assay, none of the treatments affected cell viability.

4.2 TNF-α Production

Figure 43:
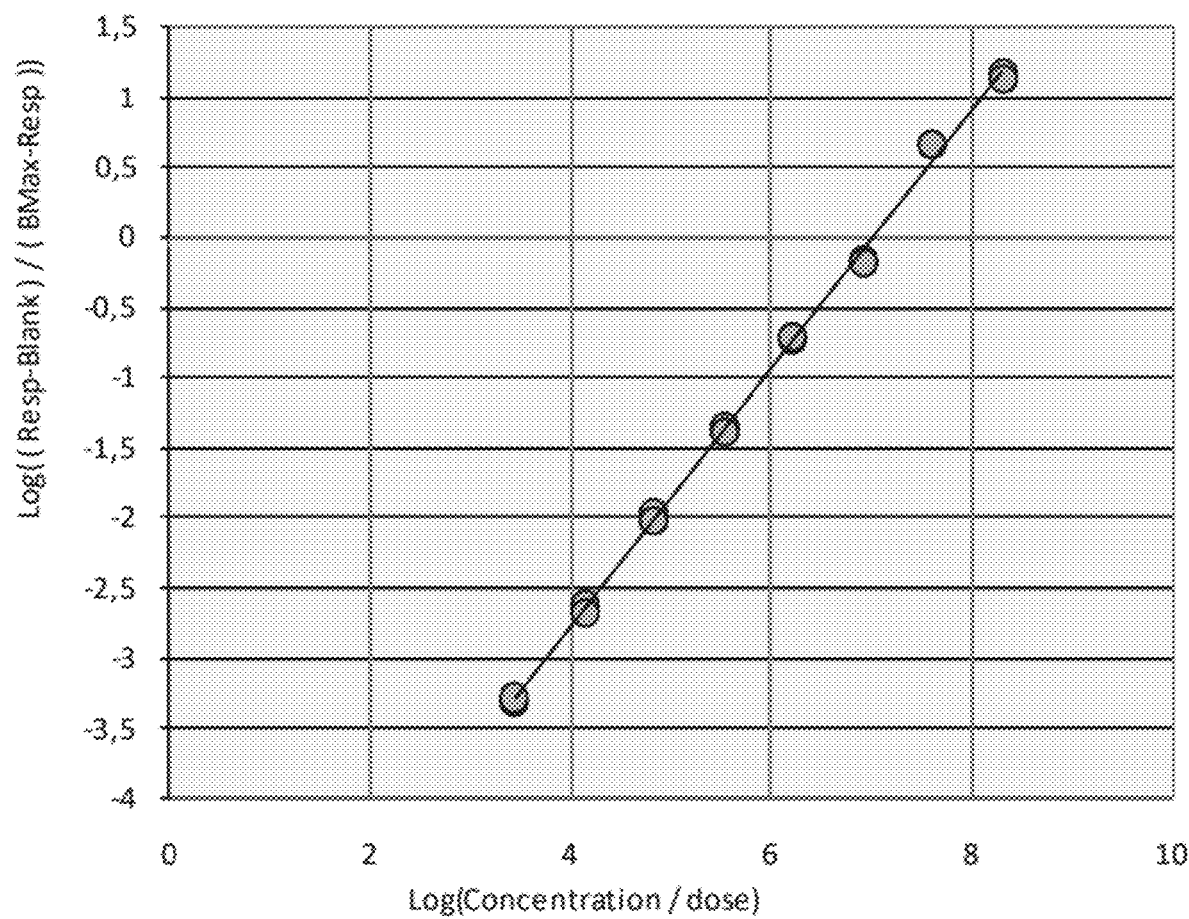
FIG. 43 is a graph showing a standard curve generated from ELISA assay results and used to calculate TNF-α production.
Figure 44:
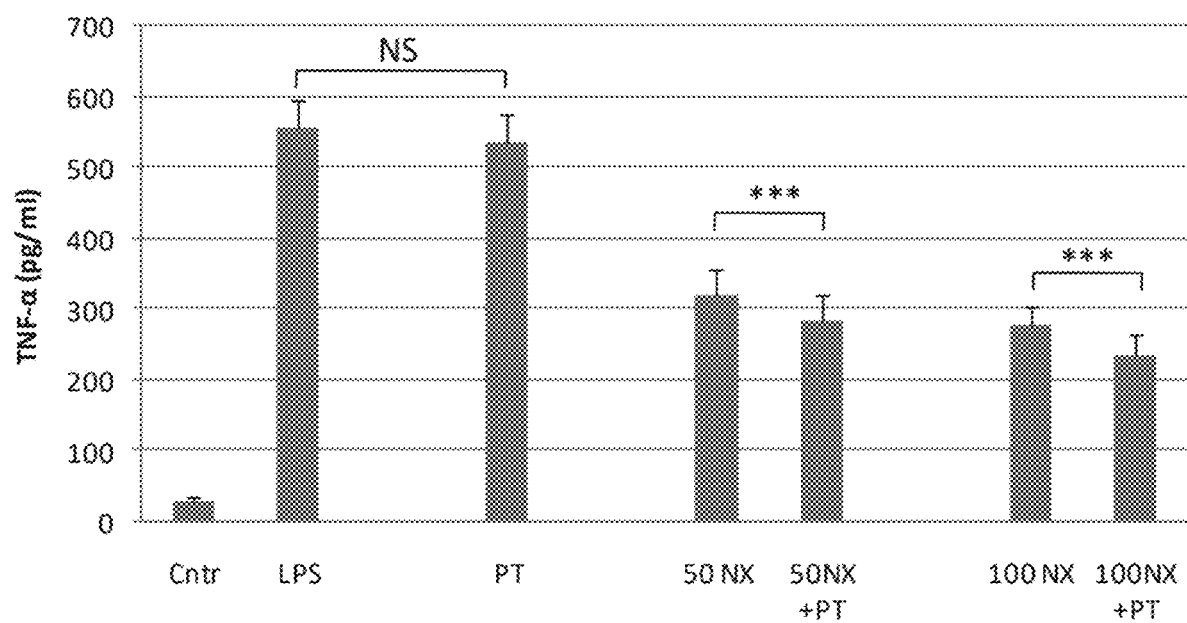
FIG. 44 is a graph showing amounts of TNF-α produced in RAW264.7 cells in the presence of Peptylin® and NeurXcel®.

After the treatments, the supernatants were collected and an ELISA assay was performed. First, the standard curve was generated (FIG. 43). Using these data, the pg/ml of TNF-α produced by the cells was calculated (FIG. 44).

TABLE 29

ELISA Assay (Standardized Curve)

| | |
| --- | --- |
| Correlation | 0.999311167 |
| Slope | 0.921410268 |
| Intercept | −6.449858739 |
| Blank | 0.0575 |
| Bmax | 4.22914434 |
| [½Bmax] | 1096.61752 |
| Iterations | 236 |

The TNF-α standard was measured in 8 serial 1:2 dilutions ranging from 0-4000 pg/ml.

TNF-α production was measured by ELISA. Control: cells maintained in DMEM; LPS: LPS-induced cells in DMEM+0.5% EtOH+1.2% H2O; PT: cells pre-treated with 60 μg/ml of Peptylin® for 24 h; 50 NX and 100 NX: cells treated with 50 or 100 μM NX for 24 h; 50NX+PT and 100NX+PT: cells pre-treated with 50 or 100 μM NX and 60 μg/ml PT for 24 h. Then the cells were induced with 500 ng/ml LPS for 1.5 h. The data represent the mean±SD of an experiment performed in nine replicates (for Cntr and LPS) or 24 replicates (for PT and NX treatments). NS: non-significant; *** $p<0.001$.

Peptylin® (60 μg/ml) did not affect the TNF-α levels. The treatment of cells with 50 μM NeurXcel® reduced 43% TNF-α levels while the co-treatment with PT reduced TNF-α 49%. According to the ttest analysis, there is a significant difference between treating the cells with 50 μM NX alone or in combination with PT ($p=5.6\times10^{-4}$). Besides, the TNF-α levels were reduced 50% when cells were treated with 100 μM NX and 58% when cells were co-treated with NX and PT. There is also a significant difference between treating the cells with 100 μM NX alone or in combination with PT ($p=1.2\times10^{-6}$).

5 Conclusions

According to the WST-8 assay, none of the treatments affect the cell viability in RAW264.7 cells. The treatment of cells with Peptylin® (60 μg/ml) did not affect TNF-α levels. The treatment of cells with 50 or 100 μM NX reduced TNF-α levels 43 and 50%, respectively, while the co-treatment with PT induced a reduction of 49 and 58%, respectively. According to the t-test analysis there is a significant difference in the TNF-α levels between treating the cells with NeurXcel® alone or in combination with Peptylin®.

Example 25

LPS-Induced Microglial Activation Assay: Neuroinflammation-Related In Vitro Model 1 Executive Summary 1.1 Aim The aim of the present study is to assay the effect of NeurXcel and Peptylin, used in combination or alone, in the LPS-induced IL-6 production in the mouse macrophage RAW264.7 cell line.

1.2 Methods Cells were seeded in 96 well plates. On day 2, cells were serum starved for 24 h. Then, cells were pretreated with 70, 50 or 30 μM NeurXcel alone or combined with 50 μg/ml Peptylin or Peptylin alone diluted in DMEM. Appropriate vehicle control was included, i.e. 0.5% ethanol. On day 4, cells were LPS-induced (500 ng/ml) for 6h, supernatants were collected and an IL-6 ELISA was carried out. Cell viability was tested with a WST-8 assay.

1.3 Results According to the WST-8 assay Peptylin had not an effect on cell viability while pretreatment with NX very slightly increased the number of viable cells at the end of the experiment. Pretreatment with NX had a protective effect on IL-6 release in response to LPS-mediated inflammation in a dose-dependent manner. Pretreatment with Peptylin produced a decrease in the amount of IL6 secreted and, in combination with NX, it enhances the protection of NX against LPS-induced inflammation in RAW264.7 cells.

1.4 Conclusion Taking into account the data from the previous experiments (Reports 21 and 22), we can conclude that NX have a protective effect on IL-6 secretion in LPS-induced inflammation in RAW264.7 cells. Furthermore, the combination of NX and Peptylin appears to increase the protective effect of NX.

2 INTRODUCTION Microglia are the primary antigen-presenting cells in the central nervous system. These immune-like cells can be activated in response to injury, disease, or inflammation, leading to the secretion of a variety of factors such as proinflammatory cytokines, prostaglandins, and reactive oxygen/nitrogen species, each of which can cause neuronal damage. LPS triggers an array of microglial response by interacting with the membrane receptor Toll-like receptor 4 (TLR4), leading to the production of proinflammatory mediates (e.g., cytokines and interleukins, TNFα, and IFNγ) and the self-activation of the nuclear factor NF-κB system. In this assay, the effect of different concentrations of NeurXcel, both alone and in combination with Peptylin will be measured in LPS-induced RAW264.7 cells to assess the production of IL-6.

3 Materials and Methods 3.1 Reagents and Equipment

TABLE 30

| Reagent/Equipment and Catalogue and Lot Numbers | Supplier |
| --- | --- |
| RAW264.7 (# Cat. ATCC TIB-71) | ATCC |
| Dulbecco's Modified Eagle's Medium-high glucose-(# Cat. D6429) | Sigma-Aldrich |
| FBS (# Cat. F7524) | Sigma-Aldrich |
| Penicillin/Streptomycin (# Cat. 15240) | Gibco |
| Trypsin-EDTA 0.5% (w/v) (# Cat. 25300) | Gibco |
| PBS (# Cat. D8537) | Sigma-Aldrich |
| Mouse IL-6 DuoSet ELISA (# Cat. DY406) | R&D Systems |
| DuoSet ELISA Ancillary Reagent Kit 2 (# Cat. DY008) | R&D Systems |
| Lipopolysaccharide, LPS (# Cat. L4391) | Sigma-Aldrich |
| Incubator (# Model 381 S/N 314342) | Thermo Scientific |
| Synergy II microplate reader | BioTek Instruments |

3.2. Test Compounds

TABLE 31

| | Test Compound: Peptylin ® |
| --- | --- |
| Test Item | Peptylin ® (powdered), a Purified *Bombyx mori* Cocoon Silk Peptide Fiber of this invention |
| Manufacturer | Famenity Co., Uiwang-si, S. Korea |
| Storage Conditions | The compound was protected from light and stored at room temperature. After reconstitution of the powder, samples were kept at 4° C. |
| Dilution protocol | Peptylin ® powder was dissolved in water to a concentration of 5 mg/ml. From this stock, the final 50 μg/ml concentration was prepared in DMEM. |

TABLE 32

| | Test Compound NeurXcel ® EE |
| --- | --- |
| Test Item | NeurXcel ®, ethyl ester (NeurXcel ® EE), a Refined *Buglossoides arvensis* Seed Oil of this invention |
| Manufacturer | Nature's Crops International Ltd., Kensington, PE, Canada |
| Storage Conditions | The compound was protected from light and stored at −20° C. |
| Molecular Weight | 305 |
| Dilution protocol | NeurXcel ® EE oil was provided as a 100% active compound. First, 10 mM and 6 mM dilutions were prepared in 100% ethanol, from which the 70, 50, and 30 uM working concentrations were prepared in DMEM medium (final ethanol concentration of 0.5%). |

3.3 Cell Culture

RAW264.7 cells were cultured in DMEM medium supplemented with 10% FBS in T75 flasks for 3 days. Cultures were maintained at 37° C. in a humidified atmosphere with 5% $CO_2$.

3.4 Experimental Procedure

Cells were seeded in 96 well plates at a density of 30,000 cells/well in DMEM+10% FBS. On day 2 the cells were washed once with DPBS and serum starved for 24 h in DMEM. Then, cells were pretreated with 70, 50 or 30 μM NeurXcel alone or combined with 50 μg/ml Peptylin or Peptylin alone diluted in DMEM. Appropriate vehicle control was included, i.e. 0.5% ethanol. On day 4 cells were LPS-induced (500 ng/ml) for 6 hours. After the incubation, the supernatants were collected and a WST-8 assay was carried out. CCK-8 reagent (WST-8) was diluted 1:10 in DMEM media and 100 μl were added to each well and the plate was incubated at 37° C. After 15 minutes the absorbance was measured at 450 nm using the Synergy II microplate reader. WST-8 is bioreduced by cellular dehydrogenases to an orange formazan product that is soluble in tissue culture medium. The amount of formazan produced is directly proportional to the number of living cells. The ELISA assay was performed following the manufacturer's instructions. All the experiments were carried out in triplicate.

4 Results

4.1 Cell Viability

Figure 45:
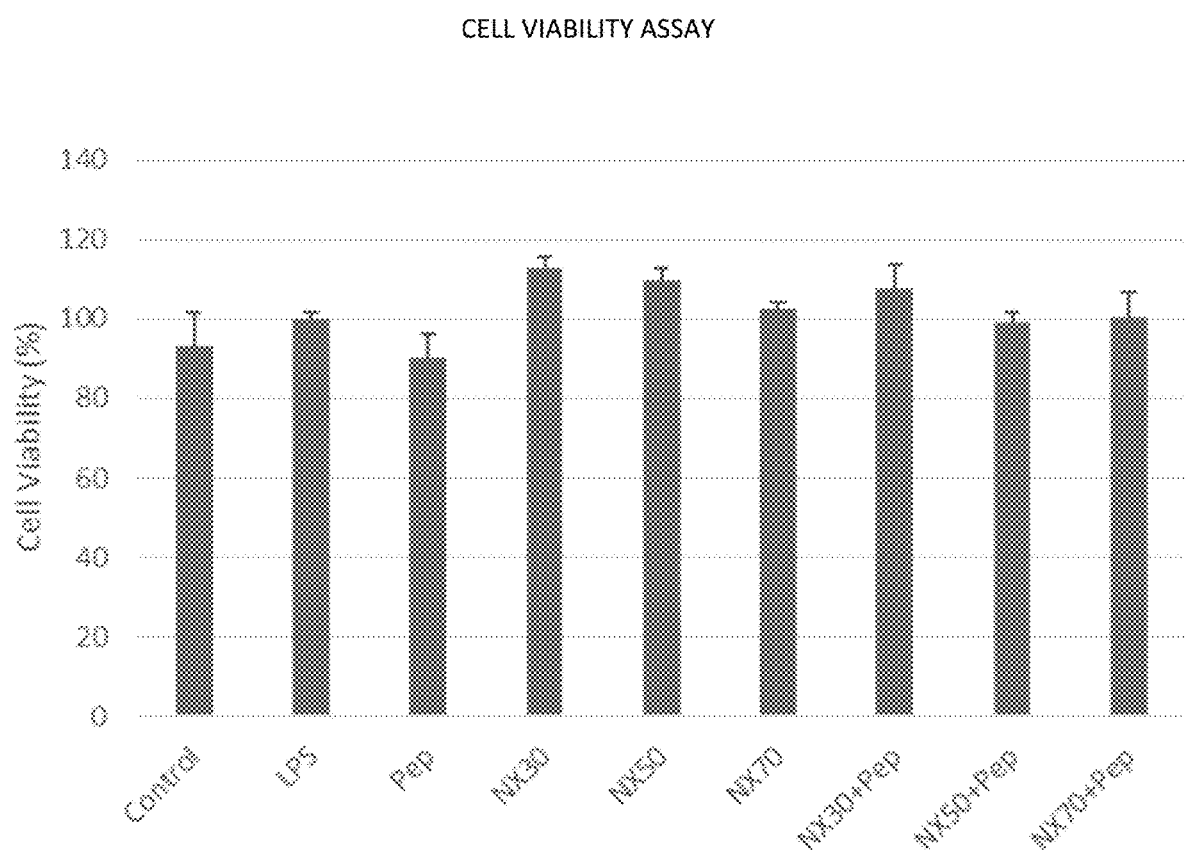
FIG. 45 is a graph showing WST-8 cell viability assay results after exposure of RAW264.7 cells to Peptylin® and NeurXcel®.

RAW264.7 cells were serum starved for 24 hours, pretreated for 24h with 70, 50 or 30 μM NeurXcel alone or combined with 50 μg/ml Peptylin or Peptylin alone diluted in DMEM and induced for 6 h with 500 ng/ml LPS. After the treatments, the supernatants were collected and the cells were incubated with the CCK-8 reagent for 15 minutes. The absorbance was measured at 450 nm using the Synergy II microplate reader. Peptylin® had no effect on cell viability while pretreatment with NX very slightly increased the number of viable cells (FIG. 54). In FIG. 45, data were normalized to the corresponding vehicle control (LPS-induced cells in DMEM+0.5% Ethanol) that is considered as 100% viability. The data represent mean±SD of an experiment performed in triplicate.

4.2 IL-6 Production

After the treatments, the supernatants were collected and an ELISA assay was performed. First, the standard curve was generated (FIG. 55, Table 33).

TABLE 33

| Standard Curve for ELISA Assay | |
|---|---|
| Correlation | 0.99857428 |
| Slope | 0.9966385 |

TABLE 33-continued

| Standard Curve for ELISA Assay | |
|---|---|
| Intercept | −6.45637192 |
| Blank | 0.077 |
| Bmax | 4.51697613 |
| [½Bmax] | 650.764773 |
| Iterations | 246 |

Standards were measured in 8 serial 1:2 dilutions ranging from 0 to 2000 pg/ml.

Figure 47:
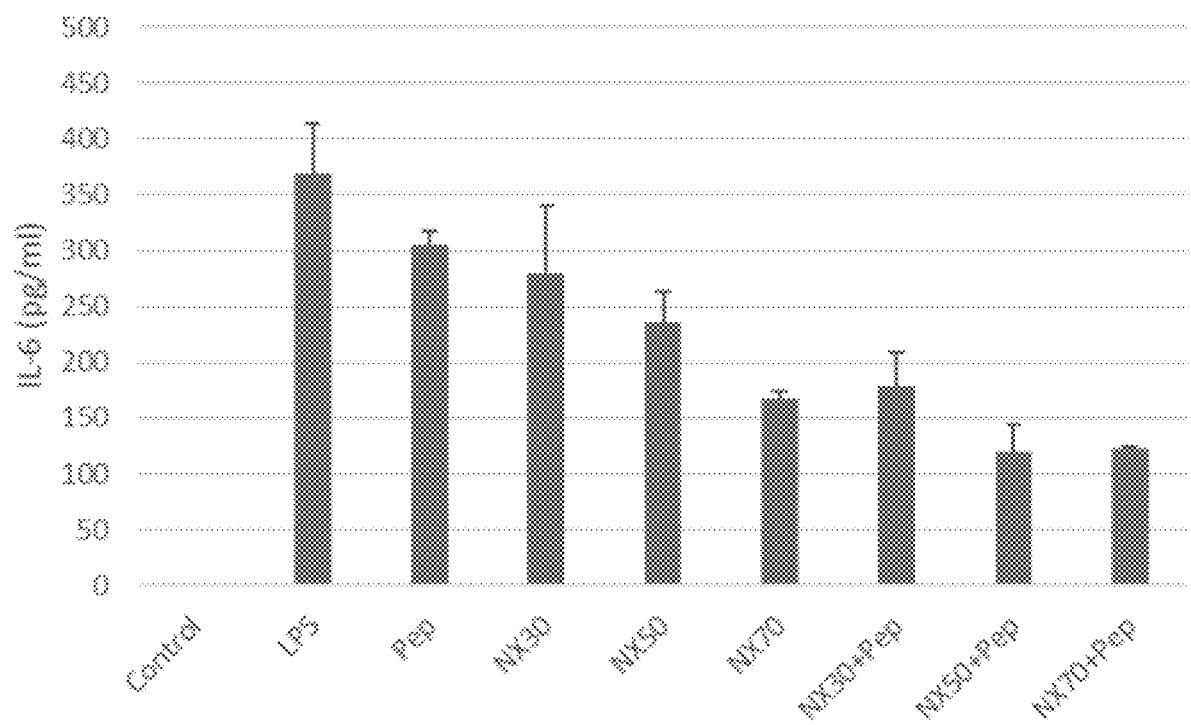
FIG. 47 is a graph showing amounts of IL-6 produced in RAW264.7 cells in the presence of Peptylin® and NeurXcel®.

Using these data, the pg/ml of IL-6 produced by the cells were calculated (FIG. 56). Pretreatment with NX had a protective effect on IL-6 release in response to LPS-mediated inflammation in a dose-dependent manner (% of reduction 24, 36 and 54% when pretreating with 30, 50 and 70 μM NeurXcel® respectively). Pretreatment with Peptylin produced a 17% decrease in the amount of IL-6 secreted and, in combination with NX, it appears to very slightly enhance the protection of NX against LPS-induced inflammation (% of reduction 51, 67 and 66% when pretreating with 30, 50 and 70 μM NeurXcel combined with 50 μg/ml Peptylin respectively). In FIG. 47, IL-6 production was measured by ELISA, and data represent the mean±SD of an experiment performed in triplicate.

TABLE 34

| WST-8 Assay, Raw Data | | | | | | | |
|---|---|---|---|---|---|---|---|
| | Abs 450 nm | | | Average | SD | Norm | SD |
| Control | 0.565 | 0.476 | 0.505 | 0.51533333 | 0.04539089 | 93.3011467 | 8.21802562 |
| LPS | 0.542 | 0.556 | 0.559 | 0.55233333 | 0.00907377 | 100 | 1.64280719 |
| Pep | 0.469 | 0.534 | 0.493 | 0.49866667 | 0.03286842 | 90.2836451 | 5.95083124 |
| NX30 | 0.614 | 0.613 | 0.64 | 0.62233333 | 0.01530795 | 112.673506 | 2.77150573 |
| NX50 | 0.624 | 0.594 | 0.598 | 0.60533333 | 0.01628906 | 109.595655 | 2.949135 |
| NX70 | 0.554 | 0.565 | 0.576 | 0.565 | 0.011 | 102.293301 | 1.991551 |
| NX30 + Pep | 0.63 | 0.59 | 0.565 | 0.595 | 0.03278719 | 107.724804 | 5.93612419 |
| NX50 + Pep | 0.541 | 0.562 | 0.541 | 0.548 | 0.01212436 | 99.2154496 | 2.19511569 |
| NX70 + Pep | 0.537 | 0.594 | 0.529 | 0.55333333 | 0.03544479 | 100.18105 | 6.41728294 |

Table 49 shows raw data for each condition. Average in the Table refers to average of six replicates. SD refers to Standard Deviation, Norm refers to normalization of all data to corresponding LPS control which is considered to be 100% of cell viability.

Figure 46:
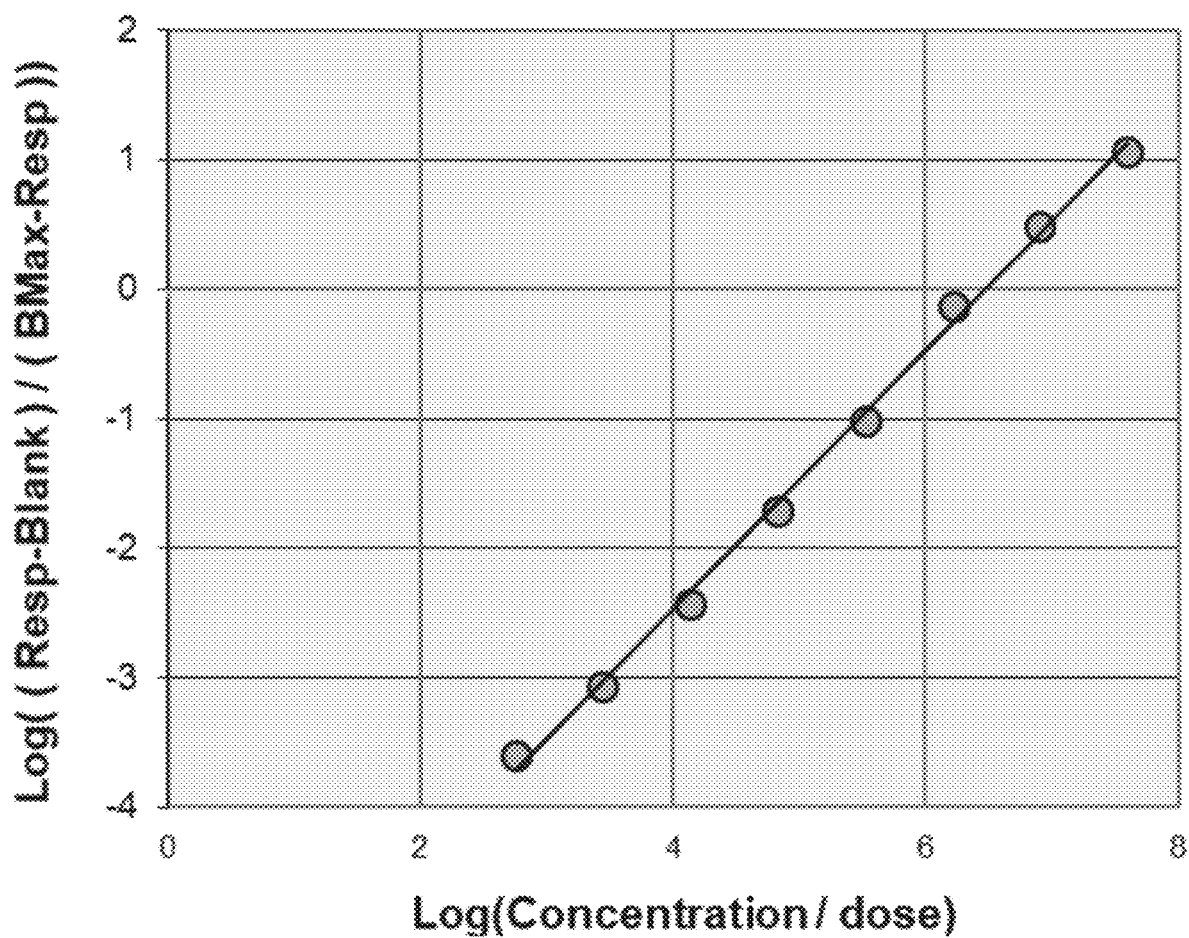
FIG. 46 is a graph showing a standard curve generated from ELISA assay results and used to calculate IL-6 production.

Table 35 shows data for the IL-6 ELISA Standard curve shown in FIG. 46.

TABLE 35

| IL-6 ELISA Standard Curve | |
|---|---|
| pg/ml IL-6 | Abs 450 nm |
| 0 | 0.077 |
| 15.625 | 0.195 |
| 31.25 | 0.276 |
| 62.5 | 0.436 |
| 125 | 0.756 |
| 250 | 1.255 |
| 500 | 2.154 |
| 1000 | 2.833 |
| 2000 | 3.38 |

TABLE 36

IL-6 ELISA Assay

|  | pg/ml IL-6 | | | | | | Average | SD | % of Reduction |
|---|---|---|---|---|---|---|---|---|---|
| Control | 0.077 | 0.083 | 0.077 | << | 0.861 | << | 0 | 0 | 100 |
| LPS | 1.545 | 1.801 | 1.694 | 321 | 412 | 372 | 368.333333 | 45.6106713 | 0 |
| Pep | 1.493 | 1.538 | 1.454 | 304 | 318 | 292 | 304.666667 | 13.0128142 | 17.28506787 |
| NX30 | 1.172 | 1.577 | 1.466 | 212 | 331 | 295 | 279.333333 | 61.0273163 | 24.16289593 |
| NX50 | 1.376 | 1.203 | 1.196 | 268 | 220 | 218 | 235.333333 | 28.3078317 | 36.10859729 |
| NX70 | 1.019 | 0.984 | 0.965 | 174 | 166 | 162 | 167.333333 | 6.11010093 | 54.57013575 |
| NX30 + Pep | 0.947 | 1.179 | 0.965 | 158 | 214 | 162 | 178 | 31.2409987 | 51.67420814 |
| NX50 + Pep | 0.695 | 0.695 | 0.897 | 105 | 105 | 147 | 119 | 24.2487113 | 67.69230769 |
| NX70 + Pep | 0.786 | 0.777 | 0.793 | 123 | 121 | 124 | 122.666667 | 1.52752523 | 66.69683258 |

Table 36 shows raw data for each condition. Using data obtained from the standard curve the amount of IL-6 in pg/ml was measured, as shown in FIG. 47. Average in the Table refers to average of the replicates, SD refers to Standard Deviation, % of Reduction represents the decrease in IL-6 (%) compared with LPS control.

5 Conclusions

According to the WST-8 assay, treatment with Peptylin® does not affect cell viability in RAW264.7 cells while NX increased the number of viable cells. NeurXcel® has a protective effect on IL-6 secretion in LPS-induced inflammation in RAW264.7 cells. The treatment of cells with Peptylin® (50 µg/ml) alone produced a decrease in the amount of IL-6 secreted and the combination of NX and Peptylin® increased the protective effect of NX.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±20%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. Reference to "about" an amount in a range applies to the entire range, for instance about 1-10 is intended to mean about 1 to about 10. All method steps described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof and, accordingly, reference should be made to the appended claims, rather than to the foregoing specification, as indicating the scope of the invention.

References to trademarked source materials are intended to be exemplary but not limiting throughout this application.

We claim:

1. A method of decreasing inflammation and/or oxidative stress in a subject, comprising the steps of:
   a. providing a composition comprising purified *Bombyx mori* cocoon silk peptide fiber and refined *Buglossoides arvensis* seed oil, wherein the purified *Bombyx mori* cocoon silk peptide fiber is water-soluble and is at least 85% by weight fibroin and less than 10% by weight sericin, and
   b. administering an effective amount of the composition to the subject to decrease inflammation and/or oxidative stress.

2. The method of claim 1, wherein said decrease in inflammation and/or oxidative stress provides neuroprotection to the subject.

3. A method of treating and/or preventing a disease or disorder in a subject, comprising the steps of:
   a. providing a composition comprising purified *Bombyx mori* cocoon silk peptide fiber and refined *Buglossoides arvensis* seed oil, wherein the purified *Bombyx mori* cocoon silk peptide fiber is water-soluble and is at least 85% by weight fibroin and less than 10% by weight sericin, and
   b. administering an effective amount of the composition to the subject to decrease inflammation and/or oxidative stress.

4. The method of claim 3, where in step b, inflammation and/or oxidative stress from a sugar is decreased.

5. The method of claim 3, wherein said disease or disorder is an inflammatory disease, an auto-immune disease, a cardiovascular disease, and/or a type of cancer.

6. The method of claim 3, wherein said inflammatory disease is an inflammatory neurological disease or an inflammatory gastrointestinal disease.

7. The method of claim 3, wherein said disease or disorder is Alzheimer's disease, autism, Parkinson's disease, Multiple Sclerosis, ALS (Lou Gehrig's disease), stroke, depression, chronic pain, dyslexia, memory impairment, attention deficit, forgetfulness, Alzheimer's dementia, vascular dementia, dementia, Parkinson's disease, a sleep disorder, dysgraphia, anxiety disorder, ADD, ADHD, autism spectrum disorder, Asperger's, strabismus, brain fog, concussion, a demyelination disorder, arthritis, rheumatoid arthritis, lupus, inflammatory bowel disease (IBD), Crohn's disease, Addison's disease, Grave's disease, myasthenia gravis, Hashimoto's disease, celiac disease, ulcerative colitis, gastritis; aiding recovery from a cardiovascular incident, a stroke, calcification of the heart, myocardial infarction; epilepsy; meningoencephalitis, Huntington's disease, brain injury, traumatic brain injury, leaky brain, and/or a neurodegenerative disorder, age-related dementia, concussion, chronic inflammation, heart disease, narcolepsy, non-alcoholic fatty liver disease, diabetes, prediabetes, neurocognitive defect, schizophrenia, major depressive disorder, or bipolar disorder.

8. A method of providing sequential treatment to a subject administered purified *Bombyx mori* cocoon silk peptide fiber, comprising the steps of:
 a. providing a composition comprising refined *Buglossoides arvensis* seed oil, and
 b. administering an effective amount of the composition to the subject to decrease inflammation and/or oxidative stress in the subject.

9. The method of claim 8, wherein said refined *Buglossoides arvensis* seed oil is administered in an amount of about 25-3000 mg daily.

10. The method of claim 9, wherein said refined *Buglossoides arvensis* seed oil is administered in an amount of about 50-1000 mg daily.

11. The method of claim 10, wherein said refined *Buglossoides arvensis* seed oil is administered in an amount of about 250-750 mg daily.

12. The method of claim 1, wherein said composition further comprises blueberry extract.

13. The method of claim 3, wherein said composition further comprises blueberry extract.

* * * * *